(12) United States Patent
De Man et al.

(10) Patent No.: US 10,494,360 B2
(45) Date of Patent: Dec. 3, 2019

(54) INHIBITORS OF INDOLEAMINE 2,3-DIOXYGENASE

(71) Applicant: NETHERLANDS TRANSLATIONAL RESEARCH CENTER B.V., AG Oss (NL)

(72) Inventors: Adrianus Petrus Antonius De Man, AH Hurwenen (NL); Joost Cornelis Marinus Uitdehaag, WR Oss (NL); Jan Gerard Sterrenburg, TE Renkum (NL); Joeri Johannes Petrus De Wit, JS Boekel (NL); Nicole Wilhelmina Cornelia Seegers, NN Heesch (NL); Antonius Maria Van Doornmalen, DA Kerkdriel (NL); Rogier Christian Buijsman, MK Berghem (NL); Guido Jenny Rudolf Zaman, KB Berghem (NL)

(73) Assignee: NETHERLANDS TRANSLATIONAL RESEARCH CENTER B.V, Oss (NL)

( * ) Notice: Subject to any disclaimer, the term of this patent is extended or adjusted under 35 U.S.C. 154(b) by 0 days.

(21) Appl. No.: 16/082,753

(22) PCT Filed: Mar. 8, 2017

(86) PCT No.: PCT/EP2017/055419
§ 371 (c)(1),
(2) Date: Sep. 6, 2018

(87) PCT Pub. No.: WO2017/153459
PCT Pub. Date: Sep. 14, 2017

(65) Prior Publication Data
US 2019/0055213 A1 Feb. 21, 2019

(30) Foreign Application Priority Data
Mar. 9, 2016 (EP) .................................. 16159508

(51) Int. Cl.
*C07D 401/04* (2006.01)
*C07D 233/32* (2006.01)
*A61P 37/00* (2006.01)
*A61P 33/00* (2006.01)
*A61P 25/28* (2006.01)
*A61P 31/12* (2006.01)
*A61P 35/00* (2006.01)

(52) U.S. Cl.
CPC ............ *C07D 401/04* (2013.01); *A61P 25/28* (2018.01); *A61P 31/12* (2018.01); *A61P 33/00* (2018.01); *A61P 35/00* (2018.01); *A61P 37/00* (2018.01); *C07D 233/32* (2013.01)

(58) Field of Classification Search
CPC .......................... C07D 403/12; C07D 401/04
See application file for complete search history.

(56) References Cited

U.S. PATENT DOCUMENTS 7,799,782 B2 * 9/2010 Munson ............... C07D 231/56
514/234.5

OTHER PUBLICATIONS

Su et al. CAS: 160: 734888, 2014.*
Munn, David, et al., "Prevention of Allogeneic Fetal Rejection by Tryptophan Catabolism." Science, vol. 281, pp. 1191-1193 (1998).
Uyttenhove, Catherine, et al., "Evidence for a Tumoral Immune Resistance Mechanism based on Tryptophan Degradation by Indolemine 2,3-dioxygenase." Nature Medicine. vol. 9. pp. 1269-1274. 2003.
Yue, Eddy et al. "Discovery of Potent Competitive Inhibitors of Indoleamine 2,3-Dioxygenase with in Vivo Pharmacodynamic Activity and Efficacy in a Mouse Melanoma Model." Journal of Medicinal Chemistry, vol. 52, pp. 7364-7367. 2009.
Koblish, Holly, et al. "Hydroxyamidine Inhibitors of Indoleamine-2,3-dioxygenase Potently Suppress Systemic Tryptophan Catabolism and the Growth of IDO-Expressing Tumors." Mol Cancer Ther. pp. 489-498. 2010.
Théate, Ivan, et. al. "Extensive profiling of the expression of the indoleamine 2,3-dioxygenase 1 protein in normal and tumoral human tissues." Cancer Immunology Research, pp. 1-35, 2014.
Brandacher, Gerald, et. al. "Prognostic value of indoleamine 2,3-dioxygenase expression in colorectal cancer: effect on tumor-infiltrating T cells." Clinical Cancer Research, vol. 12, p. 1144-1151, 2006.
Ino, K., et. al. "Indoleamine 2,3-dioxygenase is a novel prognostic indicator for endometrial cancer." British Journal of Cancer, vol. 95, pp. 1555-1561, 2006.

(Continued)

*Primary Examiner* — Rei Tsang Shiao
(74) *Attorney, Agent, or Firm* — Oliff PLC

(57) ABSTRACT

A compound of Formula I:

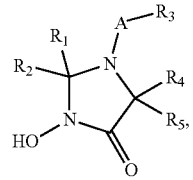

Formula I or pharmaceutically acceptable enantiomers, or salts thereof. The present invention also relates to the use of compounds of Formula (I) as selective inhibitors of indoleamine 2,3-dioxygenase. The invention also relates to the use of the compounds of Formula (I) for the treatment or prevention of diseases cancer, infections, central nervous system disease or disorder, and immune-related disorders, either as a single agent or in combination with other therapies.

15 Claims, No Drawings

(56) References Cited

OTHER PUBLICATIONS

Munn, David H., et. al. "Selective Activation-Induced Apoptosis of Peripheral T Cells Imposed by Macrophages: A Potential Mechanism of Antigen-Specific Peripheral Lymphocyte Delection." The Journal of Immunology, vol. 156, pp. 523-532, 1996.
Muller, Alexander J., et. al. "Inhibition of indoleamine 2,3-dioxygenase, an immunoregulatory target of the cancer suppression gene Bin1, potentiates cancer chemotherapy." Nature Medicine, vol. 11, No. 3, pp. 312-319, 2005.
Ou, Xueling, et. al. "Enhancement of dendritic cell-tumor fusion vaccine potency by indoleamine-pyrrole 2,3-dioxygenase inhibitor, 1-MT." J Cancer Research Clinical Oncology, vol. 134, pp. 525-533, 2008.
Zeng, Jun, et. al. "Prevention of Spontaneous Tumor Development in a ret Transgenic Mouse Model by Ret Peptide Vaccination with Indoleamine 2,3-Dioxygenase Inhibitor 1-Methyl Trypotphan." Cancer Resarch, vol. 69, pp. 3963-3970, 2009.
Holmgaard, Rikke B., et. al. "Indoleamine 2,3-dioxygenase is a critical resistance mechanism in antitumor T cell immunotherapy targeting CTLA-4." The Journal of Experimental Medicine, vol. 210, No. 7, pp. 1389-1402, 2013.
Wainwright, Derek., et. al. "Durable Therapeutic Efficacy Utilizing Combinatorial Blockade against IDO, CTLA-4, and PD-L1 in Mice with Brain Tumors." Clinical Cancer Research, vol. 20, No. 20, pp. 5290-5301, 2014.
Yoshida, Ryotaro, et. al. "Inducation of indoleamine 2,3-dioxygenase in mouse lung during virus infection." Proceedings of the National Academy of Sciences of the United States of America, vol. 76, No. 8, pp. 4084-4086, 1979.
Fox, Julie M., et. al. "Inhibition of indoleamine 2,3-dioxygenase enhances the T-cell response to influenza virus infection." Journal of General Virology, vol. 94, pp. 145-1461, 2013.
Makala, Levi, H. C., et. al. "Leishmania major Attenuates Host Immunity by Stimulating Local Indoleamine 2,3-Dioxygenase Expression." Journal of Infectious Diseases, vol. 203, pp. 715-725, 2011.
Vécsei, László. "Kynurenines in the CNS: recent advances and new questions." Nature Reviews, vol. 12, pp. 64-82, 2013.
Bonaccorso, Stefania, et. al. "Depression induced by treatment with interferon-alpha in patients affected by hepatitis C virus." Journal of Affective Disorders, vol. 72, pp. 237-241, 2002.
Maes, Michael, et. al. "Relationships Between Lower Plasma L-Tryptophan Levels and Immune-Inflammatory Variables in Depression." Psychiatry Research, vol. 49, pp. 151-165, 1993.
Bonaccorso, Stefania, et. al. "Increased Depressive Ratings in Patients with Hepatitits C Receiving Interferon-a-Based Immunotherapy Are Related to Interferon-a-Induced Changes in the Serotonergic System." Journal of Clinical Psychopharmacology, vol. 22, No. 1, pp. 86-90, 2002.
Bianchi, Mauro, et. al. "Central effects of tumor necrosis factor a and interleukin-1a on nociceptive thresholds and spontaneous locomotor activity." Neurosciene Letters, vol. 148, pp. 76-80, 1992.
Bluthé, R.M., et. al. "Synergy Between Tumor Necrosis Factor a and Interleukin-1 in the Induction of Sickness Behavior in Mice." Psychoneuroendocrinology, vol. 19, No. 2, pp. 197-207, 1994.
Reynolds, Gavin P., et. al. "Brain Quinolinic Acid in Huntington's Disease." Journal of Neurochemistry, vol. 50, No. 6, pp. 1959-1960, 1988.
Reynholds, G.P. and S.J. Pearson. "Increased Brain 3-Hydroxykynurenine in Huntington's Disease." The Lancet, vol. 2, pp. 979-980, 1989.
Ogawa, T., et. al. "Kynureine pathway abnormalities in Parkinson's disease." Neurology, vol. 42, pp. 1702-1706, 1992.
Heyes, Melvyn P., et. al. "Sources of the neurotoxin quinolinic acid in the brain of HIV-1-infected patients and retrovirus-infected macaques." Faseb Journal, vol. 12, pp. 881-896, 1998.
Moroni, Flavio, et. al. "The Exitotoxin quinolinic Acid is Present in the Brain of Several Mammals and its Cortical Content Increases During the Aging Process." Neuroscience Letters, vol. 47, pp. 51-55, 1984.
Heyes, Melvin P., et. al. "Quinolinic acid in tumors, hemorrhage and bacterial infections of the central nervous system in children." Journal of the Neurological Sciences, vol. 133, pp. 112-118, 1995.
Sanni Latifu A., et. al. "Dramatic Changes in Oxidative Tryptophan Metabolism along the Kynurenine Pathway in Experimental Cerebral and Noncerebral Malaria." American Journal of Pathology, vol. 152, No. 2, pp. 611-619, 1998.
Saito, Kuniaki, et. al. "Kynurenine Pathway Enzymes in Brain: Responses to Ischemic Brain Injury Versus Systemic Immune Activation." Journal of Neurochemistry, vol. 61, No. 6, pp. 2061-2070, 1993.
Kazda, Hana, et. al. "Maternal, Umbilical, and Amniotic Fluid Concentrations of Tryptophan and Kynurenine after Labor or Cesarean Section." Pediatric Research, vol. 44, pp. 368-373, 1998.
Sinz, Elizabeth H., et. al. "Quinolinic Acid is Increased in CSF and Associated with Mortality after Traumatic Brain Injury in Humans." Journal of Cerebral Blood Flow and Metabolism, vol. 18, No. 6, pp. 610-615, 1998.
Heyes, Melvyn P. et. al. "Quinolinic Acid Concentrations in Brain and Cerebrospinal Fluid of Patients with Intractable Complex Partial Seizures." Epilepsia, vol. 31, No. 2, pp. 172-177, 1990.
Orlikov, Alexei B., et.al. "Kynurenine in Blood Plasma and DST in Patients with Endogenous Anxiety and Endogenous Depression." Society of Biological Psychiatry, vol. 36, pp. 97-102, 1994.
Issa, Fuad, et. al. "A Multidimensional Approach to Analysis of Cerebrospinal Fluid Biogenic Amines in Schizophrenia: II Correlations with Psychopathology." Psychiatry Research, vol. 52, pp. 251-258, 1994.
Lee, Alexander, et. al. "ID01 and ID02 Non-Synonymous Gene Variants: Correlation with Crohn's Disease Risk and Clinical Phenotype" PLoS ONE, vol. 9, pp. 1-15, 2014.
Shon, Woo-Jeong, et. al. "Severity of DSS-induced colitis is reduced in Ido1-deficient mice with down-regulation of TLR-MyD88-NF-kB transcriptional networks." Scientific Reports, vol. 5, pp. 1-12, 2015.
André, Caroline, et. al. "Diet-induced obesity progressively alters congnition, anxiety-like behavior and ipopolysaccharide-induced depressive-like behavior: Focus on brain indoleamine 2,3-dioxygenase activation." Brain, Behavior, and Immunity, vol. 41, pp. 10-21, 2014.
Favennec, Marie, et. al. "The Kynurenine Pathway is Activated in Human Obesity and Shifted Toward Kynurenine Monooxygenase Activation." Obesity, Biology, and Integrated Physiology, vol. 23, No. 10, pp. 2066-2074, 2015.
Yue, Eddy W., et. al. "Discovery of Potent Competitive Inhibitors of Indoleamine 2,3-Dioxygenase with in Vivo Pharmacodynamic Activity and Efficacy in a Mouse Melanoma Model." Journal of Medicinal Chemistry, vol. 52, pp. 7364-7367, 2009.
Seegers, Nicole, et. al. "High-Throughout Fluorescence-Based Screening Assays for Tryptophan-Catabolizing Enzymes." Journal of Biomolecular Screening, vol. 19, No. 9, pp. 1266-1274, 2014.
Lu, Changyuan, et. al. "Inhibitory Substrate Binding Site of Human Indoleamine 2,3-Dioxygenase." Journal of American Chemical Society, vol. 131, pp. 12666-12667, 2009.
Klockow, Jessica L. and Timothy E. Glass. "Development of a Fluorescent Chemosensor for the Detection of Kynurenine." Organic Letters, vol. 15, No. 2, pp. 235-237, 2013.
Schuts, Gunther and Philip Feigelson. "Purification and Properties of Rat Liver Tryptophan Oxygenase." The Journal of Biological Chemistry, vol. 247, No. 17, pp. 5327-5332, 1972.
Cady, Susan G. and Masanori Sono. "1-Mthyl-DL-Tryptophan, b-(3-Benzofuranyl)-DL-alanine (the Oxygen Analog of Tryptophan), and b-[3-Benzo(b)thienyl]-DL-alanine (the Sulfur Analog of Tryptophan) Are Competitive Inhibitors for Indoleamine 2,3-Dioxygenase." Archives of Biochemistry and Biophysics, vol. 291, No. 2, pp. 326-333, 1991.
Matin, Azadeh, et. al. "A fluroescence-based assay for indoleamine 2,3-dioxygenase." Analytical Biochemistry, vol. 349, pp. 96-102, 2006.
Takikawa, Osamu, et. al. "Mechanism of Interferon-y Action: Characterization of Indoleamine 2,3-Dioxygenase in Cultured Human Cells Induced by Interferon-y and Evaluation of the Enzyme-

(56) References Cited

OTHER PUBLICATIONS

Mediated Tryptophan Degradation in its Anticellular Activity." The Journal of Biological Chemistry, vol. 263, No. 4, pp. 2041-2048, 1988.
Su, Zhiwei, et. al. Chemical Composition and Cytotoxic Activities of Petroleum Ether Fruit Extract of Fruits of Brucea avanica (Simarubaceae), Tropical Journal of Pharmaceutical Research, vol. 12, No. 5, pp. 735-742, 2013.
Apr. 5, 2017 International Search Report issued in International Patent Application No. PCT/EP2017/055419.
Apr. 5, 2017 Written Opinion issued in International Patent Application No. PCT/EP2017/055419.

* cited by examiner

INHIBITORS OF INDOLEAMINE 2,3-DIOXYGENASE

The present invention relates to 3-hydroxyimidazolidin-4-one derivatives, to pharmaceutical compositions comprising these compounds and their use in therapy. In particular, the present invention relates to the use of 3-hydroxyimidazolidin-4-one derivatives for the treatment and/or prevention of cancer, infections, central nervous system disease or disorders, and immune-related disorders.

The present invention relates to 3-hydroxyimidazolidin-4-one compounds which modulate the activity of indoleamine 2,3-dioxygenase, in particular inhibit the activity of indoleamine 2,3-dioxygenase. Indoleamine 2,3-dioxygenase (IDO1, EC 1.13.11.52) is an oxidoreductase that catalyzes the first and rate-limiting step of the kynurenine pathway of L-tryptophan degradation. L-tryptophan is an essential amino acid required for the synthesis of proteins and the production of the neurotransmitter 5-hydroxy tryptamine (serotonin) and niacin (vitamin $B_3$). Both L-tryptophan and L-tryptophan metabolites formed along the kynurenine pathway are regulators of the local immune response. IDO1 plays an important role in immune tolerance. Studies of mammalian pregnancy have indicated that IDO1 expressed in the placenta protects the fetus against the maternal immune response, thus preventing fetal rejection in utero (Munn, D. H., et al., Science 281: 1191; 1998). Tumor cells expressing IDO1 create a similar state of immune tolerance (Uyttenhove, C., et al., Nat. Med. 9: 1269; 2003). IDO1 expressed in mouse tumor cells prevented their rejection by pre-immunized mice and this effect could be reverted by 1-methyl-L-tryptophan (1-MT), a low-potency inhibitor of IDO1 (Uyttenhove, C., et al.). 4-amino-N-(3-chloro-4-fluorophenyl)-N'-hydroxy-1,2,5-oxadiazole-3-carboximidamide (compound 51), a potent IDO1 inhibitor showed reduction of tumor growth in a mouse model for melanoma (Yue, E. W., et al., J. Med. Chem. 52: 7364; 2009). Two other potent IDO1 inhibitors from the same chemical series suppressed tumor growth in a mouse model for colon cancer (Koblish, H. K., et al., Mol. Cancer Ther. 9: 489; 2010). Many human tumors constitutively express IDO1 (Uyttenhove, C., et al.). In a series of 866 human tumors from diverse tissue-type origin more than half (i.e., 56%) expressed IDO1 (Théate, I., et al., Cancer Immunol. Res. 3: 161; 2014). High expression of IDO1 correlated with poor prognosis in a variety of cancers, including colorectal and endometrial cancer (Brandacher, G., et al., Clin. Cancer Res. 12: 1144; 2006; Ino, K., et al., Br. J. Cancer 95: 1555; 2006). In the absence of an immunologic stimulus, IDO1 is generally absent in most normal human tissues and cells (Théate, I., et al.).

Above data provide the biological basis for the use of IDO1 inhibitors as an approach for selective anti-cancer therapy.

It is understood that IDO1 inhibitors exert their anti-tumour activity either directly by affecting IDO1-expressing tumors or indirectly by inhibiting IDO1 in immune cells in the microenvironment of the tumor (Munn, D. H., et al., J. Immunol. 156: 523; 1996).

IDO1 inhibitors can be applied in anti-cancer therapy as single anti-cancer agent (monotherapy) or in combination with other anti-cancer agents. Administration of the IDO1 inhibitor 1-methyl-tryprophan (1-MT) increased the efficacy of various chemotherapeutic agents, e.g., cis-platin, doxorubicin, cyclophosphamide and paclitaxel in a mouse breast cancer model (Muller, A. J., et al., Nat. Med. 11: 312; 2005). 1-MT also increased the efficacy of a cancer vaccine in a syngeneic mouse lung carcinoma model (Ou, X., et al., J. Cancer Res. Clin. Oncol. 134: 525; 2008) and in a transgenic mouse model (Zeng, J., et al., Cancer Res. 69: 3963; 2009). 1-MT also increased the efficacy of antibodies targeting the immune checkpoints PD-1 and CTLA4 in mouse tumor models for melanoma and glioblastoma (Holmgaard, R. B., et al., J. Exp. Med. 210: 1389; 2013; Wainwright, D. A., et al., Clin. Cancer Res. 20: 5290; 2014).

IDO1 inhibitors may also be applied in anti-cancer therapy with other agents that activate the immune response, such as radiotherapy, or cellular therapies that attack tumor cells directly, such as natural killer cell or T cell therapies.

Certain viral infections, such as influenza virus, attenuate host immunity by stimulating local IDO1 activity (Yoshida, R., et al., Proc. Natl. Acad. Sci. USA 76: 4084; 1979). Treatment of influenza virus-infected mice with the IDO1 inhibitor 1-MT enhanced T cell response against the virus (Fox, J. M., et al., J. Gen. Virol. 94: 1451; 2013). Also certain parasitic infections, for instance, infection with *Leishmania major*, attenuates host immunity by stimulating IDO1 expression (Makala, L. H. C., et al., Journal of Infectious Diseases 203: 715; 2011). Treatment of these parasitic infections with the IDO1 inhibitor 1-MT reduced the parasite burden (Makala, L. H. C., et al.).

Above data provide a biologic basis for the use of IDO1 inhibitors in the treatment of viral and parasitic infections.

L-Tryptophan and metabolites formed along the kynurenine pathway play diverse role in the regulation of functions of the central nervous system (Vécsei, L., et al., Nat. Rev. Drug Discov. 12: 64; 2013). L-tryptophan is a precursor of serotonin (5-hydroxy tryptamine). Pro-inflammatory cytokine therapy with alpha-interferon (IFNα), as applied in hepatitis C and cancer, is associated with neuropsychiatric side-effects (Bonaccorso, S., et al., J. Affect. Disord. 72: 237; 2002). The development of depressive symptoms is, amongst others, related to decreased levels of peripheral serotonin (Maes, M., et al., Psychiatry Res. 49: 151; 1993). IFNα therapy in patients with hepatitis C causes decreased L-tryptophan levels and increased levels of the L-tryptophan metabolite kynurenine, indicating increased IDO1 activity (Bonaccorso, S., et al., J. Clin. Psychopharmacol. 22: 86; 2002). Administration of IFNα and other pro-inflammatory cytokines, such as interleukin-1β (IL-1β), IL-6 and tumor necrosis factor α (TNFα), to mice and rats induced a behavioral pattern characterized by increased sleep and decreased locomotor activity, referred to as 'sickness syndrome', which resembles the vegetative symptoms of depression in humans (Bianchi, M., et al., Neurosci. Lett. 148: 76; 1992; Bluthe, R. M., et al., Psychoneuroendocrinology 19:197; 1994).

Apart from the effect of L-tryptophan on serotonin, metabolites formed in the kynurenine pathway have neurotoxic activity. Increased production of the metabolites 3-hydroxy-kynurenine and quinolinic acid have been found in the brains of people with Huntington's disease (Reynolds, G. P., et al., J. Neurochem. 50: 1959; 1988; Reynolds, G. P., and Pearson, S. J., Lancet 2: 979; 1989), Parkinson's disease (Ogawa, T., et al., Neurology 42: 1702; 1992) and human immunodeficiency virus (HIV) associated neurocognitive disorder (AIDS dementia complex) (Heyes, M. P., et al., FASEB J., 12: 881; 1998). Increased production of metabolites has also been implicated in neuronal damage in cognitive decline of aging (Moroni, F., et al., Neurosci. Lett. 47: 51; 1984), infections of the central nervous system (Heyes, M. P., et al., J. Neurol. Sci. 133: 112; 1995), malaria (Sanni, L. A., et al., Am. J. Pathol. 152: 611; 1998), ischemia (Saito, K., et al., J. Neurochem. 60: 180; 1993), hypoxia at birth (Kazda, H., et al., Pediatr. Res. 44: 368; 1998), traumatic brain injury (Sinze, E. H., et al., J. Cereb. Blood Flow Metab. 18: 610; 1998), epilepsy (Heyes, M. P., et al., Epilepsia 31: 172; 1990), and the development of psychiatric diseases, such as anxiety, depression and schizophrenia (Orlikov, A. B., et al., Biol. Psychiatry 36: 97; 1994; Issa, F., et al., Psychiatry Res. 52: 251; 1994).

Above data provide the biological basis for the application of IDO1 inhibitors in the treatment of neuropsychiatric and neurodegenerative disease, as well as cerebrovascular disease.

Increased expression of IDO1 has been observed in Crohn's disease in human patients (Lee, A., et al., PLoS ONE 9: e115848; 2014), while inactivation of the IDO1 gene in mice reduced the severity of colitis symptoms (Shon, W. J., et al., Sci. Rep. 5: 17305; 2015). This suggests that IDO1 inhibitors may be applied in the treatment of immune-related diseases and disorders, such as inflammatory bowel disease, colitis or Crohn's disease.

Diet-induced obesity can activate the production of cytokines, such of IFNγ, resulting in increased IDO1 in the brain and neuropsychiatric alterations (André, C. et al., Brain Behav. Immun. 41: 10; 2014). Furthermore, increased levels of IDO1 and kynurenine have been observed in diabetic patients (Favennec, M., et al., Obesity (Silver Spring) 23: 2066; 2015). This suggests that IDO1 inhibitors may be applied in the treatment of metabolic diseases, such as obesity and diabetes.

Thus inhibiting IDO1 activity, thereby increasing L-tryptophan concentrations and decreasing L-tryptophan metabolite concentration is a promising way of treating diseases, disorders and other pathological conditions arising from an increased L-tryptophan degradation.

Small molecule inhibitors of IDO1 are currently being developed to treat or prevent pathological conditions that are dependent or induced by increased degradation of L-tryptophan or by increased formation of metabolites of L-tryptophan, such as the diseases and disorders described above.

The use of small molecule inhibitors of IDO1 in therapy has been described. WO99/29310 describes methods for altering T cell-mediated immunity by altering local extracellular concentrations of L-tryptophan by inhibition or activation of L-tryptophan degradation. In particular, the use of IDO1 inhibitors to achieve inhibition of L-tryptophan degradation is described, disclosing the IDO1 inhibitor 1-methyl-tryptophan (1-MT). 1-MT was first described as an inhibitor of IDO1 in Cady, S. G., and Sono, M., Arch. Biochem. Biophys. 291: 326; 1991. 1-MT is a low-potency inhibitor of IDO1 with an inhibitory constant ($K_i$) of 7 μM. WO2008/058178 A1 describes N-hydroxyamidines as inhibitors of IDO1. One of these compounds, compound 51, showed reduction of tumor growth in a mouse model for melanoma (Yue, E. W., et al., J. Med. Chem. 52: 7364; 2009). WO2015/188085 discloses N'-hydroxyacetimidamides that modulate the IDO1 enzyme. WO2011/056652 A1 describes imidazole derivatives as IDO1 inhibitors. WO2015/173764 A1 and WO2015/150097 A1 describe indole derivatives as inhibitors of IDO1.

Several compounds described as IDO1 inhibitors have been found to also inhibit the activity of tryptophan 2,3-dioxygenase (TDO) in biochemical assays (Seegers, N., et al., J. Biomol. Screen. 19: 1266; 2014), such as for example compound 51 from Yue, E. W., et al., and compound S7111, a fused imidazole (Selleck Chemicals, Munich, Germany; cat. no. S7111).

TDO is a structurally unrelated oxidoreductase that catalyzes the same reaction as IDO1 in the kynurenine pathway. TDO has a lower affinity ($K_{M,Trp}$) for L-tryptophan (190 μM) than IDO1 (6 μM) (Lu, C., et al. J. Am. Chem. Soc. 131: 12866; Klockow, J. L. et al., Organic Lett. 15: 235; 2013). TDO is mainly expressed in the liver where it regulates systemic L-tryptophan levels and L-tryptophan homeostasis (Schutz, G. et al., J. Biol. Chem. 247: 5237; 1995). Inhibition of TDO by an IDO1 inhibitor can however cause an unwanted alteration of these systemic L-tryptophan levels and L-tryptophan homeostasis. L-tryptophan is required for the de novo synthesis of reduced nucleotide amine dinucleotide (NADH), an essential co-enzyme in redox reactions and present in all living cells. Cross-reactivity of IDO1 inhibitors against TDO can be determined in enzyme assays.

Imidazole, and in particular 4-phenylimidazole, is a known binder of heme. Both IDO1 and TDO contain a heme cofactor. Also cytochrome P450 enzymes (CYPs), which are enzymes involved in the metabolism of drugs in the liver and other organs, contain a heme cofactor. Inhibition of CYP activity can cause adverse drug interactions, since by inhibition of CYP, one drug may affect the metabolism and clearance of a second drug. Consequently, the second drug may accumulate to toxic levels within the body, and adjustments of dosage levels may be necessary. Cross-reactivity of IDO1 inhibitors against CYPs can be determined in enzyme assays.

In view of the role of IDO1 in (the onset of) a variety of human diseases, disorders and other pathological conditions, there is a clear need for IDO1 inhibitors which do not have the limitations of current IDO1 inhibitors.

It is an object of the invention to provide novel IDO1 inhibitors. It is another object of the invention to provide novel IDO1 inhibitors which are selective for IDO1 and do not cross-react with TDO and/or CYP. It is yet a further objective of the present invention to provide novel, selective IDO1 inhibitors which have good potency.

The present invention provides for such IDO1 inhibitors. More specifically, the present invention provides for 3-hydroxyimidazolidin-4-one derivatives according to Formula I and pharmaceutically acceptable salts thereof. In particular, the present invention provides for 3-hydroxyimidazolidin-4-one derivatives which have been found to be potent inhibitors of IDO1. The present invention provides for 3-hydroxyimidazolidin-4-one derivatives which selectively inhibit IDO1 activity, their use for treatment or prevention of human disease, disorders or conditions associated with an increased activity of IDO1, as a sole agent or in combination with other active ingredients, as well as pharmaceutical compositions comprising such compounds and pharmaceutical carriers.

The present invention is to provide 3-hydroxyimidazolidin-4-one derivatives and pharmaceutically acceptable salts thereof, to pharmaceutical compositions comprising these compounds and their use in therapy. In particular, the present invention relates to the use of 3-hydroxyimidazolidin-4-one derivatives in the treatment and/or prevention of a diverse array of diseases, conditions and disorders associated with an increased activity of IDO1, including cancer, infections, central nervous system disease or disorder, and immune-related disorders.

More specifically, the present invention provides 3-hydroxyimidazolidin-4-one derivatives according to Formula I

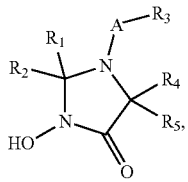

Formula I or pharmaceutically acceptable salts thereof, wherein,
$R^1$ is selected from the group consisting of:

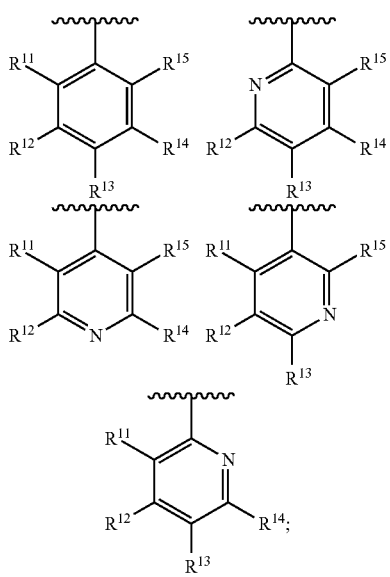

$R^{11}$ is H, halogen, (1-2C)alkyl or (1-2C)alkoxy, all alkyl and alkoxy groups optionally being substituted with one or more halogen;
$R^{12}$ is halogen, (1-2C)alkyl, (2-3C)alkenyl, (2-3C)alkynyl, (1-2C)alkoxy, (3-8C)cycloalkyl, cyano or nitro, all alkyl, alkoxy and cycloalkyl groups optionally being substituted with one or more halogen;
$R^{13}$ is H, halogen, (1-2C)alkyl or (1-2C)alkoxy, all alkyl and alkoxy groups optionally being substituted with one or more halogen;
$R^{14}$ is H, halogen, (1-2C)alkyl or (1-2C)alkoxy, all alkyl and alkoxy groups optionally being substituted with one or more halogen;
$R^{15}$ is H, halogen, (1-2C)alkyl or (1-2C)alkoxy, all alkyl and alkoxy groups optionally being substituted with one or more halogen.
$R^2$ is selected from the group consisting of:
a) hydrogen,
b) (1-6C)alkyl,
wherein (1-6C)alkyl optionally can be substituted,
$R^3$ is selected from the group consisting of:
a) (6-10C)aryl,
b) (1-9C)heteroaryl,
c) (3-8C)cycloalkyl,
d) (2-7C)heterocycloalkyl,
e) (1-6C)alkyl,
f) (1-6)alkylamino,
g) (3-6C)cycloalkylamino
h) (6-10C)arylamino,
i) (1-9C)heteroarylamino
j) (2-7C)heterocycloalkylamino
wherein all groups optionally can be substituted,
$R^4$ is selected from the group consisting of:
a) hydrogen,
b) (1-6C)alkyl,
wherein (1-6C)alkyl optionally can be substituted,
$R^5$ is selected from the group consisting of:
a) hydrogen,
b) (1-6C)alkyl,
wherein (1-6C)alkyl optionally can be substituted,
A is selected from CH($R^a$), C(O), S(O) or $SO_2$,
$R^a$ is selected from the group consisting of:
a) hydrogen,
b) (1-6C)alkyl,
wherein (1-6C)alkyl optionally can be substituted with fluorine or hydroxyl.

In an interesting embodiment, compounds according to Formula I which have been demonstrated to be IDO1 inhibitors with selectivity over TDO and/or CYP wherein $R^1$ is

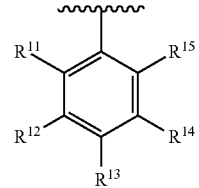

The terms as used herein refer to the following:
Halogen means fluorine, chlorine, bromine or iodine. Fluorine, chlorine or bromine are preferred halogens, fluorine or bromine being more preferred.
(1-2C)Alkyl means an alkyl group having 1 to 2 carbon atoms, being methyl or ethyl, methyl being preferred. A methyl group may be indicated as Me or $CH_3$.
(1-3C)Alkyl means a branched or unbranched alkyl group having 1-3 carbon atoms, being methyl, ethyl, propyl or isopropyl.
(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.
(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.
(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being more preferred.
(1-2C)Alkoxy means an alkoxy group having 1-2 carbon atoms, the alkyl moiety having the same meaning as previously defined. Methoxy groups are being preferred.
(1-3C)Alkoxy means an alkoxy group having 1-3 carbon atoms, the alkyl moiety having the same meaning as previously defined, (1-2C)alkoxy being preferred.
(2-3C)Alkenyl means a branched or unbranched alkenyl group having 2-3 carbon atoms, such as ethenyl or 2-propenyl.
(2-3C)Alkynyl means ethynyl or 2-propynyl.

(2-6C)Alkynyl means a branched or unbranched alkynyl group having 2-6 carbon atoms, for example ethynyl, propynyl, butynyl, 3-methylbut-1-yne and 3,3-dimethylbut-1-yne. (2-3C)alkynyl groups are preferred.

(3-8C)Cycloalkyl means a cycloalkyl group having 3-8 carbon atoms, being cyclopropyl, cyclobutyl, cyclopentyl, cyclohexyl, cycloheptyl or cyclooctyl. Preferred (3-8C)cycloalkyl groups are cyclohexyl, cyclopentyl or cyclobutyl, more preferred (3-8C)cycloalkyl groups are cyclopropyl and cyclohexyl.

(2-7C)Heterocycloalkyl means a heterocycloalkyl group having 2-7 carbon atoms, preferably 2-5 carbon atoms, and one or two heteroatoms selected from N, O and/or S. Preferred heteroatoms are N or O. Preferred (2-7C)heterocycloalkyl groups are azetidinyl, pyrrolidinyl, piperidinyl, piperazinyl, homopiperidinyl, morpholinyl or thiomorpholinyl, more preferred (2-7C)heterocycloalkyl groups are pyrrolidinyl and piperidyl The heterocycloalkyl group may be attached via a heteroatom if feasible.

(6-10C)Aryl means an aromatic hydrocarbon group having 6-10 carbon atoms, such as phenyl, naphthyl, tetrahydronaphthyl or indenyl. The preferred (6-10C)aryl group is phenyl.

(1-5C)Heteroaryl means a substituted or unsubstituted aromatic group having 5-6 ring atoms of which 1-5 carbon atoms and 1-4 heteroatoms selected from N, O and/or S. The (1-5C)heteroaryl may optionally be substituted. Examples of typical (1-5C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; Preferred (1-5C)heteroaryl groups are thienyl, isoxazolyl, pyrazolyl, pyridyl, pyrimidyl, pyrazinyl, more preferred (1-5C)heteroaryls are pyridinyl, pyrazolyl and thienyl.

(1-9C)Heteroaryl means a substituted or unsubstituted aromatic group having 8-10 atoms of which 1-9 carbon atoms and 1-5 heteroatoms selected from N, O and/or S. The (1-9C)heteroaryl may optionally be substituted. Examples of typical (1-9C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, isobenzofuranyl, chromenyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinolinyl, cinnolinyl, pteridinyl, isothiazolyl, and the like. (1-5C)Heteroaryl groups are being preferred.

(3-6C)Cycloalkylamino means an amino group, monosubstituted with an cycloalkyl group containing 3-6 carbon atoms having the same meaning as previously defined.

(1-6C)Alkylamino means an amino group, monosubstituted with an alkyl group containing 1-6 carbon atoms having the same meaning as previously defined.

(2-7C)Heterocycloalkylamino means an amino group, monosubstituted with a (2-7)heterocycloalkyl group containing 2-7 carbon atoms having the same meaning as previously defined.

(6-10C)Arylamino means an amino group, monosubstituted with a (6-10C)aryl group having the same meaning as previously described.

(1-9C)Heteroarylamino means an amino group, monosubstituted with a (1-9C)heteroaryl group having the same meaning as previously described.

(1-3C)Alkoxy(1-6C)alkyl means a (1-6C)alkyl group, substituted with a (1-3C)alkoxy group having the same meaning as previously described.

(1-3C)Alkoxy(1-6C)alkylamino means an amino group, monosubstituted with a (1-3C)alkoxy(1-6C)alkyl group having the same meaning as previously described.

(1-3C)Alkoxy(1-6C)alkylaminocarbonyl means a carbonyl group substituted with a (1-3C)alkoxy(1-6C)alkylamino group having the same meaning as previously described.

(1-6C)Alkylcarbonyl means a carbonyl group, substituted with a (1-6C)alkyl group having the same meaning as previously described.

(1-6C)Alkylcarbonylamino means an amino group, monosubstituted with a (1-6C)alkylcarbonyl group having the same meaning as previously described.

(1-6C)Alkylsulfonyl means a sulfonyl group, substituted with a (1-6C)alkyl group having the same meaning as previously described.

(1-6C)Alkylsulfonylamino means an amino group, monosubstituted with a (1-6C)alkylsulfonyl group having the same meaning as previously described.

(6-10C)Aryloxy means a (6-10C)aryl group, having the same meaning as previously described, attached via a ring carbon to an exocyclic oxygen.

(1-6C)Alkylsulfonylamino(1-6C)alkyl means a (1-6C)alkyl group, substituted with a (1-6C)alkylsulfonylamino group having the same meaning as previously described.

Aminosulfonylamino(1-6C)alkyl means a (1-6C)alkyl group, substituted with an aminosulfonylamino group.

(3-8C)Cycloalkyl(1-6C)alkyl means a (1-6C)alkyl group, substituted with a (3-8C)cycloalkyl group having the same meaning as previously described.

(1-6C)Alkylcarbonylamino(2-6C)alkynyl means a (2-6C)alkynyl group, substituted with a (1-6C)alkylcarbonylamino group having the same meaning as previously described.

Amino(2-6C)alkynyl means a (2-6C)alkynyl group, substituted with an amine.

Aminosulfonylamino(2-6C)alkynyl means a (2-6C)alkynyl group, substituted with an aminosulfonylamino group.

(3-8C)Cycloalkyl(2-3C)alkynyl means a (2-3C)alkynyl group, substituted with a (3-8C)cycloalkyl group having the same meaning as previously described.

(1-6C)Alkylsulfonylamino(2-6C)alkynyl means a (2-6C)alkynyl group, substituted with a (1-6C)alkylsulfonylamino group having the same meaning as previously described.

(6-10C)Aryl(1-6C)alkyl means a (1-6C)alkyl group, substituted with a (6-10C)aryl group having the same meaning as previously described.

(1-3C)Alkylsulfonyl means a sulfonyl group, substituted with a (1-3C)alkyl group having the same meaning as previously described.

(1-3C)Alkylsulfonyl(6-10C)aryl means a (6-10C)aryl group, substituted with a (1-3C)alkylsulfonyl group having the same meaning as previously described.

Di[(1-6C)alkyl]amino means an amino group, disubstituted with alkyl group(s) each independently containing 1-6 carbon atoms and having the same meaning as previously defined. Preferred di[(1-6C)alkyl]amino group is dimethylamino.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

"Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The compounds according to formula I of the present invention were found to inhibit IDO1 activity, which make them excellent candidates for use in the treatment or prevention of diseases, disorders and other pathological conditions associated with an increased L-tryptophan degradation.

In one embodiment, the invention relates to a compound according to Formula I, wherein $R^2$ is hydrogen.

In another embodiment, the invention relates to a compound according to Formula I, wherein A is C(O) or CH($R^a$), preferably wherein A is C(O) or CH($R^a$) wherein $R^a$ is selected from H, methyl or a methyl substituted with fluorine or hydroxyl.

In yet another embodiment, the invention relates to a compound according to Formula I, wherein $R^4$ and $R^5$ are selected from the group of hydrogen, methyl and ethyl, preferably from the group of hydrogen and methyl, with the provision that if one of $R^4$ or $R^5$ is not hydrogen, the other must be hydrogen. More preferably, $R^4$ and $R^5$ are hydrogen.

In again another embodiment, the invention relates to compounds according to Formula I, wherein $R^1$ is

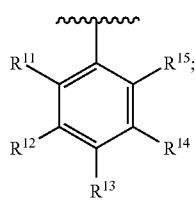

$R^{11}$ is H, halogen, (1-2C)alkyl or (1-2C)alkoxy, all alkyl and alkoxy groups optionally being substituted with one or more halogen; $R^{12}$ is halogen, (1-2C)alkyl, (2-3C)alkenyl, (2-3C)alkynyl, (1-2C)alkoxy, (3-8C)cycloalkyl, cyano or nitro, all alkyl, alkoxy and cycloalkyl groups optionally being substituted with one or more halogen; $R^{13}$ is H, halogen, (1-2C)alkyl or (1-2C)alkoxy, all alkyl and alkoxy groups optionally being substituted with one or more halogen; $R^{14}$ is H, halogen, (1-2C)alkyl or (1-2C)alkoxy, all alkyl and alkoxy groups optionally being substituted with one or more halogen; $R^{15}$ is H, halogen, (1-2C)alkyl or (1-2C)alkoxy, all alkyl and alkoxy groups optionally being substituted with one or more halogen.

In yet another embodiment the invention relates to a compound according to Formula I wherein $R^3$ is selected from the group consisting of: (6-10C)aryl, (1-9C)heteroaryl, (3-8C)cycloalkyl, (2-7C)heterocycloalkyl and (1-6C)alkyl, preferably (6-10C)aryl, (1-9C)heteroaryl and (3-8C)cycloalkyl, more preferably (6-10C)aryl, wherein all groups optionally can be substituted. Particularly preferred are compounds according to formula I wherein $R^3$ is

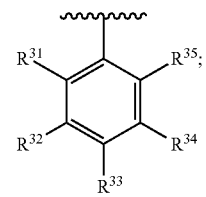

$R^{31}$ and $R^{35}$ are independently selected from the group consisting of: hydrogen, halogen, cyano, (1-2C)alkyl, (2-3C)alkenyl, (2-3C)alkynyl and (1-2C)alkoxy, all alkyl and alkoxy groups optionally being substituted with one or more halogen; $R^{32}$ and $R^{34}$ are independently selected from the group consisting of: hydrogen, halogen, cyano, (1-6C)alkyl, (2-3C)alkenyl, (2-3C)alkynyl, (1-2C)alkoxy, (1-3C)alkoxy(1-6C)alkylaminocarbonyl, amino, nitro, (1-6C)alkylcarbonylamino or (1-6C)alkylsulfonylamino, all alkyl and alkoxy groups optionally being substituted with one or more halogen; $R^{33}$ is selected from the group consisting of: hydrogen, halogen, cyano, (1-6C)alkyl, (2-3C)alkenyl, (2-6C)alkynyl, (1-3C)alkoxy, (6-10C)aryl, (1-5C)heteroaryl, (2-7C)heterocycloalkyl, (3-8C)cycloalkyl, (6-10C)aryloxy, (1-6C)alkylsulfonylamino(1-6C)alkyl, aminosulfonylamino(1-6C)alkyl, (3-8C)cycloalkyl(1-6C)alkyl, (1-6C)alkylcarbonylamino(2-6C)alkynyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, (6-10C)aryl(1-6C)alkyl, (1-3C)alkylsulfonyl(6-10C)aryl, di[(1-6C)alkyl]amino all alkyl and alkoxy groups optionally being substituted with one or more halogen or hydroxy, all (1-5C)heteroaryl groups optionally being substituted with one or more halogen or one or more (1-6C)alkyl. More preferably $R^{31}$ and $R^{35}$ are independently selected from the group consisting of: hydrogen, fluoro and chloro; $R^{32}$ and $R^{34}$ are hydrogen; $R^{33}$ hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino (2-6C)alkynyl, (1-3C)alkoxy(1-6C)alkylaminocarbonyl, di[(1-6C)alkyl]amino, all alkyl and alkoxy groups optionally being substituted with one or more halogen or hydroxy, all (1-5C)heteroaryl groups optionally being substituted with one or more halogen or one or more (1-6C)alkyl.

In a preferred embodiment, the invention provides for compounds according to Formula I which have been demonstrated to be IDO1 inhibitors with excellent selectivity over TDO and/or CYP, wherein $R^1$ is

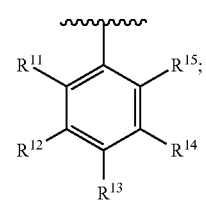

$R^{11}$, $R^{15}$, $R^{14}$ is H or fluorine, $R^{12}$ is halogen, nitro, (1-2C)alkyl, (2-3C)alkenyl or (2-3C)alkynyl, all alkyl groups optionally being substituted with one or more halogen, $R^{13}$ is H or halogen. Particularly preferred selective IDO1 inhibitors are those compounds according to Formula I wherein A is C(O) or CH($R^a$); $R^1$ is

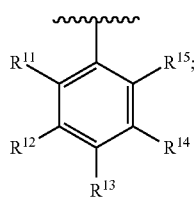

$R^{11}$, $R^{15}$, $R^{14}$ is H or fluorine, $R^{12}$ is halogen, nitro, (1-2C)alkyl, (2-3C)alkenyl or (2-3C)alkynyl, all alkyl groups optionally being substituted with one or more halogen, $R^{13}$ is H or halogen; $R^2$ is hydrogen; $R^4$ and $R^5$ are hydrogen or methyl, preferably hydrogen, with the provision that if one of $R^4$ or $R^5$ is not hydrogen, the other must be hydrogen.

In a more preferred embodiment, the invention provides for compounds according to formula I which are selective IDO1 inhibitors found to have excellent potency, wherein furthermore $R^3$ is

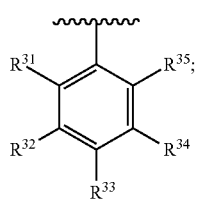

$R^{31}$ and $R^{35}$ are independently selected from the group consisting of: hydrogen, fluoro and chloro; $R^{32}$ and $R^{34}$ are hydrogen; $R^{33}$ hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino all alkyl and alkoxy groups optionally being substituted with one or more halogen or hydroxy, all (1-5C)heteroaryl groups optionally being substituted with one or more halogen or one or more (1-6C)alkyl. Even more selective IDO1 inhibitors with excellent potency have been found to be compounds according to Formula I, wherein $R^1$ is

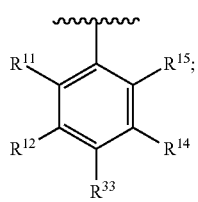

$R^{11}$, $R^{15}$, $R^{14}$ is H or fluorine, $R^{12}$ is halogen, nitro, (1-2C)alkyl, (2-3C)alkenyl or (2-3C)alkynyl, all alkyl groups optionally being substituted with one or more halogen, $R^{13}$ is H or halogen; $R^2$ is hydrogen; $R^4$ and $R^5$ are hydrogen or methyl, preferably hydrogen, with the provision that if one of $R^4$ or $R^5$ is not hydrogen, the other must be hydrogen; and $R^3$ is

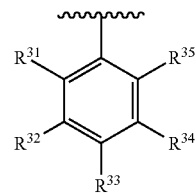

wherein $R^{31}$ and $R^{35}$ are independently selected from the group consisting of: hydrogen, fluoro and chloro; $R^{32}$ and $R^{34}$ are hydrogen; $R^{33}$ hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen hydroxy, all (1-5C)heteroaryl groups optionally being substituted with one or more halogen or one or more (1-6C)alkyl.

In a particularly interesting embodiment, the invention provides for compounds according to Formula I which have been demonstrated to be very potent IDO1 inhibitors with excellent selectivity over TDO and/or CYP, wherein A is C(O) or CH($R^a$); $R^1$ is

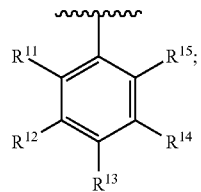

$R^{11}$, $R^{15}$, $R^{14}$ is H or fluorine, $R^{12}$ is halogen, nitro, (1-2C)alkyl, (2-3C)alkenyl or (2-3C)alkynyl, all alkyl groups optionally being substituted with one or more halogen, $R^{13}$ is H or halogen; $R^2$ is hydrogen; $R^4$ and $R^5$ are hydrogen or methyl, preferably hydrogen, with the provision that if one of $R^4$ or $R^5$ is not hydrogen, the other must be hydrogen; $R^3$ is

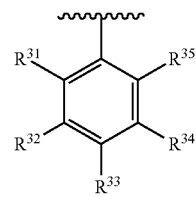

wherein $R^{31}$ and $R^{35}$ are independently selected from the group consisting of: hydrogen, fluoro and chloro; $R^{32}$ and $R^{34}$ are hydrogen; $R^{33}$ hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen or hydroxy, all (1-5C)heteroaryl groups optionally being substituted with one or more halogen or one or more (1-6C)alkyl; $R^4$ and $R^5$ are hydrogen.

The invention also provides for those compounds wherein all specific definitions of $R^1$-$R^5$, A, $R^a$, $R^{11-15}$ and $R^{31-35}$ and all substituent groups in the various aspects of the inventions defined here above occur in any combination within the definition of the compound of Formula I. Suitable compounds according to the invention are the compounds according to Formula I of examples 1 to 147. The compounds according to Formula I have an inhibitory potency on IDO1 with an $IC_{50}$ of 25 µM or lower, in particular 20 µM or less, more particular 10 µM or less. More preferably, the compounds according to Formula I have an inhibitory potency on IDO1 with an $IC_{50}$ of 5 µM or less, such as e.g. the compounds of examples 1, 2, 7, 8, 10, 14, 16, 17, 18, 20, 23, 24, 25, 28, 29, 30, 31, 38, 39, 40, 43, 47, 48, 50, 57, 60, 61, 63b, 64, 65, 69, 70, 74, 78, 88, 89, 90, 91, 96, 97, 99, 100, 101, 102, 103, 112, 113, 121, 123, 131, 134, 135, 140a, 142a and 143a. Particularly preferred are compounds according to Formula I which have an inhibitory potency on IDO1 with an $IC_{50}$ of 1 µM or less, such as e.g. the compounds of examples 3, 4, 9, 13, 15, 26, 27, 32, 33, 34, 35, 36, 37, 44, 45, 46, 51, 52, 53, 54, 59, 62, 63a, 66, 67, 71, 72, 73, 75, 76, 77, 82, 85, 86, 87, 98, 105, 106, 107, 108, 109, 110, 111, 114, 115, 116, 117, 118, 119, 120, 124, 125, 126, 127, 128, 129, 130, 132, 137, 138, 139b, 140b, 141b, 142b, 143b, 144a, 144b, 145a, 145b, 146a, 146b and 147b.

The term $IC_{50}$ means the concentration of the test compound that is required for 50% inhibition of its maximum effect in vitro.

Inhibition of IDO1 activity can be measured by determining the enzymatic conversion of L-tryptophan into N-formylkynurenine (NFK) in a reaction mixture containing IDO1 and test compound. The formation of NFK can be detected directly by, for instance, high-performance liquid chromatography (HPLC) methods, or by intrinsic fluorescence. The formation of NFK can also be measured by using a chemical probe that reacts with NFK to form a fluorescent product (Seegers, N. et al., J. Biomol. Screen. 19: 1266; 2014). Alternatively, the NFK formed in the reaction can be determined after a chemical reaction, i.e., NFK can be hydrolyzed to kynurenine, which can be measured by absorbance, fluorescence or HPLC methods (Matin, A., et al., Anal. Biochem. 349: 96; 2006).

The biological activity of IDO1 inhibitors can be measured by applying above detection methods to cells that are treated with test compound. The expression of IDO1 can be induced in many different cell lines by stimulation with IFNγ (Takikawa, O., et al., J. Biol. Chem. 263: 2041; 1988; Seegers, et al.), or IDO1 can be expressed in cells that lack endogenous IDO1 by transfection of an expression vector containing IDO1 cDNA.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I may contain both a basic moiety, such as, but not limited to a pyridine or imidazole, and an acidic moiety, zwitterions ("inner salts") may be formed and are included within the term "salt(s)" as used herein. Pharmaceutically acceptable (i.e., non-toxic, physiologically acceptable) salts are preferred. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, J. of Pharm. Sci. (1977) 66(1) 1-19; P. Gould, Int. J. Pharm. (1986) 33 201-21 7; Anderson et al, The Practice of Medicinal Chemistry (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization as discussed, for example, by M. Todd (ed.) *Separation of Enantiomers: Synthetic Methods,* 1$^{st}$ ed., Wiley-VCH (2014). Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of a chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds according to the invention.

The compounds having Formula I or the pharmaceutically accepted salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature.

Substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labeled reagent for a non-isotopically labeled reagent.

In a second aspect of the invention, the compounds according to Formula I or a pharmaceutically acceptable salt thereof can be used as a medicament in therapy. More in particular, the compounds according to Formula I or a pharmaceutically acceptable salt thereof can be used for the treatment of diseases or conditions caused by, or associated with increased activity of IDO1, in particular diseases or disorders caused by, or associated with increased tryptophan metabolism.

In particular, the compounds of Formula I or their salts, and pharmaceutical compositions thereof can be used to treat cancer.

In another embodiment, the compounds of the present invention, their salts and pharmaceutical compositions thereof can be used to increase the efficacy of one or more other anti-cancer agents, e.g., chemotherapeutic agents, vaccines, antibodies, or cell therapies.

In yet another embodiment, the compounds of the present invention, their salts and pharmaceutical compositions thereof can be used to treat infections with viruses or microorganisms.

In again another aspect, the compounds of the present invention, their salts and pharmaceutical compositions thereof can be used to treat or prevent the negative effects of cytokines on the central nervous system, which are related to increased activity of IDO1, in particular in which tryptophan metabolism plays a role, such as neuropsychiatric disease.

In yet again another embodiment, the compounds of the present invention, their salts and pharmaceutical compositions thereof can be used to treat or prevent the negative effects of cytokine therapy or other immune-based therapies on the central nervous system.

In a further embodiment, the compounds of the present invention, their salts and pharmaceutical compositions thereof can be used to treat or prevent the negative effects cytokines on IDO1 activity in metabolic disorders, such as diabetes or obesity.

In yet a further embodiment, the compounds of the present invention, their salts and pharmaceutical compositions thereof can be used to treat or prevent neurodegenerative disease, such as Parkinson's or Huntington's disease.

In another embodiment of the invention, the compounds of the present invention their salts and pharmaceutical compositions thereof can be used to treat immune-related disease and disorders.

A further aspect of the invention resides in the use of a compound of Formula 1, pharmaceutically acceptable salts and pharmaceutical compositions thereof in the treatment of diseases, disorders and pathological conditions caused by or associated with overexpression or over-activity of the IDO1 protein, in particular diseases, disorders and conditions wherein an increased tryptophan degradation plays a prominent role.

Included herein are methods of treatment and/or pharmaceutical compositions in which at least one compound of Formula I or a pharmaceutically acceptable salt thereof is administered a single agent or in combination with at least one other active agent. The other active agent can be a chemotherapeutic agent, an antibody, or an active polypeptide.

Thus, in one embodiment, the invention concerns a compound of Formula I or salt thereof in combination with one or more other drug(s).

In a third aspect, the invention further provides a pharmaceutical composition, which comprises a compound of Formula I and salts thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

Mixed with such pharmaceutically acceptable auxiliaries, e.g. as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as here in above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

The compound of the present invention can also be administered as a protein-drug conjugate. The compound can be covalently bound, optionally with a linker molecule to a peptide or protein, such as a binding protein for example an antibody. Using this approach, the conjugate can be delivered to the target tissue. Methods to prepare such conjugates are well known to those skilled in the art.

The compound of the present invention can also be administered as a (bio)polymeric nanoparticulate-drug system (Park, W. et al., Nanomed. Nanobiotechnol. 7: 494-508; 2015). The compound can be covalently bound, optionally with a linker molecule to the nanoparticulate system for example, but not limited to, a polymeric micelle. Using this approach, the nanoparticulate can be delivered to the target tissue. Methods to prepare such nanoparticulates are well known to those skilled in the art.

It will be appreciated that when the compound of the present invention is administered in combination with other therapeutic agents normally administered by the inhaled, intravenous, oral or intranasal route, that the resultant pharmaceutical composition may be administered by the same routes.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate IDO1 protein, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple sub-doses administered at appropriate intervals throughout the day, or, in case of female recipients, as doses to be administered at appropriate daily intervals throughout the menstrual cycle. The dosage, as well as the regimen of administration, may differ between a female and a male recipient.

The present invention also relates to a pharmaceutical composition comprising a compound of Formula I or pharmaceutically acceptable salt thereof in a mixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

For the treatment of cancer a compound of Formula I may be combined with one or more anticancer agents. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved.

The 3-hydroxyimidazolidin-4-one derivatives of the present invention can be prepared by methods well known in the art of organic chemistry. See, for example, J. March, '*Advanced Organic Chemistry*' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' $3^{rd}$ Edition, John Wiley and Sons, 1999. The protective groups are optionally removed at a convenient subsequent stage using methods well known in the art.

The products of the reactions are optionally isolated and purified, if desired, using conventional techniques, including but not limited to, filtration, distillation, crystallization, chromatography and the like. Such materials are optionally characterized using conventional means, including physical constants and spectral data.

3-Hydroxyimidazolidin-4-one compounds of Formula I, wherein $R^1$ to $R^5$ and A have the previously defined meanings, can be prepared by the general synthetic route shown in scheme I.

Scheme I

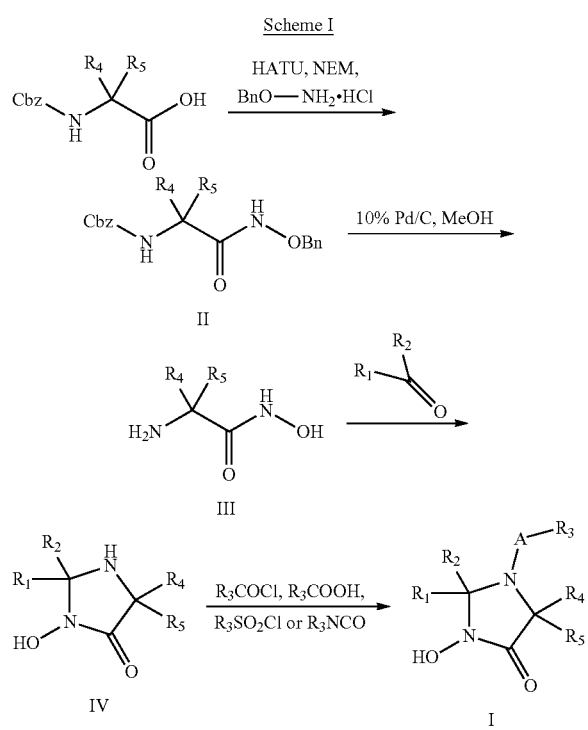

Substituted benzyl N-[2-(benzyloxyamino)-2-oxo-ethyl] carbamate (II) can be prepared from commercial available Cbz-protected amino acids and O-benzylhydroxylamine using an appropriate coupling reagent like HATU or EDCI-hydrochloride in a solvent such as DMF, dichloromethane or THF at appropriate temperature. Derivatives III can subsequently be prepared from derivatives II under catalytic hydrogenation conditions in the presence of a suitable palladium catalyst and solvent. Cyclisation towards derivatives IV can be accomplished by condensation reactions of derivatives III with aldehydes or ketones under heating conditions. Finally conversion of derivatives IV to compounds with formula I can be accomplished using methods well known in the art. The reagents $R_3$—COCl, $R_3$COOH, $R_3SO_2Cl$ or $R_3NCO$ are either commercially available or they can be readily prepared using methods known to skilled organic chemists.

Alternatively 3-hydroxyimidazolidin-4-one compounds of Formula I, wherein $R^1$ to $R^5$ and A have the previously defined meanings, can be prepared by the general synthetic route shown in scheme II.

Scheme II

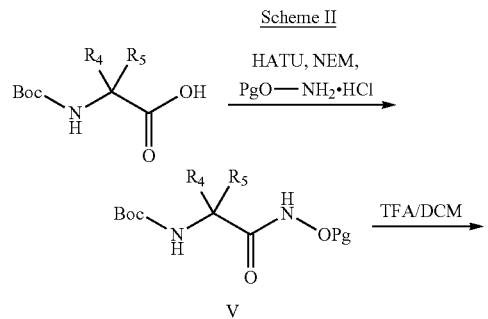

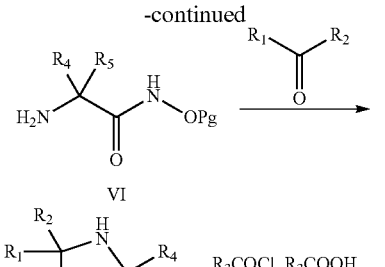

Commercially available Boc-protected amino acids can be converted into the corresponding O-benzyl protected hydroxamic acid derivatives V with an appropriate couplings reagent such as HATU or EDCI.hydrochloride and O-benzyl protected hydroxyl amine in a suitable solvent like DCM or DMF at appropriate temperature. Cleaving the protective group of derivatives V using TFA in dichloromethane give the unprotected amines VI which provided derivatives VII, after condensation with aldehydes or ketones in appropriate solvents such as DCM, acetonitrile or ethanol under heating conditions. Conversion of derivatives VII to compounds VIII can be accomplished using methods well known in the art. The reagents $R_3$—COCl, $R_3$COOH, $R_3SO_2Cl$ or $R_3NCO$ are either commercially available or they can be readily prepared using methods known to skilled organic chemists. Compounds of formula I can subsequently be prepared under catalytic hydrogenation conditions in the presence of a suitable palladium catalyst and solvent.

Separation of the enantiomeric 3-hydroxyimidazolidin-4-one compounds of Formula I, wherein $R^1$ to $R^5$ and A have the previously defined meanings, can be performed using chiral HPLC or prepared by the general synthetic route using chiral auxiliaries as shown in scheme III.

Scheme III

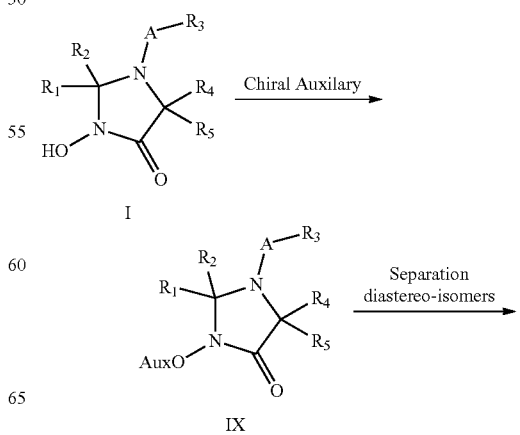

Chiral auxiliaries were reacted with compounds with formula I, to obtain derivatives IX by methods known to skilled organic chemists. Chiral acid chlorides such as (2R)-3,3,3-trifluoro-2-methoxy-2-phenylpropanoyl chloride (Mosher's acid chloride), (2S)-2-methoxy-2-phenyl-acetyl chloride or (2S)-2-phenylbutanoyl chloride or chiral alcohols such as (1S)-1-phenylethanol could be introduced and the thus obtained mixtures of diastereoisomers IX could be separated using chromatographic techniques such as chiral HPLC. After cleavage of the auxiliaries with suitable deprotection agents compounds of formula 1a and 1b could be isolated.

The invention is illustrated by the following examples.

EXAMPLES

The following examples are illustrative embodiments of the invention, not limiting the scope of the invention in any way. Reagents are either commercially available or are prepared according to procedures known in the literature.

Method LCMS (A)

| Method name | NTRC_C18_Short.M | |
|---|---|---|
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or ACN | |
| Injection volume | 1.0 μl | |
| Eluent | A | B |

| Time [min] | % 0.1% Formic Acid | % 0.05% Formic Acid in Acetonitrile |
|---|---|---|
| 0 | 90 | 10 |
| 0.3 | 90 | 10 |
| 7.0 | 10 | 90 |
| 7.1 | 90 | 10 |
| 10.0 | 90 | 10 |
| Post time | 0.2 min | Stop time | 10 min |

Method LCMS (B)

| Method LCMS (B) Method name | NTRC_C18.M | |
|---|---|---|
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or ACN | |
| Injection volume | 1.0 μl | |
| Eluent | A | B |

| Time [min] | % 0.1% Formic Acid | % 0.05% Formic Acid in Acetonitrile |
|---|---|---|
| 0 | 90 | 10 |
| 1 | 90 | 10 |
| 22.0 | 10 | 90 |
| 22.1 | 90 | 10 |
| 30.0 | 90 | 10 |
| Post time | 0.2 min | Stop time | 30 min |

Method Preparative HPLC

| LC System | Waters Prep System |
|---|---|
| Column | Phenomenex Luna, C18(2) 100 A, 150 mm × 21.2 mm, 5 μm |
| Column Temp | 20° C. |
| Sample(s) | 10-50 mg |
| Autosamp. Temp | 20° C. |
| Injection volume | 500-950 μL |
| Flow | 15 ml/min |
| Eluent | A = MilliQ + MeCN (9/1) B = Acetonitrile |

| | time (min) | % A | % B | % C |
|---|---|---|---|---|
| Gradient | 0 | 97 | 0 | 3 |
| | 20 | 37 | 60 | 3 |
| | 25 | 37 | 60 | 3 |
| | 25.1 | 97 | 0 | 3 |
| | 30 | 97 | 0 | 3 |
| UV detection | Photo Diode Array | | | |

The following abbreviations are used throughout the application with respect to chemical terminology:

HATU O-(7-Azabenzotriazol-1-yl)-1,1,3,3-tetramethyluroniumhexafluorophosphate
DCM Dichloromethane
EDCI.HCl N-(3-Dimethylaminopropyl)-N'-ethylcarbodiimide hydrochloride
NEM 4-Ethylmorpholine
DiPEA N,N-Diisopropylethylamine
Pd(OH)$_2$/C Palladium hydroxide on carbon (Pearlman's catalyst)
HPLC High Performance Liquid Chromatography
LCMS Liquid Chromatography with Mass Spectrometry detection
HCl Hydrogen chloride
NaHCO$_3$ Sodium bicarbonate
Boc tert-Butyloxycarbonyl
Cbz Benzyloxycarbonyl
DMSO Dimethyl sulfoxide
DMEM Dulbecco's Modified Eagle's Medium
TFA Trifluoroacetic acid
EtOAc Ethyl acetate
LiOH Lithium hydroxide
Na$_2$SO$_4$ Sodium sulfate
PdCl$_2$(dppf) [1,1'-Bis(diphenylphosphino)ferrocene]dichloropalladium(II)
Pd(PPh$_3$)$_4$ Tetrakis(triphenylphosphine)palladium(0)

BF$_3$.OEt Boron trifluoride diethyl etherate
DMF N,N-Dimethylformamide
NaH Sodium hydride
THF Tetrahydrofuran
MeOH Methanol The names of the final products in the examples are generated using Accelrys Draw (version 4.1).

Intermediate 1

2-Aminoethanehydroxamic Acid (a) Benzyl N-[2-(benzyloxyamino)-2-oxo-ethyl] carbamate To a cold solution (0° C.) of Cbz-Gly-OH (2.75 g, 13.2 mmol) and O-benzylhydroxylamine hydrochloride (2.1 g, 13.2 mmol) in ethyl acetate/DMF=5/1 v/v % (132 mL) was added DiPEA (6.53 mL, 39.5 mmol) and EDCI.HCl (2.57 g, 13.4 mmol), after which the reaction mixture was allowed to warm to room temperature and stirred for 3 days. After TLC indicated a complete conversion of starting material the mixture was added dropwise to a stirred solution of water/brine=1/1 v/v % (250 mL). After separation of the organic and the water layers, the water layer was extracted with ethyl acetate (2×150 mL). The combined organic layers were subsequently washed with a solution of 1N HCl (100 mL), water (100 mL), 5% sodium bicarbonate (100 mL), water and brine. The organic layer was subsequently dried over sodium sulfate and concentrated in vacuo to give 2.93 g of N-[2-(benzyloxyamino)-2-oxo-ethyl]carbamate (yield: 71%).

(b) 2-Aminoethanehydroxamic Acid

10% Palladium on charcoal (700 mg) was added to a suspension of benzyl N-[2-(benzyloxyamino)-2-oxo-ethyl] carbamate (7 g, 22.3 mmol) in methanol/ethyl acetate=3/1 v/v % (400 mL). The mixture was hydrogenated at atmospheric pressure at room temperature for 2 h. The palladium catalyst was removed by filtration and the solvent was removed by evaporation at reduced pressure. The residue was dissolved in water and lyophilized yielding 2-aminoethanehydroxamic acid (4.3 g, 77%) as a white powder.

Intermediate 2

3-Hydroxy-2-[3-(trifluoromethyl)phenyl]imidazolidin-4-one

2-Aminoethanehydroxamic acid (Intermediate 1, 130 mg, 1.43 mmol) and 3-(trifluoromethyl)benzaldehyde (273 mg, 1.57 mmol) were suspended in absolute ethanol (2.5 mL). The mixture was heated to reflux for 1 h to give a clear orange/yellow solution. The reaction mixture was cooled to room temperature and stirred overnight. The resulting turbid solution was subsequently concentrated in vacuo. The residue was dissolved in dichloromethane (2 mL) and heptane (4 mL) was added under vigorous stirring. The resulting precipitate was collected by decantation to give 198 mg of 3-hydroxy-2-[3-(trifluoromethyl)phenyl]imidazolidin-4-one as a light brown solid (yield: 56%).

Intermediate 3

3-(1-Hydroxy-5-oxo-imidazolidin-2-yl)benzonitrile

This compound was prepared in an analogous manner as described for Intermediate 2, starting from Intermediate 1 and 3-cyanobenzaldehyde to afford the title compound (173 mg, 59%).

Intermediate 4

2-[4-Chloro-3-(trifluoromethyl)phenyl]-3-hydroxy-imidazolidin-4-one

This compound was prepared in an analogous manner as described for Intermediate 2, starting from Intermediate 1 and 4-chloro-3-(trifluoromethyl)benzaldehyde to afford the title compound (202 mg, 50%).

Intermediate 5

2-(3-Fluorophenyl)-3-hydroxy-imidazolidin-4-one

This compound was prepared in an analogous manner as described for Intermediate 2, starting from Intermediate 1 and 3-fluorobenzaldehyde to afford the title compound (115 mg, 41%).

Intermediate 6

2-(3-Chlorophenyl)-3-hydroxy-imidazolidin-4-one

This compound was prepared in an analogous manner as described for Intermediate 2, starting from Intermediate 1 and 3-chlorobenzaldehyde to afford the title compound (245 mg, 80%).

Intermediate 7

2-(3-Bromophenyl)-3-hydroxy-imidazolidin-4-one

This compound was prepared in an analogous manner as described for Intermediate 2, starting from Intermediate 1 and 3-bromobenzaldehyde to afford the title compound (150 mg, 23%).

Intermediate 8

2-(3-Bromo-4-fluoro-phenyl)-3-hydroxy-imidazolidin-4-one

This compound was prepared in an analogous manner as described for Intermediate 2, starting from Intermediate 1 and 3-bromo-4-fluorobenzaldehyde to afford the title compound (333 mg, 47%).

Intermediate 9

2-(3-Chloro-4-fluoro-phenyl)-3-hydroxy-imidazolidin-4-one

This compound was prepared in an analogous manner as described for Intermediate 2, starting from Intermediate 1 and 3-chloro-4-fluorobenzaldehyde to afford the title compound (168 mg, 29%).

Intermediate 10

4-Ethynyl-2,6-difluoro-benzoic Acid (a) Methyl 4-bromo-2,6-difluoro-benzoate

Thionylchloride (6.12 mL, 84.4 mmol) was added dropwise to dry methanol (100 mL) at −20° C. 4-Bromo-2,6-difluorobenzoic acid (10 g, 42.2 mmol)) was added and the reaction mixture was heated under reflux o/n. The mixture was concentrated in vacuo and traces of hydrochloric acid were co-evaporated with methanol (3 times). The residue crystallized upon standing giving 11.8 g of the title compound.

(b) Methyl 2,6-difluoro-4-(2-trimethylsilylethynyl)benzoate

4-Bromo-2,6-difluoro-benzoic acid methyl ester (250 mg, 1 mmol) was dissolved in triethylamine (5 mL) and to this solution dichloropalladium(bis)triphenylphosphine (36 mg, 0.05 mmol) was added followed by copper iodide (10 mg, 0.05 mmol) and trimethylsilylacetylene (170 µL, 1.2 mmol). The reaction mixture was heated for 1 hour at 100° C. under microwave radiation. The mixture was cooled to room temperature and filtered through Decalite™ and concentrated under reduced pressure. The crude residue was purified by column chromatography (heptane to ethyl acetate=9/1 v/v %) to afford 293.6 mg of the title compound (quantitative yield).

(c) 4-Ethynyl-2,6-difluoro-benzoic Acid (Intermediate 10)

Methyl 2,6-difluoro-4-(2-trimethylsilylethynyl)benzoate (293.6 mg, 1.09 mmol) was dissolved in methanol (5 mL) and 5 mL of a 2M LiOH-solution in water. The mixture was refluxed overnight, after which methanol was removed by concentration in vacuo and the resulting solution was extracted with EtOAc, acidified, and again extracted with EtOAc. The organic layers were washed with brine, dried ($Na_2SO_4$), filtered and concentrated under vacuum to give the title compound (154.7 mg, 77.9%).

Intermediate 11

4-(2-Cyclopropylethynyl)-2,6-difluoro-benzoic Acid (a) Methyl 4-(2-cyclopropylethynyl)-2,6-difluoro-benzoate 4-Bromo-2,6-difluoro-benzoic acid methyl ester (250 mg, 1 mmol) was dissolved in triethylamine (5 mL) and dichloropalladium(bis)triphenylphosphine (36 mg, 0.05 mmol) was added followed by copper iodide (10 mg, 0.05 mmol) and cyclopropylacetylene (85 µL, 1.2 mmol). The reaction mixture was heated for 1 hour at 100° C. under microwave radiation. The mixture was cooled to room temperature and filtered through Decalite™ and concentrated under reduced pressure. The crude residue was purified by column chromatography (heptane to ethyl acetate=9/1 v/v %) to afford 214 mg of the title compound (yield: 90.6%).

(b) 4-(2-Cyclopropylethynyl)-2,6-difluoro-benzoic Acid (Intermediate 11)

Methyl 4-(2-cyclopropylethynyl)-2,6-difluoro-benzoate (214 mg, 0.91 mmol) was dissolved in methanol (5 mL) and 5 mL of a 2M LiOH-solution in water and the mixture was refluxed overnight. Methanol was removed by concentration in vacuo and the resulting solution was extracted with EtOAc, acidified, and again extracted with EtOAc. The organic layers were washed with brine, dried ($Na_2SO_4$), filtered and concentrated under vacuum to give the title compound (193.5 mg, 96.0%).

Intermediate 12

2,6-Difluoro-4-(3-methylbut-1-ynyl)benzoic Acid (a) Methyl 2,6-difluoro-4-(3-methylbut-1-ynyl)benzoate 4-Bromo-2,6-difluoro-benzoic acid methyl ester (502 mg, 2 mmol) was dissolved in triethylamine (10 mL) and dichloropalladium(bis)triphenylphosphine (70.2 mg, 0.1 mmol) was added followed by copper iodide (19 mg, 0.1 mmol) and 3-methyl-1-butyne (307 µL, 1.5 mmol). The reaction mixture was heated for 1 hour at 100° C. under microwave radiation. The mixture was cooled to room temperature and filtered through Celite® and concentrated in vacuo. The crude residue was purified by column chromatography (heptane to ethyl acetate=100/0 to 9/1 v/v %) to afford 440 mg of the title compound (yield: 92.4%).

(b) 2,6-Difluoro-4-(3-methylbut-1-ynyl)benzoic Acid (Intermediate 12)

Methyl 2,6-difluoro-4-(3-methylbut-1-ynyl)benzoate (440 mg, 1.85 mmol) was dissolved in 5 mL of methanol and 5 mL of a 2M LiOH-solution in water. The mixture was stirred at room temperature for 2 h, after which the reaction mixture was acidified, and extracted with dichloromethane. The organic layer was washed with brine, dried ($Na_2SO_4$), filtered over an PE-filter and concentrated in vacuo to give the title compound (367.8 mg, 88.7%).

Intermediate 13

4-(2-Cyclohexylethynyl)-2,6-difluoro-benzoic Acid (a) Methyl 4-(2-cyclohexylethynyl)-2,6-difluoro-benzoate Methyl 4-bromo-2,6-difluoro-benzoate (502 mg, 2 mmol) was dissolved in N,N-dimethylformamide (5 mL) and triethylamine (1.59 mL, 10 mmol). The solution was purged with nitrogen for 5 min and copper(I)iodide (19 mg, 0.1 mmol) and bis(triphenylphosphine)palladium(II)chloride (70.2 mg, 0.1 mmol) were added. The mixture was stirred for 5 min after which cyclohexylacetylene (1.29 mL, 10 mmol) was added and the reaction mixture was stirred at 80° C. for 2 h. The reaction mixture was added to a stirred mixture of water/brine/ethyl acetate=1/1/1 v/v % (45 mL). The organic layer was separated, washed with water, brine, dried over sodium sulfate, filtered and concentrated under reduced pressure. The crude residue was purified by column chromatography (heptane/ethyl acetate=95/5 v/v %) to afford 360 mg of the title compound (yield: 64.7%).

(b) 4-(2-Cyclohexylethynyl)-2,6-difluoro-benzoic Acid (Intermediate 13)

Methyl 4-(2-cyclohexylethynyl)-2,6-difluoro-benzoate (360 mg, 1.29 mmol) was dissolved in methanol (5 mL) and

Intermediate 14

4-[3-(tert-Butoxycarbonylamino)prop-1-ynyl]-2,6-difluoro-benzoic Acid

This compound was prepared in an analogous manner as described for Intermediate 13, starting from methyl 4-bromo-2,6-difluoro-benzoate (Intermediate 10a) and tert-butyl N-prop-2-ynylcarbamate to afford the title compound (185.3 mg, 97.6%).

Intermediate 15

2,6-Difluoro-4-[3-(methanesulfonamido)prop-1-ynyl]benzoic Acid

(a) N-prop-2-ynylmethanesulfonamide

To a cold (4° C.) solution of propargylamine (0.86 g, 15.6 mmol) and triethylamine (2.39 mL, 17.2 mmol) in dichloromethane (10 mL) was added dropwise a solution of methanesulfonyl chloride (1.52 mL, 15.6 mmol) in dichloromethane (5 mL). The reaction mixture was allowed to warm to room temperature, stirred for 1 h. and concentrated in vacuo. The crude residue was purified by column chromatography (heptane to ethyl acetate=8/2 to 1/1 v/v %) to afford 465 mg of the title compound (yield: 22.4%).

(b) 2,6-Difluoro-4-[3-(methanesulfonamido)prop-1-ynyl]benzoic Acid (Intermediate 15)

This compound was prepared in an analogous manner as described for Intermediate 13, starting from methyl 4-bromo-2,6-difluoro-benzoate (Intermediate 10a) and N-prop-2-ynylmethanesulfonamide to afford the title compound (187.7 mg, 57.9%).

Intermediate 16

4-[3-(tert-Butoxycarbonylsulfamoylamino)prop-1-ynyl]-2,6-difluoro-benzoic Acid

(a) tert-Butyl N-(prop-2-ynylsulfamoyl)carbamate

To a cold (4° C.) solution of chlorosulfonyl isocyanate (1.63 mL, 18.7 mmol) in dichloromethane (10 mL) was added dropwise a solution of tert-butanol 2.24 mL, 23.4 mmol) in dichloromethane (5 mL). The reaction mixture was stirred for 15 min at 5° C. Triethylamine (4.78 mL, 34.4 mmol) and propargylamine (1 mL, 15.6 mmol) were added subsequently to the reaction mixture and the mixture was allowed to warm to room temperature and stirred for 1 h. and subsequently concentrated in vacuo. The crude residue was purified by column chromatography (heptane to ethyl acetate=8/2 to 1/1 v/v %) to afford 2.79 g of the title compound (yield: 76.3%).

(b) 4-[3-(tert-butoxycarbonylsulfamoylamino)prop-1-ynyl]-2,6-difluoro-benzoic Acid (Intermediate 16)

This compound was prepared in an analogous manner as described for Intermediate 13, starting from methyl 4-bromo-2,6-difluoro-benzoate (Intermediate 10a) and tert-butyl N-(prop-2-ynylsulfamoyl)carbamate to afford the title compound (219.6 mg, 59.8%).

Intermediate 17

4-[3-(tert-Butoxycarbonylamino)-3-methyl-but-1-ynyl]-2,6-difluoro-benzoic Acid

(a) tert-Butyl N-(1,1-dimethylprop-2-ynyl)carbamate

A mixture of 2-methyl-3-butyn-2-amine (1 mL) and di-tert-butyl dicarbonate (2.07 g) without solvent was warmed up to 50° C. for 30 min. The resulting solution was diluted with n-hexane (5 mL) and the crystals formed were, subsequently, collected by filtration, washed with hexane and dried under vacuum to give 620 mg of the title compound (yield: 35.6%).

(b) 4-[3-(tert-Butoxycarbonylamino)-3-methyl-but-1-ynyl]-2,6-difluoro-benzoic Acid (Intermediate 17)

This compound was prepared in an analogous manner as described for Intermediate 13, starting from methyl 4-bromo-2,6-difluoro-benzoate (Intermediate 10a) and tert-butyl N-(1,1-dimethylprop-2-ynyl)carbamate to afford the title compound (608.4 mg, 93.4%).

Intermediate 18

4-Cyclopropyl-2,6-difluoro-benzoic Acid

(a) Methyl 4-cyclopropyl-2,6-difluoro-benzoate

Methyl 4-bromo-2,6-difluoro-benzoate (502 mg, 2 mmol), tricyclohexylphosphine (168 mg, 0.6 mmol), cesium carbonate (3.9 g, 12 mmol) and cyclopropylboronic acid methyliminodiacetic acid anhydride (552 mg, 2.8 mmol) were dissolved in toluene/water=5/1 v/v % (24 mL) and the solution was degassed with nitrogen for 5 minutes. Palladium(II)acetate (67.3 mg, 0.3 mmol) was added under nitrogen atmosphere and the reaction mixture was refluxed at 100° C. for 3 hours. The crude reaction mixture was filtered over Decalite™. The filtrate was diluted with ethyl acetate and washed with water, brine, dried over sodium sulfate, filtered and concentrated under reduced pressure. The crude residue was purified by column chromatography (heptane/ethyl acetate=95/5 v/v %) to afford the title compound (240 mg, yield: 56.6%).

(b) 4-Cyclopropyl-2,6-difluoro-benzoic Acid (Intermediate 18)

Methyl 4-cyclopropyl-2,6-difluoro-benzoate (240 mg, 1.13 mmol) was dissolved in methanol (5 mL) and 2M LiOH-solution in water (5 mL) and the mixture was stirred at room temperature for 2 h, after which the reaction mixture was acidified, and extracted with dichloromethane. The organic layer was washed with brine, dried ($Na_2SO_4$), filtered over an PE-filter and concentrated under vacuum to give the title compound (200 mg, 89.3%).

Intermediate 19

2,6-Difluoro-4-vinyl-benzoic Acid (a) Methyl 2,6-difluoro-4-vinyl-benzoate

Methyl 4-bromo-2,6-difluoro-benzoate (251 mg, 1.0 mmol) was dissolved in dioxane (5 mL) and potassium carbonate (207 mg, 1.5 mmol) was added. The solution was purged with nitrogen for 5 min and vinylboronic anhydride pyridine complex (240.7 mg, 1.0 mmol) and $PdCl_2$ (dppf).$CH_2Cl_2$ (40.8 mg, 0.05 mmol) were added. The reaction mixture was stirred for 2 h. at 100° C. The reaction mixture was added to a stirred mixture of 5% citric acid solution/brine/ethyl acetate=1/1/1 v/v % (150 mL). The organic layer was separated, washed with water, brine, dried over sodium sulfate, filtered and concentrated under reduced pressure The crude residue was purified by column chromatography (dichloromethane/methanol=98/2 v/v %) to afford two batches of the title compound (174 mg, yield: 87.7%).

(b) 2,6-Difluoro-4-vinyl-benzoic Acid (Intermediate 19)

This compound was prepared in an analogous manner as described for Intermediate 18b, starting from methyl 2,6-difluoro-4-vinyl-benzoate to afford the title compound (140.4 mg, 86.7%).

Intermediate 20

2,6-Difluoro-4-methyl-benzoic Acid

This compound was prepared in an analogous manner as described for Intermediate 19, starting from methyl 4-bromo-2,6-difluoro-benzoate (Intermediate 10a) and trimethylboroxine to afford the title compound (468 mg, 84.2%).

Intermediate 21

2,6-Difluoro-4-phenyl-benzoic Acid

Methyl 4-bromo-2,6-difluoro-benzoate (300 mg, 1.2 mmol) was dissolved in dioxane/water=4/1 v/v % (10 mL) and sodium carbonate (382 mg, 3.6 mmol) was added. The solution was purged with nitrogen for 5 min and phenylboronic acid (161 mg, 1.3 mmol) and $Pd(PPh_3)_4$ (69 mg, 0.06 mmol) were added. The reaction mixture was stirred for 1 h at 100° C. under microwave radiation. The reaction mixture was cooled and a 2M NaOH-solution in water was added (4 mmol). The mixture was stirred for 1 h at 50° C. Ethyl acetate (10 mL) was added and the aqueous layer was separated. The organic layer was extracted twice with 2N NaOH-solution in water. The pH of the water layers was adjusted to pH<2 and the acidic water layer was extracted with ethyl acetate. The ethyl acetate layers were collected and washed with brine, dried over sodium sulfate, filtered and concentrated in vacuo. The crude product was triturated with heptane/ethyl acetate=7/3 v/v %. White solids formed were collected by filtration, washed with heptane and dried under vacuum to give 108 mg of the title compound (yield: 38%).

Intermediate 22

2,6-Difluoro-4-(4-pyridyl)benzoic Acid

This compound was prepared in an analogous manner as described for Intermediate 21, starting from methyl 4-bromo-2,6-difluoro-benzoate (Intermediate 10a) and 4-(4,4,5,5-tetramethyl-1,3,2-dioxaborolan-2-yl)pyridine to afford 165 mg of the title compound.

Intermediate 23

2,6-Difluoro-4-(1-methylpyrazol-4-yl)benzoic Acid

This compound was prepared in an analogous manner as described for Intermediate 21, starting from methyl 4-bromo-2,6-difluoro-benzoate (Intermediate 10a) and 1-methyl-4-(4,4,5,5-tetramethyl-1,3,2-dioxaborolan-2-yl)-1H-pyrazole to afford 86 mg of the title compound (yield: 60%).

Intermediate 24

2,6-Difluoro-4-(2-thienyl)benzoic Acid

This compound was prepared in an analogous manner as described for Intermediate 21, starting from methyl 4-bromo-2,6-difluoro-benzoate (Intermediate 10a) and 2-(4,4,5,5-tetramethyl-1,3,2-dioxaborolan-2-yl)thiophene to afford 74 mg of the title compound (yield: 51%).

Intermediate 25

2,6-Difluoro-4-(5-fluoro-2-thienyl)benzoic Acid

This compound was prepared in an analogous manner as described for Intermediate 21, starting from methyl 4-bromo-2,6-difluoro-benzoate (Intermediate 10a) and 2-(5-fluoro-2-thienyl)-4,4,5,5-tetramethyl-1,3,2-dioxaborolane to afford 69 mg of the title compound (yield: 55%).

Intermediate 26

2,6-Difluoro-4-(1,3,5-trimethylpyrazol-4-yl)benzoic Acid

This compound was prepared in an analogous manner as described for Intermediate 21, starting from methyl 4-bromo-2,6-difluoro-benzoate (Intermediate 10a) and 1,3,5-trimethyl-1H-pyrazole-4-boronic acid pinacol ester to afford 87 mg of the title compound (yield: 54%).

Intermediate 27

2,6-Difluoro-4-(3-pyridyl)benzoic Acid

This compound was prepared in an analogous manner as described for Intermediate 21, starting from methyl 4-bromo-2,6-difluoro-benzoate (Intermediate 10a) and pyridine-3-boronic acid 1,3-propanediol cyclic ester to afford 65 mg of the title compound (yield: 34%).

Intermediate 28

4-[3-(tert-Butoxycarbonylsulfamoylamino)-3-methyl-but-1-ynyl]-2,6-difluoro-benzoic Acid This compound was prepared in an analogous manner as described for Intermediate 13 and Intermediate 16, starting from methyl 4-bromo-2,6-difluoro-benzoate (Intermediate 10a) and tert-butyl N-(1,1-dimethylprop-2-ynylsulfamoyl)carbamate to afford the title compound (221 mg, 76.7%).

Intermediate 29

3-Hydroxy-2-(3-vinylphenyl)imidazolidin-4-one

(a) 3-Vinylbenzaldehyde

3-Bromobenzaldehyde (185 mg, 1.0 mmol) was suspended in dioxane (2 mL) and potassium carbonate (207 mg, 1.5 mmol) was added. The solution was purged with nitrogen for 5 min and vinylboronic anhydride pyridine complex (240.7 mg, 1.0 mmol) and $PdCl_2(dppf).CH_2Cl_2$ (40.8 mg, 0.05 mmol) were added. The reaction mixture was stirred for 2 h. at 100° C. The reaction mixture was added to a stirred mixture of 5% citric acid solution/brine/ethyl acetate=1/1/1 v/v % (30 mL). The organic layer was separated, washed with water, brine, dried over sodium sulfate, filtered and concentrated under reduced pressure The crude residue was purified by column chromatography (heptane to ethyl acetate=10/0 to 1/1 v/v %) to afford the title compound (91 mg, yield: 69%).

(b) 3-Hydroxy-2-(3-vinylphenyl)imidazolidin-4-one

This compound was prepared in an analogous manner as described for Intermediate 2, starting from Intermediate 1 and 3-vinylbenzaldehyde to afford the title compound (90 mg, 64%).

Intermediate 30

2,6-Difluoro-4-(methanesulfonamidomethyl)benzoic Acid

(a) tert-Butyl 4-bromo-2,6-difluoro-benzoate

4-Bromo-2,6-difluorobenzoic acid (1.5 g, 6.33 mmol) was suspended in dichloromethane (10 mL). A solution of tert-butyl 2,2,2-trichloroacetamidate (1.38 g, 6.33 mmol) in cyclohexane (30 mL) and $BF_3.Et_2O$ (47.5 µL, 0.38 mmol) were added subsequently to the suspension. After stirring at room temperature for 16 h, the reaction was cooled on an ice bath and solid $NaHCO_3$ (0.5 g) was added in one portion. This mixture was stirred for 10 min and filtered over a silica plug. The filtrate was concentrated in vacuo and the residue was purified by column chromatography (heptane/ethyl acetate=7/3 v/v %) to provide the title compound as a colourless oil (1.43 g, 77.1%).

(b) tert-Butyl 4-cyano-2,6-difluoro-benzoate

To a solution of tert-butyl 4-bromo-2,6-difluoro-benzoate (1.4 g, 4.78 mmol) in DMF (10 mL) were added zinc cyanide (561 mg, 4.78 mmol), and $Pd(PPh_3)_4$ (552 mg, 0.48 mmol). The reaction mixture was refluxed at 80° C. under nitrogen atmosphere o/n. The reaction mixture was added to a stirred mixture of 5% $NaHCO_3$-solution/brine/ethyl acetate=1/1/1 v/v % (150 ml). The organic layer was separated, washed with water, brine, dried over sodium sulfate, filtered and concentrated under reduced pressure. The crude residue was purified by column chromatography (heptane/ethyl acetate=100/0 to 95/5 v/v %) to afford 810 mg of the title compound (yield: 70.8%).

(c) tert-Butyl 4-(aminomethyl)-2,6-difluoro-benzoate hydrochloride

10% Palladium on charcoal (20 mg) and 420 µL of a 2N hydrochloride solution were added to a solution of tert-butyl 4-cyano-2,6-difluoro-benzoate (200 mg, 0.84 mmol) in ethanol (20 mL). The mixture was hydrogenated at atmospheric pressure at room temperature for 3 h. The palladium catalyst was removed by filtration and the solvent was removed by evaporation at reduced pressure yielding tert-butyl 4-(aminomethyl)-2,6-difluoro-benzoate hydrochloride quantitatively.

(d) tert-Butyl 2,6-difluoro-4-(methanesulfonamidomethyl)benzoate

To a suspension of tert-butyl 4-(aminomethyl)-2,6-difluoro-benzoate hydrochloride (200 mg, 0.84 mmol) in DCM (10 mL) was added triethylamine (240 µL, 1.68 mmol) and methanesulfonyl chloride (65 µL, 0.84 mmol). The mixture was stirred at room temperature o/n. Mixture was concentrated under reduced pressure and the crude residue was purified by column chromatography (dichloromethane/methanol=98/2 to 96/4 v/v %) to afford 113.7 mg of the title compound (yield: 42.1%).

(e) 2,6-Difluoro-4-(methanesulfonamidomethyl)benzoic Acid (Intermediate 30)

To a solution of 2,6-difluoro-4-(methanesulfonamidomethyl)benzoic acid (113.7 mg, 0.35 mmol) in dichloromethane (2 mL) was added trifluoroacetic acid (2 mL). The reaction mixture was stirred at room temperature for 4 h. The mixture was concentrated in vacuo and co-evaporated with dichloromethane (3×) to give the title compound in quantitative crude yield.

Intermediate 31

4-(2-Cyclohexylethyl)-2,6-difluoro-benzoic Acid

10% Palladium on charcoal (20 mg) was added to a solution of 4-(2-cyclohexylethynyl)-2,6-difluoro-benzoic acid (125 mg, 0.47 mmol) in methanol (10 mL). The mixture was hydrogenated at atmospheric pressure at room temperature for 5 h. The palladium catalyst was removed by filtration and the solvent was removed by evaporation at reduced pressure yielding 4-(2-cyclohexylethyl)-2,6-difluoro-benzoic acid quantitatively.

Intermediate 32

4-[3-(tert-Butoxycarbonylsulfamoylamino)propyl]-2,6-difluoro-benzoic Acid

(a) Methyl 4-[3-(tert-butoxycarbonylsulfamoylamino)propyl]-2,6-difluoro-benzoate 10% Palladium on charcoal (30 mg) was added to a solution of methyl 4-[3-(tert-butoxycarbonylsulfamoylamino)prop-1-ynyl]-2,6-difluoro-benzoate (Intermediate 16b, 300 mg, 0.74 mmol) in methanol (10 mL). The mixture was hydrogenated at atmospheric pressure at room temperature for 5 h. The palladium catalyst was removed by filtration and the solvent was removed by evaporation at reduced pressure to give 273.1 mg of methyl 4-[3-(tert-butoxycarbonylsulfamoylamino)propyl]-2,6-difluoro-benzoate (yield: 90.4%).

(b) 4-[3-(tert-Butoxycarbonylsulfamoylamino)propyl]-2,6-difluoro-benzoic Acid (Intermediate 32)

Methyl 4-[3-(tert-butoxycarbonylsulfamoylamino)propyl]-2,6-difluoro-benzoate (273.1 mg, 0.69 mmol) was dissolved in methanol (5 mL) and 2M LiOH-solution (3.3 ml) and the mixture was stirred at room temperature for 2 h. The basic layer acidified, and extracted with dichloromethane. The organic layer was washed with brine, dried ($Na_2SO_4$), filtered over an PE-filter and concentrated in vacuo to give the title compound (223.2 mg, 82.1%).

Intermediate 33

2,6-Difluoro-4-morpholino-benzoic Acid (a) Methyl 2,6-difluoro-4-morpholino-benzoate To a solution of methyl 2,4,6-trifluorobenzoate (272 µL, 2 mmol) and morpholine (176 µL, 2 mmol) in DMSO (6 mL) was added potassium carbonate (331 mg, 2.4 mmol) and the reaction mixture was stirred at 55° C. for 1 h. Ethyl acetate was added to the mixture and the mixture was washed with water, brine, dried over sodium sulfate, filtered and the solvent was removed by evaporation at reduced pressure. The crude residue was purified by column chromatography (heptane/ethyl acetate=10/0 to 1/1 v/v %) to afford 191 mg of the title compound (yield: 22%).

(b) 2,6-Difluoro-4-morpholino-benzoic Acid (Intermediate 33)

This compound was prepared in an analogous manner as described for Intermediate 32b, starting with methyl 2,6-difluoro-4-morpholino-benzoate to afford the title compound (173 mg, 96%).

Intermediate 34

4-(Azetidin-1-yl)-2,6-difluoro-benzoic Acid

This compound was prepared in an analogous manner as described for Intermediate 33, starting with methyl 2,4,6-trifluorobenzoate and azetidine to afford the title compound (188 mg, 84%).

Intermediate 35

4-[2-Benzyloxyethyl(methyl)amino]-2,6-difluoro-benzoic Acid (a) Methyl 2,6-difluoro-4-[2-hydroxyethyl(methyl)amino]benzoate This compound was prepared in an analogous manner as described for Intermediate 33, starting with methyl 2,4,6-trifluorobenzoate and 2-(methylamino)ethanol to afford the title compound (160 mg, 33%).

(b) Methyl 4-[2-benzyloxyethyl(methyl)amino]-2,6-difluoro-benzoate

To a cold (0° C.) solution of methyl 2,6-difluoro-4-[2-hydroxyethyl(methyl)amino]-benzoate (160 mg, 0.65 mmol) in DMF (3 mL) was added NaH (60% dispersion in mineral oil, 26 mg, 0.65 mmol) and the reaction mixture was stirred for 10 min at 0° C. Then a solution of benzylbromide (77 µL, 0.65 mmol) in DMF (0.5 ml) was added and the mixture was stirred for 1 h allowing the temperature to come to room temperature. The reaction mixture was added to a stirred mixture of water/brine/ethyl acetate=1/1/1 v/v % (30 ml). The organic layer was separated, washed with water, brine, dried over sodium sulfate, filtered and concentrated under reduced pressure. The crude residue was purified by column chromatography (heptane/ethyl acetate=10/0 to 0/10 v/v %) to afford 126 mg of the title compound (yield: 58%).

(c) 4-[2-Benzyloxyethyl(methyl)amino]-2,6-difluoro-benzoic Acid (Intermediate 35)

This compound was prepared in an analogous manner as described for Intermediate 32b, starting with methyl 4-[2-benzyloxyethyl(methyl)amino]-2,6-difluoro-benzoate to afford the title compound (118 mg, 97%).

Intermediate 36

2,6-Difluoro-4-[(2S)-2-(hydroxymethyl)pyrrolidin-1-yl]benzoic Acid

This compound was prepared in an analogous manner as described for Intermediate 33, starting with methyl 2,4,6-trifluorobenzoate and L-prolinol to afford the title compound (50 mg, 29%).

Intermediate 37

2,6-Difluoro-4-(2-methoxyethylcarbamoyl)benzoic Acid (a) 4-tert-Butoxycarbonyl-3,5-difluoro-benzoic Acid To a cold (−78° C.) solution of tert-butyl 4-bromo-2,6-difluoro-benzoate (Intermediate 30a, 820 mg, 2.80 mmol) in THF (24 mL) was added drop-wise n-butyllithium (1.6M solution in hexane, 1.92 mL, 3.1 mmol). The reaction mixture turned into a red solution and after stirring for an additional 5 minutes at −78° C. solid crushed $CO_2$ (large excess) was added. The mixture was warmed to room temperature. The mixture was quenched by adding water (30 mL). The biphasic system was stirred thoroughly for 15 minutes at room temperature. The layers were separated and the organic layer was extracted with water (10 mL). The combined water layers were washed with ethyl acetate (20 mL) and acidified by addition of 2N HCl-solution (4 mL). The water layer was extracted with ethyl acetate (2×20 mL). The combined organic layers were washed with brine, dried ($Na_2SO_4$), filtered and concentrated to give 450 mg of 4-tert-butoxycarbonyl-3,5-difluoro-benzoic acid.

(b) tert-Butyl 2,6-difluoro-4-(2-methoxyethylcarbamoyl)benzoate

HATU (491 mg, 1.29 mmol) was added to a cold (0° C.) solution of 4-tert-butoxycarbonyl-3,5-difluoro-benzoic acid (303 mg, 1.17 mmol) and DiPEA (579 µL, 3.51 mmol) in DMF (11.7 mL). After stirring for 10 minutes at 0° C., 2-methoxyethylamine (153 µL, 1.76 mmol) was added and the reaction mixture was stirred for 3 h allowing the mixture to come to room temperature. The reaction mixture was added to a stirred mixture of water/brine/ethyl acetate=1/1/1 v/v % (300 ml). The organic layer was separated, washed with water, brine, dried over sodium sulfate, filtered and concentrated under reduced pressure. The crude residue was purified by column chromatography (heptane/ethyl acetate=10/0 to 1/1 v/v %) to afford 268 mg of the title compound (yield: 73%).

(c) 2,6-difluoro-4-(2-methoxyethylcarbamoyl)benzoic Acid (Intermediate 37)

This compound was prepared in an analogous manner as described for Intermediate 30e starting with tert-butyl 2,6-difluoro-4-(2-methoxyethylcarbamoyl)benzoate to afford the title compound in quantitative crude yield.

Intermediate 38

2-[[(1S)-1-phenylethyl]amino]ethanehydroxamic Acid hydrochloride (a) Methyl 2-[[(1S)-1-phenylethyl]amino]acetate To a solution of (1S)-1-phenylethylamine (500 mg, 3.9 mmol) in acetonitrile (20 mL) was added methyl bromoacetate (371 µL, 3.9 mmol) and potassium carbonate (1.08 g, 7.8 mmol). The reaction mixture was stirred o/w at room temperature. The mixture was filtered and the filtrate was concentrated under vacuum to give the crude tile compound (703 mg, 93%).

(b) Methyl 2-[tert-butoxycarbonyl-[(1S)-1-phenylethyl]amino]acetate

To a solution of methyl 2-[[(1S)-1-phenylethyl]amino] acetate (703 mg, 3.64 mmol) in water (15 mL) was added a solution of di-tert-butyl dicarbonate (1.19 g, 5.46 mmol) in dioxane (3 mL) and the mixture was stirred at room temperature for 3 h. The mixture was extracted with ethyl acetate. The organic layer was separated and washed with water, brine, dried ($Na_2SO_4$), filtered and concentrated under reduced pressure to give methyl 2-[tert-butoxycarbonyl-[(1S)-1-phenylethyl]amino]acetate in quantitative yield.

(c) 2-[tert-Butoxycarbonyl-[(1S)-1-phenylethyl] amino]acetic Acid

To a solution of methyl 2-[tert-butoxycarbonyl-[(1S)-1-phenylethyl]amino]acetate (1.3 g, 3.87 mmol) in THF/MeOH=3/1 v/v % (40 mL) was added 1N LiOH-solution (10 mL) and the reaction mixture was stirred at room temperature o/n. Cold water was added to the mixture and 5% citric acid solution was added until pH<3. Ethyl acetate was added and after stirring, the organic phase was separated, washed with water, brine, dried ($Na_2SO_4$), filtered and concentrated under reduced pressure to give the 947 mg of the title compound (Yield: 88%).

(d) tert-Butyl N-[2-oxo-2-(tetrahydropyran-2-yloxyamino)ethyl]-N-[(1S)-1-phenylethyl]carbamate This compound was prepared in an analogous manner as described for Intermediate 37b starting with 2-[tert-butoxycarbonyl-[(1S)-1-phenylethyl]amino]acetic acid and 0-tetrahydropyran-2-ylhydroxylamine to give 1.68 g of the title compound (quantitative crude yield).

(e) tert-Butyl N-[2-(hydroxyamino)-2-oxo-ethyl]-N-[(1S)-1-phenylethyl]carbamate

To a solution of tert-butyl N-[2-oxo-2-(tetrahydropyran-2-yloxyamino)ethyl]-N-[(1S)-1-phenylethyl]carbamate (1.64 g, 3.24 mmol) in methanol (25 mL) was added p-toluenesulfonic acid monohydrate (1.23 g, 6.48 mmol) and the reaction mixture was stirred for 1 h at room temperature. Dichloromethane (225 mL) was added and the mixture was washed with 5% $NaHCO_3$-solution, water, brine, dried over sodium sulfate, filtered and concentrated under reduced pressure. The crude residue was purified by column chromatography (heptane to ethyl acetate=10/0 to 1/3 v/v %) to afford 775 mg of the title compound (yield: 81%).

(f) 2-[[(1S)-1-phenylethyl]amino]ethanehydroxamic Acid hydrochloride (Intermediate 38)

To a solution of tert-butyl N-[2-(hydroxyamino)-2-oxoethyl]-N-[(1S)-1-phenylethyl]carbamate (775 mg, 2.63 mmol) in dioxane (1.5 mL) was added 4N HCl in dioxane (5 mL). The reaction mixture was stirred at room temperature for 2 h. The mixture was concentrated under reduced pressure and traces of hydrochloric acid were removed by co-evaporated with dichloromethane (3×) to give 681 mg of the title compound (quantitative yield).

Intermediate 39

2-[1-(2,6-Difluorophenyl)ethylamino]ethanehydroxamic Acid hydrochloride

This compound was prepared in an analogous manner as described for Intermediate 38, starting with 1-(2,6-difluorophenyl)ethanamine to afford 100 mg of the title compound.

Intermediate A

3-Benzyloxy-2-(3-bromophenyl)imidazolidin-4-one (a) tert-Butyl N-[2-(benzyloxyamino)-2-oxo-ethyl] carbamate Boc-Gly-OH (2.5 g, 14.3 mmol) and O-benzylhydroxylamine hydrochloride (2.07 g, 13.0 mmol) were suspended in DCM (25 mL). HATU (4.93 g, 13.0 mmol) and NEM (3.3 mL, 25.9 mmol) were added subsequently to the reaction mixture and the mixture stirred at room temperature o/n. The reaction mixture was concentrated to small volume and subsequently diluted with ethyl acetate. The organic layer was washed with a 5% $NaHCO_3$-solution, 0.2M HCl-solution, water and brine, then dried over sodium sulfate, filtered and concentrated in vacuo to give 3.3 g of the crude product as an oil (yield 90.6%). This crude product was used in the next step without further purification.

(b) 2-Amino-N-benzyloxy-acetamide 2,2,2-trifluoroacetic Acid tert-Butyl N-[2-(benzyloxyamino)-2-oxo-ethyl]carbamate (3.3 g, 11.8 mmol) was dissolved in dichloromethane (20 mL). Water (300 µL) and trifluoroacetic acid (20 mL) were added and the reaction mixture was stirred at room temperature for 3 h. The mixture was concentrated to a small volume and added dropwise to 300 mL of diethyl ether under vigorous stirring. After stirring for an additional hour at room temperature, the diethyl ether layer was decanted. Diethyl ether was added to the remaining precipitate and stirred again for 1 hour. The precipitate was filtered, washed with diethyl ether and dried under vacuum to give 2.87 g of 2-amino-N-benzyloxy-acetamide 2,2,2-trifluoroacetic acid as a white powder (yield: 82.7%).

Part of the product was dissolved in methanol and then filtered over a SCX-2 column. After rinsing the column with methanol, the desired product was eluted with an 0.7N ammonia/methanol solution to give 2-amino-N-benzyloxy-acetamide (500 mg).

(c) 3-Benzyloxy-2-(3-bromophenyl)imidazolidin-4-one (Intermediate A)

To a suspension of 2-amino-N-benzyloxy-acetamide (500 mg, 2.77 mmol) in ethanol (5 mL) was added 3-bromobenzaldehyde (356 µL, 3.05 mmol). The reaction mixture was refluxed for 1 h and after TLC indicated a complete conversion of the starting material the mixture was concentrated in vacuo and the crude residue was purified by column chromatography (heptane to ethyl acetate=8/2 to 1/1 v/v %) to afford the title compound: 620 mg (64.5% yield).

Intermediate B (5S)-3-benzyloxy-2-(3-bromophenyl)-5-methyl-imidazolidin-4-one

This compound was prepared in an analogous manner as described for Intermediate A, starting from Boc-L-Ala-OH and O-benzylhydroxylamine hydrochloride to afford the title compound (250 mg, 67%).

Intermediate C (5R)-3-benzyloxy-2-(3-bromophenyl)-5-methyl-imidazolidin-4-one

This compound was prepared in an analogous manner as described for Intermediate A, starting from Boc-D-Ala-OH and O-benzylhydroxylamine hydrochloride to afford the title compound (145 mg, 80%).

Intermediate D

3-Benzyloxy-2-(3-chlorophenyl)imidazolidin-4-one

This compound was prepared in an analogous manner as described for Intermediate A, starting from Boc-Gly-OH, O-benzylhydroxylamine hydrochloride and 3-chlorobenzaldehyde to afford the title compound (260 mg, 34%).

Example 1

1-Benzoyl-3-hydroxy-2-[3-(trifluoromethyl)phenyl]imidazolidin-4-one

Chlorotrimethylsilane (29.5 µL, 0.23 mmol) was added to a solution of DiPEA (57.8 µL, 0.35 mmol) in dichloromethane (1 mL). The resulting mixture was added dropwise to a stirred suspension 3-hydroxy-2-[3-(trifluoromethyl)phenyl]imidazolidin-4-one (Intermediate 2, 29.5 mg, 0.12 mmol) in dichloromethane (1 mL). After stirring for 15 minutes at room temperature, the reaction mixture was cooled to 0° C. and DiPEA (37.9 µL, 0.23 mmol) was added followed by a solution of benzoyl chloride (13.9 µL, 0.12 mmol) in dichloromethane (0.5 mL). The resulting solution was stirred for 15 minutes at 0° C. After TLC analysis indicated a complete conversion of starting material, the reaction was quenched with 5% citric acid solution (4 m L). The water layer was extracted with dichloromethane. The combined organic layers were washed with a solution of 5% NaHCO$_3$ (4 mL), filtered over a PE filter and concentrated in vacuo to give an oil. Purification was performed using preparative HPLC to afford the title compound (10.2 mg, 24%). Data: LCMS (B) R$_t$: 9.800 min; m/z 351.1 (M+H)$^+$.

Example 2

1-(2-Chlorobenzoyl)-3-hydroxy-2-[3-(trifluoromethyl)phenyl]imidazolidin-4-one

This compound was prepared from Intermediate 2 and 2-chlorobenzoyl chloride according to the procedure described in Example 1. Purification was performed using preparative HPLC to afford the title compound (11.8 mg, 37%). Data: LCMS (B) R$_t$: 10.271 min; m/z 385.1/387.0 (M+H)$^+$ (chloride-pattern).

Example 3

1-(2-Chloro-6-fluoro-benzoyl)-3-hydroxy-2-[3-(trifluoromethyl)phenyl]imidazolidin-4-one This compound was prepared from Intermediate 2 and 2-chloro-6-fluorobenzoyl chloride according to the procedure described in Example 1. Purification was performed using preparative HPLC to afford the title compound (9.1 mg, 19%). Data: LCMS (B) R$_t$: 10.403 min; m/z 403.0/405.0 (M+H)$^-$ (chloride-pattern).

Example 4

1-(2,6-Difluorobenzoyl)-3-hydroxy-2-[3-(trifluoromethyl)phenyl]imidazolidin-4-one This compound was prepared from Intermediate 2 and 2,6-difluorobenzoyl chloride according to the procedure described in Example 1. Purification was performed using preparative HPLC to afford the title compound (20 mg, 43%). Data: LCMS (B) R$_t$: 10.113 min; m/z 387.0 (M+H)$^+$.

Example 5

3-[1-(2-Fluorobenzoyl)-3-hydroxy-4-oxo-imidazolidin-2-yl]benzonitrile

This compound was prepared from Intermediate 3 and 2-fluorobenzoyl chloride according to the procedure described in Example 1. Purification was performed using preparative HPLC to afford the title compound (16.8 mg, 43%). Data: LCMS (B) R$_t$: 7.223 min; m/z 326.1 (M+H)$^+$.

Example 6

3-[1-(2-Chloro-6-fluoro-benzoyl)-3-hydroxy-4-oxo-imidazolidin-2-yl]benzonitrile

This compound was prepared from Intermediate 3 and 2-chloro-6-fluorobenzoyl chloride according to the procedure described in Example 1. Purification was performed using preparative HPLC to afford the title compound (14.3 mg, 33%). Data: LCMS (B) R$_t$: 7.861 min; m/z 360.0 (M+H)$^+$.

Example 7

1-(2-Chloro-6-fluoro-benzoyl)-2-[4-chloro-3-(trifluoromethyl)phenyl]-3-hydroxy-imidazolidin-4-one This compound was prepared from Intermediate 4 and 2-chloro-6-fluorobenzoyl chloride according to the procedure described in Example 1. Purification was performed using preparative HPLC to afford the title compound (26 mg, 50%). Data: LCMS (B) $R_t$: 11.615 min; m/z 437.0/439.0 (M+H)$^+$ (dichloride-pattern).

Example 8

2-[4-Chloro-3-(trifluoromethyl)phenyl]-1-(2-fluorobenzoyl)-3-hydroxy-imidazolidin-4-one This compound was prepared from Intermediate 4 and 2-fluorobenzoyl chloride according to the procedure described in Example 1. Purification was performed using preparative HPLC to afford the title compound (29 mg, 60%). Data: LCMS (B) $R_t$: 11.144 min; m/z 403.0/405.1 (M+H)$^+$ (chloride-pattern).

Example 9

2-[4-Chloro-3-(trifluoromethyl)phenyl]-1-(2,6-difluorobenzoyl)-3-hydroxy-imidazolidin-4-one This compound was prepared from Intermediate 4 and 2,6-difluorobenzoyl chloride according to the procedure described in Example 1. Purification was performed using preparative HPLC to afford the title compound (32 mg, 63%). Data: LCMS (B) $R_t$: 11.295 min; m/z 421.0/423.0 (M+H)$^+$ (chloride-pattern).

Example 10

1-(2-Fluorobenzoyl)-3-hydroxy-2-[3-(trifluoromethyl)phenyl]imidazolidin-4-one

This compound was prepared from Intermediate 2 and 2-fluorobenzoyl chloride according to the procedure described in Example 1. Purification was performed using preparative HPLC to afford the title compound (7.6 mg, 17%). Data: LCMS (B) $R_t$: 9.889 min; m/z 369.1 (M+H)$^+$.

Example 11

1-(2,6-Difluorobenzoyl)-2-(3-fluorophenyl)-3-hydroxy-imidazolidin-4-one

This compound was prepared from Intermediate 5 and 2,6-difluorobenzoyl chloride according to the procedure described in Example 1. Purification was performed using preparative HPLC to afford the title compound (20 mg, 50%). Data: LCMS (B) $R_t$: 8.146 min; m/z 337.1 (M+H)$^+$.

Example 12

1-(2-Fluorobenzoyl)-2-(3-fluorophenyl)-3-hydroxy-imidazolidin-4-one

This compound was prepared from Intermediate 5 and 2-fluorobenzoyl chloride according to the procedure described in Example 1. Purification was performed using preparative HPLC to afford the title compound (17 mg, 44%). Data: LCMS (B) $R_t$: 8.017 min; m/z 319.1 (M+H)$^+$.

Example 13

2-(3-Chlorophenyl)-1-(2-fluorobenzoyl)-3-hydroxy-imidazolidin-4-one

This compound was prepared from Intermediate 6 and 2-fluorobenzoyl chloride according to the procedure described in Example 1. Purification was performed using preparative HPLC to afford the title compound (27 mg, 67%). Data: LCMS (B) $R_t$: 8.992 min; m/z 335.1/337.0 (M+H)$^+$ (chloride pattern).

Example 14

1-(2-Chloro-6-fluoro-benzoyl)-2-(3-chlorophenyl)-3-hydroxy-imidazolidin-4-one

This compound was prepared from Intermediate 6 and 2-chloro-6-fluorobenzoyl chloride according to the procedure described in Example 1. Purification was performed using preparative HPLC to afford the title compound (27 mg, 61%). Data: LCMS (B) $R_t$: 9.564 min; m/z 369.0/371.0 (M+H)$^+$ (dichloride pattern).

Example 15

2-(3-Chlorophenyl)-1-(2,6-difluorobenzoyl)-3-hydroxy-imidazolidin-4-one

This compound was prepared from Intermediate 6 and 2,6-difluorobenzoyl chloride according to the procedure described in Example 1. Purification was performed using preparative HPLC to afford the title compound (26 mg, 61%). Data: LCMS (B) $R_t$: 9.136 min; m/z 353.0/355.0 (M+H)$^+$ (chloride pattern).

Example 16

2-(3-Bromophenyl)-1-(2,4-dichlorobenzoyl)-3-hydroxy-imidazolidin-4-one

This compound was prepared from Intermediate 7 and 2,4-dichlorobenzoyl chloride according to the procedure described in Example 1. Purification was performed using preparative HPLC to afford the title compound (32 mg, 62%). Data: LCMS (B) $R_t$: 11.483 min; m/z 430.9 (M+H)$^+$ (chloride/bromide pattern).

Example 17

1-Benzoyl-2-(3-bromophenyl)-3-hydroxy-imidazolidin-4-one

This compound was prepared from Intermediate 7 and benzoyl chloride according to the procedure described in Example 1. Purification was performed using preparative HPLC to afford the title compound (106 mg, 28%). Data: LCMS (B) $R_t$: 9.253 min; m/z 361.0/363.0 (M+H)$^+$ (bromide pattern).

Example 18

2-(3-Bromophenyl)-3-hydroxy-1-(4-methoxybenzoyl)imidazolidin-4-one

This compound was prepared from Intermediate 7 and p-anisoyl chloride according to the procedure described in Example 1. Purification was performed using preparative HPLC to afford the title compound (8.5 mg, 24%). Data: LCMS (B) $R_t$: 9.456 min; m/z 391.0/393.0 (M+H)$^+$ (bromide pattern).

Example 19

2-(3-Bromophenyl)-1-(cyclohexanecarbonyl)-3-hydroxy-imidazolidin-4-one

This compound was prepared from Intermediate 7 and cyclohexanecarbonyl chloride according to the procedure described in Example 1. Purification was performed using preparative HPLC to afford the title compound (19 mg, 43%). Data: LCMS (B) $R_t$: 10.698 min; m/z 367.1/369.1 (M+H)$^+$ (bromide pattern).

Example 20

2-(3-Bromophenyl)-3-hydroxy-1-(2-methylbenzoyl)imidazolidin-4-one

This compound was prepared from Intermediate 7 and o-toluoyl chloride according to the procedure described in Example 1. Purification was performed using preparative HPLC to afford the title compound (21 mg, 47%). Data: LCMS (B) $R_t$: 9.932 min; m/z 375.0/377.0 (M+H)$^+$ (bromide pattern).

Example 21

2-(3-bromophenyl)-1-(2,6-dichlorobenzoyl)-3-hydroxy-imidazolidin-4-one

This compound was prepared from Intermediate 7 and 2,6-dichlorobenzoyl chloride according to the procedure described in Example 1. Purification was performed using preparative HPLC to afford the title compound (13 mg, 25%). Data: LCMS (B) $R_t$: 10.292 min; m/z 428.9/430.9 (M+H)$^+$ (chloride/bromide pattern).

Example 22

2-(3-Bromophenyl)-1-(furan-2-carbonyl)-3-hydroxy-imidazolidin-4-one

This compound was prepared from Intermediate 7 and 2-furoyl chloride according to the procedure described in Example 1. Purification was performed using preparative HPLC to afford the title compound (21 mg, 50%). Data: LCMS (B) $R_t$: 8.144 min; m/z 351.0/353.0 (M+H)$^+$ (bromide pattern).

Example 23

2-(3-Bromo-4-fluoro-phenyl)-1-(cyclobutanecarbonyl)-3-hydroxy-imidazolidin-4-one This compound was prepared from Intermediate 8 and cyclobutanecarbonyl chloride according to the procedure described in Example 1. Purification was performed using preparative HPLC to afford the title compound (14 mg, 33%). Data: LCMS (B) $R_t$: 9.218 min; m/z 357.0/359.0 (M+H)$^+$ (bromide pattern).

Example 24

1-(2-Bromobenzoyl)-2-(3-bromophenyl)-3-hydroxy-imidazolidin-4-one

This compound was prepared from Intermediate 7 and 2-bromobenzoyl chloride according to the procedure described in Example 1. Purification was performed using preparative HPLC to afford the title compound (36 mg, 68%). Data: LCMS (B) $R_t$: 10.003 min; m/z 440.9/442.9 (M+H)$^+$ (bromide pattern).

Example 25

4-[2-(3-Bromophenyl)-3-hydroxy-4-oxo-imidazolidine-1-carbonyl]-3-chloro-5-fluoro-benzonitrile This compound was prepared from Intermediate 7 and 2-chloro-6-fluoro-4-cyanobenzoyl chloride according to the procedure described in Example 1. Purification was performed using preparative HPLC to afford the title compound (19 mg, 36%). Data: LCMS (B) $R_t$: 10.025 min; m/z 481.9/483.9 (M+H)$^+$ (bromide/chloride pattern).

Example 26

2-(3-Bromophenyl)-1-(2,5-difluorobenzoyl)-3-hydroxy-imidazolidin-4-one

This compound was prepared from Intermediate 7 and 2,5-difluorobenzoyl chloride according to the procedure described in Example 1. Purification was performed using preparative HPLC to afford the title compound (27 mg, 57%). Data: LCMS (B) $R_t$: 9.745 min; m/z 397.0/399.0 (M+H)$^+$ (bromide pattern).

Example 27

2-(3-Bromophenyl)-1-(2,6-difluorobenzoyl)-3-hydroxy-imidazolidin-4-one

This compound was prepared from Intermediate 7 and 2,6-difluorobenzoyl chloride according to the procedure described in Example 1. Purification was performed using preparative HPLC to afford the title compound (23.2 mg, 49%). Data: LCMS (B) $R_t$: 9.374 min; m/z 397.0/399.0 (M+H)$^+$ (bromide pattern).

Example 28

2-(3-Bromophenyl)-3-hydroxy-1-[2-(trifluoromethyl)benzoyl]imidazolidin-4-one

This compound was prepared from Intermediate 7 and 2-(trifluoromethyl)benzoyl chloride according to the procedure described in Example 1. Purification was performed using preparative HPLC to afford the title compound (36 mg, 70%). Data: LCMS (B) $R_t$: 10.654 min; m/z 429.0/431.0 (M+H)$^+$ (bromide pattern).

Example 29

2-(3-Bromophenyl)-1-(4-fluorobenzoyl)-3-hydroxy-imidazolidin-4-one

This compound was prepared from Intermediate 7 and 4-fluorobenzoyl chloride according to the procedure described in Example 1. Purification was performed using preparative HPLC to afford the title compound (10 mg, 21%). Data: LCMS (B) $R_t$: 9.775 min; m/z 379.0/381.0 (M+H)$^+$ (bromide pattern).

Example 30

2-(3-Bromophenyl)-1-(2-chloro-4-fluoro-benzoyl)-3-hydroxy-imidazolidin-4-one

This compound was prepared from Intermediate 7 and 2-chloro-4-fluorobenzoyl chloride according to the procedure described in Example 1. Purification was performed using preparative HPLC to afford the title compound (24.8 mg, 50%). Data: LCMS (B) $R_t$: 10.231 min; m/z 412.9/414.9 (M+H)$^+$ (chloride/bromide pattern).

Example 31

2-(3-Bromophenyl)-1-(2-chloro-5-fluoro-benzoyl)-3-hydroxy-imidazolidin-4-one

This compound was prepared from Intermediate 7 and 2-chloro-5-fluorobenzoyl chloride according to the procedure described in Example 1. Purification was performed using preparative HPLC to afford the title compound (28.6 mg, 58%). Data: LCMS (B) $R_t$: 10.103 min; m/z 412.9/414.9 (M+H)$^+$ (chloride/bromide pattern).

Example 32

2-(3-Bromophenyl)-1-(2-chloro-6-fluoro-benzoyl)-3-hydroxy-imidazolidin-4-one

This compound was prepared from Intermediate 7 and 2-chloro-6-fluorobenzoyl chloride according to the procedure described in Example 1. Purification was performed using preparative HPLC to afford the title compound (31 mg, 62%). Data: LCMS (B) $R_t$: 9.902 min; m/z 412.9/414.9 (M+H)$^+$ (chloride/bromide pattern).

Example 33

2-(3-Bromophenyl)-1-(2-fluorobenzoyl)-3-hydroxy-imidazolidin-4-one

This compound was prepared from Intermediate 7 and 2-fluorobenzoyl chloride according to the procedure described in Example 1. Purification was performed using preparative HPLC to afford the title compound (28 mg, 62%). Data: LCMS (B) $R_t$: 9.395 min; m/z 379.0/381.0 (M+H)$^+$ (bromide pattern).

Example 34

2-(3-Bromophenyl)-1-(2-chlorobenzoyl)-3-hydroxy-imidazolidin-4-one

This compound was prepared from Intermediate 7 and 2-chlorobenzoyl chloride according to the procedure described in Example 1. Purification was performed using preparative HPLC to afford the title compound (28 mg, 59%). Data: LCMS (B) $R_t$: 9.338 min; m/z 394.9/379.0 (M+H)$^+$ (chloride/bromide pattern).

Example 35

2-(3-Bromophenyl)-1-(2,3-dichlorobenzoyl)-3-hydroxy-imidazolidin-4-one

This compound was prepared from Intermediate 7 and 2,3-dichlorobenzoyl chloride according to the procedure described in Example 1. Purification was performed using preparative HPLC to afford the title compound (8.97 mg, 17%). Data: LCMS (B) $R_t$: 10.889 min; m/z 428.9/430.9 (M+H)$^+$ (chloride/bromide pattern).

Example 36

2-(3-Bromophenyl)-1-(3-fluorobenzoyl)-3-hydroxy-imidazolidin-4-one

This compound was prepared from Intermediate 7 and 3-fluorobenzoyl chloride according to the procedure described in Example 1. Purification was performed using preparative HPLC to afford the title compound (25.1 mg, 55%). Data: LCMS (B) $R_t$: 9.790 min; m/z 378.9/380.9 (M+H)$^+$ (bromide pattern).

Example 37

2-(3-Bromophenyl)-1-[2-fluoro-6-(trifluoromethyl)benzoyl]-3-hydroxy-imidazolidin-4-one This compound was prepared from Intermediate 7 and 2-fluoro-6-(trifluoromethyl)benzoyl chloride according to the procedure described in Example 1. Purification was performed using preparative HPLC to afford the title compound (13.9 mg, 26%). Data: LCMS (B) $R_t$: 10.579 min; m/z 447.0/449.0 (M+H)$^+$ (bromide pattern).

Example 38

2-(3-Bromophenyl)-1-[2-fluoro-4-(trifluoromethyl)benzoyl]-3-hydroxy-imidazolidin-4-one This compound was prepared from Intermediate 7 and 2-fluoro-4-(trifluoromethyl)benzoyl chloride according to the procedure described in Example 1. Purification was performed using preparative HPLC to afford the title compound (37.1 mg, 69%). Data: LCMS (B) $R_t$: 11.744 min; m/z 447.0/449.0 (M+H)$^+$ (bromide pattern).

Example 39

1-Benzoyl-2-(3-bromo-4-fluoro-phenyl)-3-hydroxy-imidazolidin-4-one

This compound was prepared from Intermediate 8 and benzoyl chloride according to the procedure described in Example 1. Purification was performed using preparative HPLC to afford the title compound (14 mg, 31%). Data: LCMS (B) $R_t$: 9.578 min; m/z 379.0/381.0 (M+H)$^+$ (bromide pattern).

Example 40

2-(3-Bromo-4-fluoro-phenyl)-1-(4-fluorobenzoyl)-3-hydroxy-imidazolidin-4-one

This compound was prepared from Intermediate 8 and 4-fluorobenzoyl chloride according to the procedure described in Example 1. Purification was performed using preparative HPLC to afford the title compound (5 mg, 10%). Data: LCMS (B) $R_t$: 10.083 min; m/z 397.0/399.0 (M+H)$^+$ (bromide pattern).

Example 41

1-(Benzenesulfonyl)-2-(3-bromo-4-fluoro-phenyl)-3-hydroxy-imidazolidin-4-one

This compound was prepared from Intermediate 8 and phenyl sulphonyl chloride according to the procedure described in Example 1. Purification was performed using preparative HPLC to afford the title compound (2.1 mg, 4.2%). Data: LCMS (B) $R_t$: 10.960 min; m/z 414.9/416.9 (M+H)$^+$ (bromide pattern).

Example 42

2-(3-Bromo-4-fluoro-phenyl)-1-(cyclopropanecarbonyl)-3-hydroxy-imidazolidin-4-one This compound was prepared from Intermediate 8 and cyclopropanecarbonyl chloride according to the procedure described in Example 1. Purification was performed using preparative HPLC to afford the title compound (10 mg, 24%). Data: LCMS (B) $R_t$: 8.048 min; m/z 343.0/345.0 (M+H)$^+$ (bromide pattern).

Example 43

2-(3-Bromo-4-fluoro-phenyl)-1-(3-fluorobenzoyl)-3-hydroxy-imidazolidin-4-one

This compound was prepared from Intermediate 8 and 3-fluorobenzoyl chloride according to the procedure described in Example 1. Purification was performed using preparative HPLC to afford the title compound (26 mg, 55%). Data: LCMS (B) $R_t$: 10.135 min; m/z 397.0/399.0 (M+H)$^+$ (bromide pattern).

Example 44

2-(3-Bromo-4-fluoro-phenyl)-1-(2,6-difluorobenzoyl)-3-hydroxy-imidazolidin-4-one This compound was prepared from Intermediate 8 and 2,6-difluorobenzoyl chloride according to the procedure described in Example 1. Purification was performed using preparative HPLC to afford the title compound (30 mg, 60%). Data: LCMS (B) $R_t$: 9.745 min; m/z 415.0/417.0 (M+H)$^+$ (bromide pattern).

Example 45

2-(3-Bromo-4-fluoro-phenyl)-1-(2-chloro-6-fluoro-benzoyl)-3-hydroxy-imidazolidin-4-one This compound was prepared from Intermediate 8 and 2-chloro-6-fluorobenzoyl chloride according to the procedure described in Example 1. Purification was performed using preparative HPLC to afford the title compound (25 mg, 48%). Data: LCMS (B) $R_t$: 10.249 min; m/z 430.9/432.9 (M+H)$^+$ (chloride/bromide pattern).

Example 46

2-(3-Bromo-4-fluoro-phenyl)-1-(2-fluoro-benzoyl)-3-hydroxy-imidazolidin-4-one

This compound was prepared from Intermediate 8 and 2-fluorobenzoyl chloride according to the procedure described in Example 1. Purification was performed using preparative HPLC to afford the title compound (12 mg, 25%). Data: LCMS (B) $R_t$: 9.780 min; m/z 397.0/399.0 (M+H)$^+$ (bromide pattern).

Example 47

2-(3-Bromo-4-fluoro-phenyl)-3-hydroxy-1-(4-methoxybenzoyl)imidazolidin-4-one

This compound was prepared from Intermediate 8 and p-anisoyl chloride according to the procedure described in Example 1. Purification was performed using preparative HPLC to afford the title compound (32 mg, 65%). Data: LCMS (B) $R_t$: 9.763 min; m/z 408.9/411.0 (M+H)$^+$ (bromide pattern).

Example 48

2-(3-Bromo-4-fluoro-phenyl)-1-(2,6-dichlorobenzoyl)-3-hydroxy-imidazolidin-4-one This compound was prepared from Intermediate 8 and 2,6-dichlorobenzoyl chloride according to the procedure described in Example 1. Purification was performed using preparative HPLC to afford the title compound (11 mg, 20%). Data: LCMS (B) $R_t$: 10.547 min; m/z 446.9/448.9 (M+H)$^+$ (chloride/bromide pattern).

Example 49

2-(3-Chloro-4-fluoro-phenyl)-1-(2,6-dichlorobenzoyl)-3-hydroxy-imidazolidin-4-one This compound was prepared from Intermediate 9 and 2,6-dichlorobenzoyl chloride according to the procedure described in Example 1. Purification was performed using preparative HPLC to afford the title compound (9 mg, 19%). Data: LCMS (B) R$_t$: 10.429 min; m/z 402.9/404.9 (M+H)$^+$ (chloride pattern).

Example 50

1-Benzoyl-2-(3-chloro-4-fluoro-phenyl)-3-hydroxy-imidazolidin-4-one

This compound was prepared from Intermediate 9 and benzoyl chloride according to the procedure described in Example 1. Purification was performed using preparative HPLC to afford the title compound (23 mg, 57%). Data: LCMS (B) R$_t$: 9.457 min; m/z 335.1/337.1 (M+H)$^+$ (chloride pattern).

Example 51

2-(3-Chloro-4-fluoro-phenyl)-1-(2-fluorobenzoyl)-3-hydroxy-imidazolidin-4-one

This compound was prepared from Intermediate 9 and 2-fluorobenzoyl chloride according to the procedure described in Example 1. Purification was performed using preparative HPLC to afford the title compound (20 mg, 47%). Data: LCMS (B) R$_t$: 9.572 min; m/z 353.0/355.1 (M+H)$^+$ (chloride pattern).

Example 52

2-(3-Chloro-4-fluoro-phenyl)-1-(2,6-difluorobenzoyl)-3-hydroxy-imidazolidin-4-one This compound was prepared from Intermediate 9 and 2,6-difluorobenzoyl chloride according to the procedure described in Example 1. Purification was performed using preparative HPLC to afford the title compound (21.2 mg, 47%). Data: LCMS (B) R$_t$: 9.604 min; m/z 371.0/372.0 (M+H)$^+$ (chloride pattern).

Example 53

1-(2-Chloro-6-fluoro-benzoyl)-2-(3-chloro-4-fluoro-phenyl)-3-hydroxy-imidazolidin-4-one This compound was prepared from Intermediate 9 and 2-chloro-6-fluorobenzoyl chloride according to the procedure described in Example 1. Purification was performed using preparative HPLC to afford the title compound (18 mg, 47%). Data: LCMS (B) R$_t$: 10.087 min; m/z 387.0/389.0 (M+H)$^+$ (chloride pattern).

Example 54

2-(3-Bromophenyl)-1-(2,4-difluorobenzoyl)-3-hydroxy-imidazolidin-4-one (a) 3-Benzyloxy-2-(3-bromophenyl)-1-(2,4-difluorobenzoyl)imidazolidin-4-one To a cold (4° C.) solution of 3-benzyloxy-2-(3-bromophenyl)imidazolidin-4-one (Intermediate A, 40 mg, 0.12 mmol) in dichloromethane (5 mL) and N,N-diisopropylethylamine (38.1 µL, 0.23 mmol) was added dropwise a solution of 2,4-difluorobenzoyl chloride (14.2 µL, 0.12 mmol) in dichloromethane (1 mL). The reaction mixture was stirred for 2 h allowing to come to room temperature. The reaction mixture was concentrated in vacuo and the crude residue was purified by column chromatography (heptane to ethyl acetate=9/1 to 1/1 v/v %) to afford the title compound: 49.2 mg (84.1% yield).

(b) 2-(3-Bromophenyl)-1-(2,4-difluorobenzoyl)-3-hydroxy-imidazolidin-4-one

A solution of 3-benzyloxy-2-(3-bromophenyl)-1-(2,4-difluorobenzoyl)imidazolidin-4-one (49.2 mg, 0.1 mmol) in ethyl acetate (10 mL) was hydrogenated using an H-Cube continuous-flow reactor, 20% Pd(OH)$_2$/C, at room temperature, 1 bar, full H$_2$ modus, 1 mL/min. The pooled eluate was concentrated in vacuo and the crude product was purified using preparative HPLC to afford the title compound (18 mg, 45.3%). Data: LCMS (B) R$_t$: 9.748 min; m/z 397.0/399.0 (M+H)$^+$ (bromide pattern)

Example 55

(5S)-2-(3-Bromophenyl)-1-(2-fluorobenzoyl)-3-hydroxy-5-methyl-imidazolidin-4-one (Stereoisomer 4)

This compound was prepared from Intermediate B and 2-fluorobenzoyl chloride according to procedures described in Example 54. Purification was performed using preparative HPLC to afford the two separated diastereomers of title compound (7.53 mg, 16%) (Stereoisomer 4 is the last eluted isomer). Data: LCMS (B) R$_t$: 10.035 min; m/z 393.0/395.0 (M+H)$^+$ (bromide pattern).

Example 56

(5R)-2-(3-Bromophenyl)-1-(2-chloro-6-fluoro-benzoyl)-3-hydroxy-5-methyl-imidazolidin-4-one (Stereoisomer 1)

This compound was prepared from Intermediate C and 2-chloro-6-fluorobenzoyl chloride according to procedures described in Example 54. Purification was performed using preparative HPLC to afford the pure diastereomeric title compound (8.34 mg, 24%) (Stereoisomer 1 is the first eluted isomer). Data: LCMS (B) R$_t$: 10.222 min; m/z 427.0/428.9 (M+H)$^+$ (chloride/bromide pattern).

Example 57

(5R)-2-(3-Bromophenyl)-1-(2-fluorobenzoyl)-3-hydroxy-5-methyl-imidazolidin-4-one (Stereoisomer 1)

This compound was prepared from Intermediate C and 2-fluorobenzoyl chloride according to procedures described in Example 54. Purification was performed using preparative HPLC to afford the pure diastereomeric title compound (2.3 mg, 10%) (Stereoisomer 1 is the first eluted isomer). Data: LCMS (B) R$_t$: 9.660 min; m/z 393.0/395.0 (M+H)$^+$ (bromide pattern).

Example 58

2-(3-Bromophenyl)-3-hydroxy-1-(pyrazine-2-carbonyl)imidazolidin-4-one

(a) 3-Benzyloxy-2-(3-bromophenyl)-1-(pyrazine-2-carbonyl)imidazolidin-4-one This compound was prepared from Intermediate A and 2-pyrazinecarbonyl chloride according to procedures described in Example 54a.

(b) 2-(3-Bromophenyl)-3-hydroxy-1-(pyrazine-2-carbonyl)imidazolidin-4-one

To a cold (0° C.) solution of 3-benzyloxy-2-(3-bromophenyl)-1-(pyrazine-2-carbonyl) imidazolidin-4-one (30 mg, 0.066 mmol) in dichloromethane (2 mL) was added dropwise a solution of $BBr_3$ (1M in DCM, 130 µL). The reaction mixture was stirred for 1 h at 0° C. and then allowed to come to room temperature. Methanol (200 µL) was added to the reaction mixture followed by 1 mL 5% $NaHCO_3$, 1 mL water, 1 mL NaOH and 2 mL DCM. The water layer was extracted with DCM. The water layer was carefully acidified with 2 mL HCl to pH 5-6. The water layer was extracted with 2 times with dichloromethane/methanol 9/1 v/v % (2 mL). The organic fractions were filtered over a PE filter and concentrated. Purification was performed using preparative HPLC to afford the title compound (4.85 mg, 20%). Data: LCMS (B) $R_t$: 6.847 m in; m/z 363.0/365.0 $(M+H)^+$ (bromide pattern).

Example 59

2-(3-Chlorophenyl)-1-(2,4-difluorobenzoyl)-3-hydroxy-imidazolidin-4-one

This compound was prepared from Intermediate D and 2,4-difluorobenzoyl chloride according to procedures described in Example 54a and Example 58b. Purification was performed using preparative HPLC to afford the title compound (13.9 mg, 59%). Data: LCMS (B) $R_t$: 9.193 min; m/z 353.1/355.1 $(M+H)^+$ (chloride pattern).

Example 60

1-Benzoyl-2-(3-chlorophenyl)-3-hydroxy-imidazolidin-4-one

This compound was prepared from Intermediate D and benzoyl chloride according to procedures described in Example 54a and Example 58b. Purification was performed using preparative HPLC to afford the title compound (11.1 mg, 53%). Data: LCMS (B) $R_t$: 8.451 min; m/z 317.1/319.1 $(M+H)^+$ (chloride pattern).

Example 61

2-(3-Bromophenyl)-1-(2-chloropyridine-3-carbonyl)-3-hydroxy-imidazolidin-4-one This compound was prepared from Intermediate A and 2-chloropyridine-3-carbonyl chloride according to procedures described in Example 54a and Example 58b. Purification was performed using preparative HPLC to afford the title compound (3.3 mg, 12%). Data: LCMS (B) $R_t$: 7.203 min; m/z 396.0/398.0 $(M+H)^+$ (bromide/chloride pattern).

Example 62

2-(3-Bromophenyl)-3-hydroxy-1-(2,3,4,5,6-pentafluorobenzoyl)imidazolidin-4-one This compound was prepared from Intermediate A and pentafluorobenzoyl chloride according to procedures described in Example 54a and Example 58b. Purification was performed using preparative HPLC to afford the title compound (3.3 mg, 9.7%). Data: LCMS (B) $R_t$: 10.697 min; m/z 450.8/452.8 $(M+H)^+$ (bromide pattern). Separation of enantiomers of Example 17

Example 63

1-Benzoyl-2-(3-bromophenyl)-3-hydroxy-imidazolidin-4-one (Isomer 1 and Isomer 2)

To a cold (0° C.) solution of 1-benzoyl-2-(3-bromophenyl)-3-hydroxy-imidazolidin-4-one (Example 17, 40 mg, 0.11 mmol) in dichloromethane (1.5 mL) was added subsequently N,N-diisopropylethylamine (37 µL, 0.22 mmol) and a solution of (2R)-3,3,3-trifluoro-2-methoxy-2-phenyl-propanoyl chloride (22 µL, 0.12 mmol) in dichloromethane (1.5 mL). The reaction mixture was stirred for 30 min allowing the temperature to come to room temperature. The mixture was diluted with ethyl acetate and washed with water, brine, dried over sodium sulfate, filtered and the solvent was removed by evaporation at reduced pressure to give 69 mg of the crude product. The mixture of the two diastereomers was separated by column chromatography (hexane/diethyl ether=3/1 v/v % isocratic) to afford the two separate diastereomers (diastereomer 1, first eluting from the column, obtained in 20 mg and diastereomer 2, last eluting, in 39 mg). $^1$H-NMR showed for diastereomer 1 an 80% de and for diastereomer 2 20% de.

Both diastereomers were reacted separately with 5 eq. of morpholine in ethyl acetate at room temperature o/n. After reaction, ethyl acetate was added and the mixture was washed with water, brine, dried over sodium sulfate, filtered and concentrated in vacuo. Enantiomeric enriched compounds were obtained after purification using preparative HPLC to afford Example 63a, 1-benzoyl-2-(3-bromophenyl)-3-hydroxy-imidazolidin-4-one (isomer 1, 2.8 mg, 22%) and Example 63b, 1-benzoyl-2-(3-bromophenyl)-3-hydroxy-imidazolidin-4-one (isomer 2, 9 mg, 36%). Data: Example 63a LCMS (B) $R_t$: 9.021 min; m/z 361.0/363.0 $(M+H)^+$ (bromide pattern). Example 63b LCMS (B) $R_t$: 9.024 min; m/z 361.0/363.0 $(M+H)^+$ (bromide pattern).

Separation of Enantiomers of Example 17

Example 64

1-Benzoyl-2-(3-bromophenyl)-3-hydroxy-imidazolidin-4-one (Isomer 1 and Isomer 2)

These diastereomers were prepared in an analogous manner as described for Example 63a and 63b starting from Example 17 and (2S)-2-methoxy-2-phenyl-acetyl chloride. The mixture of the two diastereomers was separated by column chromatography (heptane/ethyl acetate=1/1 to 0/10 v/v %) to afford the two separate diastereomers (diastereomer 1, first eluting from the column, obtained in 74 mg and diastereomer 2, last eluting, in 75 mg). $^1$H-NMR showed for diastereomer 1>50% de and for diastereomer 2<50% de.

Diastereomer 1 were reacted with morpholine according to the procedure as described in Example 63. Enantiomeric enriched compound was obtained after purification using preparative HPLC to afford 1-benzoyl-2-(3-bromophenyl)-3-hydroxy-imidazolidin-4-one (Example 64, isomer 1, 35.5 mg, 66%). Data: LCMS (B) $R_t$: 9.022 min; m/z 361.0/363.0 (M+H)$^+$ (bromide pattern).

Example 65

2-(2-Bromo-4-pyridyl)-1-(2,6-difluorobenzoyl)-3-hydroxy-imidazolidin-4-one (a) 3-Benzyloxy-2-(2-bromo-4-pyridyl)-1-(2,6-difluorobenzoyl)imidazolidin-4-one To a suspension of 2-amino-N-benzyloxy-acetamide 2,2,2-trifluoroacetic acid (Intermediate Ab, 59 mg, 0.2 mmol) and 2-bromopyridine-4-carboxaldehyde (37 mg, 0.2 mmol) in acetonitrile (1 mL) was added N,N-diisopropylethylamine (33.0 µL, 0.2 mmol). The white suspension was heated for 2 h at 50° C. The mixture was cooled on an ice-water bath to <5° C. and N,N-diisopropylethylamine (33.0 µL, 0.2 mmol) was added. Subsequently a solution of 2,6-difluorobenzoyl chloride (30 µL, 0.24 mmol) in acetonitrile (0.1 mL) was added dropwise keeping the temperature below 5° C. The temperature of the reaction mixture was allowed to come to room temperature. The mixture was partially diluted with ethyl acetate (5 mL) and water (3 mL) was added slowly. The resulting phases were separated and the water layer was extracted with ethyl acetate (3 mL). The combined organic layers were washed with water (5 mL), 5% NaHCO$_3$-solution (5 mL), water (5 mL) and brine (5 mL), filtered over an PE filter filled with Na$_2$SO$_4$ and concentrated under reduced pressure. The crude residue was purified by column chromatography (heptane to ethyl acetate=100/0 to 0/100 v/v %) to afford the title compound (63 mg, 64%) as a white solid.

(b) 2-(2-Bromo-4-pyridyl)-1-(2,6-difluorobenzoyl)-3-hydroxy-imidazolidin-4-one (Example 65)

This compound was prepared in an analogous manner as described for Example 58b starting from 3-benzyloxy-2-(2-bromo-4-pyridyl)-1-(2,6-difluorobenzoyl)imidazolidin-4-one. Purification was performed using preparative HPLC to afford the title compound (5.0 mg, 10%). Data: LCMS (B) $R_t$: 7.553 min; m/z 397.9/400.0 (M+H)$^+$ (bromide pattern).

Example 66

2-(3-Bromophenyl)-1-(2,6-difluoro-4-methoxy-benzoyl)-3-hydroxy-imidazolidin-4-one This compound was prepared from Intermediate A and 2,6-difluoro-4-methoxy-benzoyl chloride according to procedure described in Example 54. Purification was performed using preparative HPLC to afford the title compound (3.0 mg, 5%). Data: LCMS (B) $R_t$: 10.319 min; m/z 426.9/428.9 (M+H)$^+$ (bromide pattern).

Example 67

1-(2,6-Difluorobenzoyl)-3-hydroxy-2-(3-nitrophenyl)imidazolidin-4-one

This compound was prepared in an analogous manner as described for Example 65 starting from Intermediate Ab, 3-nitrobenzaldehyde and 2,6-difluorobenzoyl chloride. Subsequent benzyl-deprotection was performed according to the procedure described in Example 58b. Purification was performed using preparative HPLC to afford the title compound (27.1 mg, 53%). Data: LCMS (B) $R_t$: 8.492 min; m/z 362.0 (M–H)$^-$.

Example 68

2-(6-Bromo-2-pyridyl)-1-(2,6-difluorobenzoyl)-3-hydroxy-imidazolidin-4-one

This compound was prepared in an analogous manner as described for Example 65 starting from Intermediate Ab, 6-bromo-2-pyridinecarboxaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (49 mg, 72%). Data: LCMS (B) $R_t$: 8.281 min; m/z 397.9/399.9 (M+H)$^+$ (bromide pattern).

Example 69

1-(2,6-Difluorobenzoyl)-3-hydroxy-2-(m-tolyl)imidazolidin-4-one (a) 3-Benzyloxy-1-(2,6-difluorobenzoyl)-2-(m-tolyl)imidazolidin-4-one This compound was prepared in an analogous manner as described for Example 65 starting from Intermediate Ab, 3-tolylbenzaldehyde and 2,6-difluorobenzoyl chloride to give 42 mg of the title compound (yield 50%).

(b) 1-(2,6-Difluorobenzoyl)-3-hydroxy-2-(m-tolyl)imidazolidin-4-one (Example 69)

To a cold (0° C.) solution of 3-benzyloxy-1-(2,6-difluorobenzoyl)-2-(m-tolyl)imidazolidin-4-one (42 mg, 0.10 mmol) in dichloromethane (4 mL) was added boron trifluoride methyl sulfide complex (23 µL, 0.22 mmol) to give a yellow/white suspension, which slowly turned into a clear solution. The reaction mixture was stirred for 3 h allowing the temperature to reach room temperature. The mixture was quenched with methanol (0.5 mL) and stirred 30 minutes at room temperature. 5% NaHCO$_3$-solution in water (2 mL) and dichloromethane were added. The layers were separated. The water layer was extracted with dichloromethane (3 mL). The combined organic layers were washed with water (5 mL) and filtered over a PE filter and concentrated in vacuo to give 35 mg of the crude title compound. Purification was performed using preparative HPLC to afford the title compound (18.3 mg, 55%). Data: LCMS (B) $R_t$: 8.970 min; m/z 333.1 (M+H)$^+$.

Example 70

2-(3-Bromo-2-fluoro-phenyl)-1-(2,6-difluorobenzoyl)-3-hydroxy-imidazolidin-4-one This compound was prepared in an analogous manner as described for Example 65 starting from Intermediate Ab, 3-bromo-2-fluorobenzaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (54 mg, 81%). Data: LCMS (B) $R_t$: 9.843 min; m/z 414.9/416.8 (M+H)$^+$ (bromide pattern).

Example 71

1-(2,6-Difluorobenzoyl)-3-hydroxy-2-(3-iodophenyl)imidazolidin-4-one

This compound was prepared in an analogous manner as described for Example 65 starting from Intermediate Ab, 3-iodobenzaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (44.5 mg, 77%). Data: LCMS (B) $R_t$: 10.091 min; m/z 444.8 (M+H)$^+$, 488.9 (M+HCOOH—H)$^-$.

Example 72

1-(2-chloro-6-fluoro-benzoyl)-3-hydroxy-2-(3-iodophenyl)imidazolidin-4-one

This compound was prepared in an analogous manner as described for Example 65 starting from Intermediate Ab, 3-iodobenzaldehyde and 2-chloro-6-fluorobenzoyl chloride. Subsequent benzyl-deprotection was performed using boron trifluoride methyl sulfide complex according to the procedure described in Example 69b. Purification was performed using preparative HPLC to afford the title compound (46.6 mg, 79%). Data: LCMS (B) $R_t$: 10.505 min; m/z 460.8 (M+H)$^+$, 504.9 (M+HCOOH—H)$^-$ (chloride pattern).

Example 73

1-(2-Fluorobenzoyl)-3-hydroxy-2-(3-iodophenyl)imidazolidin-4-one

This compound was prepared in an analogous manner as described for Example 65 starting from Intermediate Ab, 3-iodobenzaldehyde and 2-fluorobenzoyl chloride. Subsequent benzyl-deprotection was performed using boron trifluoride methyl sulfide complex according to the procedure described in Example 69b. Purification was performed using preparative HPLC to afford the title compound (42.9 mg, 77%). Data: LCMS (B) $R_t$: 9.941 min; m/z 426.9 (M+H)$^+$, 470.9 (M+HCOOH—H)$^-$.

Example 74

1-(4-Benzylbenzoyl)-2-(3-bromophenyl)-3-hydroxy-imidazolidin-4-one

This compound was prepared in an analogous manner as described for Example 65 starting from Intermediate Ab, 3-bromobenzaldehyde and 4-benzylbenzoyl chloride. Subsequent benzyl-deprotection was performed using boron trifluoride methyl sulfide complex according to the procedure described in Example 69b. Purification was performed using preparative HPLC to afford the title compound (45 mg, 55%). Data: LCMS (B) $R_t$: 13.428 min; m/z 451.0/453.0 (M+H)$^+$ (bromide pattern).

Example 75

2-(3-Bromophenyl)-1-(2,6-difluoro-3-nitro-benzoyl)-3-hydroxy-imidazolidin-4-one (a) 2,6-Difluoro-3-nitro-benzoyl chloride 2,6-Difluoro-3-nitro-benzoic acid (180 mg, 0.89 mmol) was dissolved in thionyl chloride (3 mL) and one drop of DMF was added. The reaction mixture was stirred at 75° C. for 1 h. After the mixture was cooled to room temperature, the solvent was evaporated under reduced pressure. Traces of thionyl chloride and hydrochloric acid were removed by co-evaporation with dichloromethane (2×) to give the title compound in a quantitative yield.

(b) [2-(3-Bromophenyl)-3-(2,6-difluoro-3-nitro-benzoyl)-5-oxo-imidazolidin-1-yl] 2,6-difluoro-3-nitro-benzoate To a cold (0° C.) suspension of 2-(3-bromophenyl)-3-hydroxy-imidazolidin-4-one (Intermediate 7, 100 mg, 0.39 mmol) in acetonitrile (5 mL) was added subsequently DiPEA (257 µL, 1.56 mmol) and a solution of 2,6-difluoro-3-nitro-benzoyl chloride (0.89 mmol) in acetonitrile (1 mL). After stirring for 5 min at 0° C., the ice-bath was removed and the mixture was stirred for 30 min allowing the temperature to reach room temperature. The mixture was diluted with ethyl acetate and washed with water. The organic layer was separated and washed with 1M HCl-solution in water, brine, dried over sodium sulfate, filtered and concentrated under reduced pressure. The crude residue was purified by column chromatography (heptane to ethyl acetate=100/0 to 1/1 v/v %) to afford the title compound (205 mg, 84%).

(c) 2-(3-Bromophenyl)-1-(2,6-difluoro-3-nitro-benzoyl)-3-hydroxy-imidazolidin-4-one (Example 75)

To a solution of [2-(3-bromophenyl)-3-(2,6-difluoro-3-nitro-benzoyl)-5-oxo-imidazolidin-1-yl] 2,6-difluoro-3-nitro-benzoate (205 mg, 0.33 mmol) in ethyl acetate (9 mL) was added a solution of 1-methylpiperazine (55 µL, 0.49 mmol) in ethyl acetate (1 mL). The reaction mixture was stirred at room temperature for 30 min. Ethyl acetate was added and the mixture was washed with 0.1M HCl-solution in water and brine. The organic layer was subsequently dried over sodium sulfate, filtered and concentrated by evaporation under reduced pressure to give 166 mg of crude 2-(3-bromophenyl)-1-(2,6-difluoro-3-nitro-benzoyl)-3-hydroxy-imidazolidin-4-one. Purification was performed on part of the product (18.5 mg) using preparative HPLC to afford the title compound (6 mg, 32.4%). Data: LCMS (B) $R_t$: 10.194 min; m/z 485.9/487.9 (M+HCOOH—H)$^-$ (bromide pattern).

Example 76

1-(3-Amino-2,6-difluoro-benzoyl)-2-(3-bromophenyl)-3-hydroxy-imidazolidin-4-one

To a cold (0° C.) solution of 2-(3-bromophenyl)-1-(2,6-difluoro-3-nitro-benzoyl)-3-hydroxy-imidazolidin-4-one (Example 75, 40 mg, 0.09 mmol) and acetic acid (77 µL, 1.35 mmol) in THF (5 mL) was added portion wise zinc (118 mg, 1.8 mmol). The mixture was stirred at room temperature for 1 h. and subsequently filtered over Decalite™. The filtrate was concentrated in vacuo. Purification was performed using preparative HPLC to afford the title compound (2.3 mg, 6%). Data: LCMS (B) R$_t$: 8.067 min; m/z 411.9/413.9 (M+H)$^+$ (bromide pattern).

Example 77

N-[3-[2-(3-bromophenyl)-3-hydroxy-4-oxo-imidazolidine-1-carbonyl]-2,4-difluoro-phenyl]acetamide (a) 3-Benzyloxy-2-(3-bromophenyl)-1-(2,6-difluoro-3-nitro-benzoyl)imidazolidin-4-one This compound was prepared from Intermediate A and 2,6-difluoro-3-nitro-benzoyl chloride according to procedures described in Example 54a (1.02 g, 84%).

(b) 1-(3-Amino-2,6-difluoro-benzoyl)-3-benzyloxy-2-(3-bromophenyl)imidazolidin-4-one This compound was prepared from 3-benzyloxy-2-(3-bromophenyl)-1-(2,6-difluoro-3-nitro-benzoyl)imidazolidin-4-one using zinc/acetic acid according to procedures described in Example 76 to give 945 mg of the title compound (yield: 98%).

(c) N-[3-[3-benzyloxy-2-(3-bromophenyl)-4-oxo-imidazolidine-1-carbonyl]-2,4-difluoro-phenyl]acetamide To a solution of 1-(3-amino-2,6-difluoro-benzoyl)-3-benzyloxy-2-(3-bromophenyl)-imidazolidin-4-one (18 mg, 0.036 mmol) was added triethylamine (7.5 μL, 0.054 mmol) and acetyl chloride (3.8 μL, 0.054 mmol). The reaction mixture was stirred at room temperature o/n. To complete the reaction, additional triethylamine (7.5 μL) and acetyl chloride (3.8 μL) were added. Ethyl acetate was added and the mixture was washed with water, brine, dried over sodium sulfate, filtered and the solvent was removed by evaporation under reduced pressure to give 20 mg of crude N-[3-[3-benzyloxy-2-(3-bromophenyl)-4-oxo-imidazolidine-1-carbonyl]-2,4-difluoro-phenyl]acetamide which was used directly in the next step.

(d) N-[3-[2-(3-bromophenyl)-3-hydroxy-4-oxo-imidazolidine-1-carbonyl]-2,4-difluoro-phenyl]acetamide (Example 77)

This compound was prepared according to the procedure described in Example 69b. Purification was performed using preparative HPLC to afford the title compound (4 mg, 24%). Data: LCMS (B) R$_t$: 7.951 min; m/z 453.9/456.0 (M+H)$^+$ (bromide pattern).

Example 78

N-[3-[2-(3-bromophenyl)-3-hydroxy-4-oxo-imidazolidine-1-carbonyl]-2,4-difluoro-phenyl]methanesulfonamide This compound was prepared in an analogous manner as described for Example 77 starting from Example 77c and methanesulfonyl chloride. Subsequent benzyl-deprotection was performed using boron trifluoride methyl sulfide complex according to the procedure described in Example 69b. Purification was performed using preparative HPLC to afford the title compound (14.6 mg, 83%). Data: LCMS (B) R$_t$: 10.058 min; m/z 487.9/489.9 (M–H)$^-$ (bromide pattern).

Example 79

2-(5-Bromo-3-pyridyl)-1-(2,6-difluorobenzoyl)-3-hydroxy-imidazolidin-4-one

This compound was prepared in an analogous manner as described for Example 65 starting from Intermediate Ab, 5-bromonicotinaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (5 mg, 10%). Data: LCMS (B) R$_t$: 7.565 min; m/z 397.9/400.0 (M+H)$^+$ (bromide pattern).

Example 80

1-(2,6-Difluorobenzoyl)-3-hydroxy-2-(3-methoxyphenyl)imidazolidin-4-one

This compound was prepared in an analogous manner as described for Example 65 starting from Intermediate Ab, 3-methoxybenzaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (28.1 mg, 50%). Data: LCMS (B) R$_t$: 8.123 min; m/z 393.1 (M+HCOOH—H)$^-$.

Example 81

2-(5-Bromo-2-fluoro-phenyl)-1-(2,6-difluorobenzoyl)-3-hydroxy-imidazolidin-4-one This compound was prepared in an analogous manner as described for Example 65 starting from Intermediate Ab, 5-bromo-2-fluorobenzaldehyde and 2,6-difluorobenzoyl chloride. Subsequent benzyl-deprotection was performed using boron trifluoride methyl sulfide complex according to the procedure described in Example 69b. Purification was performed using preparative HPLC to afford the title compound (41 mg, 70%). Data: LCMS (B) R$_t$: 9.797 min; m/z 414.8/416.8 (M+H)$^+$ (bromide pattern).

Example 82

2-(3-Bromophenyl)-3-hydroxy-1-(2,4,6-trifluorobenzoyl)imidazolidin-4-one

This compound was prepared from Intermediate 7 and 2,4,6-trifluorobenzoyl chloride according to the procedure described in Example 1. Purification was performed using preparative HPLC to afford the title compound (24.6 mg, 59%). Data: LCMS (B) R$_t$: 10.381 min; m/z 458.9/461.0 (M+HCOOH—H)$^-$ (bromide pattern).

Example 83

2-(3-Bromophenyl)-3-hydroxy-1-(thiophene-3-carbonyl)imidazolidin-4-one

This compound was prepared from Intermediate 7 and thiophene-3-carbonyl chloride according to the procedure described in Example 1. Purification was performed using preparative HPLC to afford the title compound (17 mg, 46%). Data: LCMS (B) $R_t$: 8.971 min; m/z 367.0/368.9 (M+H)⁺ (bromide pattern).

Example 84

2-(3-Bromophenyl)-1-(2-fluoro-2-methyl-propanoyl)-3-hydroxy-imidazolidin-4-one

This compound was prepared in an analogous manner as described for Example 65 starting from Intermediate Ab, 3-bromobenzaldehyde and 2-fluoro-2-methyl-propanoyl chloride. Subsequent benzyl-deprotection was performed using boron trifluoride methyl sulfide complex according to the procedure described in Example 69b. Purification was performed using preparative HPLC to afford the title compound (31 mg, 45%). Data: LCMS (B) $R_t$: 9.254 min; m/z 345.0/347.0 (M+$^H$(bromide pattern).

Example 85

1-(4-Bromo-2,6-difluoro-benzoyl)-2-(3-bromophenyl)-3-hydroxy-imidazolidin-4-one

This compound was prepared from Intermediate 7 and 4-bromo-2,6-difluoro-benzoyl chloride according to the procedure described in Example 1. Purification was performed using preparative HPLC to afford the title compound (17 mg, 24%). Data: LCMS (B) $R_t$: 11.665 min; m/z 518.8/520.8/522.8 (M+HCOOH—H)⁻ (dibromide pattern).

Example 86

2-(3-Bromophenyl)-1-(3-fluoropyridine-4-carbonyl)-3-hydroxy-imidazolidin-4-one

This compound was prepared in an analogues manner as described for Example 65 starting from Intermediate Ab, 3-bromobenzaldehyde and 3-fluoropyridine-4-carbonyl chloride. Subsequent benzyl-deprotection was performed using boron trifluoride methyl sulfide complex according to the procedure described in Example 69b. Purification was performed using preparative HPLC to afford the title compound (8 mg, 12%). Data: LCMS (B) $R_t$: 7.601 min; m/z 380.0/382.0 (M+H)⁺ (bromide pattern).

Example 87

2-(3-Bromophenyl)-1-(2-fluoropyridine-3-carbonyl)-3-hydroxy-imidazolidin-4-one

This compound was prepared in an analogous manner as described for Example 65 starting from Intermediate Ab, 3-bromobenzaldehyde and 2-fluoropyridine-3-carbonyl chloride. Subsequent benzyl-deprotection was performed using boron trifluoride methyl sulfide complex according to the procedure described in Example 69b. Purification was performed using preparative HPLC to afford the title compound (7 mg, 9%). Data: LCMS (B) $R_t$: 7.837 min; m/z 423.9/425.9 (M+HCOOH—H)⁻ (bromide pattern).

Example 88

2-(3-Bromophenyl)-1-(2-fluoro-6-methyl-benzoyl)-3-hydroxy-imidazolidin-4-one

This compound was prepared in an analogous manner as described for Example 65 starting from Intermediate Ab, 3-bromobenzaldehyde and 2-fluoro-6-methylbenzoyl chloride. Subsequent benzyl-deprotection was performed using boron trifluoride methyl sulfide complex according to the procedure described in Example 69b. Purification was performed using preparative HPLC to afford the title compound (25 mg, 31%). Data: LCMS (B) $R_t$: 10.210 min; m/z 393.0/395.0 (M+H)⁺ (bromide pattern).

Example 89

2-(3-Bromophenyl)-1-(3-fluoropyridine-2-carbonyl)-3-hydroxy-imidazolidin-4-one

This compound was prepared in an analogous manner as described for Example 65 starting from Intermediate Ab, 3-bromobenzaldehyde and 3-fluoropyridine-2-carbonyl chloride. Subsequent benzyl-deprotection was performed using boron trifluoride methyl sulfide complex according to the procedure described in Example 69b. Purification was performed using preparative HPLC to afford the title compound (19 mg, 11%). Data: LCMS (B) $R_t$: 17.875 min; m/z 379.9/381.9 (M+H)⁺ (bromide pattern).

Example 90

2-(3-Bromophenyl)-3-hydroxy-1-(thiophene-2-carbonyl)imidazolidin-4-one

This compound was prepared from Intermediate 7 and thiophene-2-carbonyl chloride according to the procedure described in Example 1. Purification was performed using preparative HPLC to afford the title compound (23 mg, 42%). Data: LCMS (B) $R_t$: 9.304 min; m/z 366.9/368.9 (M+H)⁺ (bromide pattern).

Example 91

2-(3-Bromophenyl)-3-hydroxy-1-(4-phenoxybenzoyl)imidazolidin-4-one

This compound was prepared from Intermediate 7 and 4-phenoxybenzoyl chloride according to the procedure described in Example 1. Purification was performed using preparative HPLC to afford the title compound (17 mg, 25%). Data: LCMS (B) $R_t$: 13.014 min; m/z 453.0/454.9 (M+H)⁺ (bromide pattern).

Example 92

2-(3-Bromophenyl)-1-(furan-2-carbonyl)-3-hydroxy-imidazolidin-4-one

This compound was prepared from Intermediate 7 and furan-3-carbonyl chloride according to the procedure described in Example 1. Purification was performed using preparative HPLC to afford the title compound (9 mg, 17%). Data: LCMS (B) $R_t$: 8.300 min; m/z 350.9/352.9 (M+H)⁺ (bromide pattern).

Example 93

2-(3-Bromophenyl)-3-hydroxy-1-(5-methylthiophene-2-carbonyl)imidazolidin-4-one

This compound was prepared from Intermediate 7 and 5-methylthiophene-2-carbonyl chloride according to the procedure described in Example 1. Purification was performed using preparative HPLC to afford the title compound (1 mg, 2%). Data: LCMS (B) $R_t$: 10.425 min; m/z 381.9/383.0 (M+H)$^+$ (bromide pattern).

Example 94

2-(3-Bromophenyl)-1-(4-ethylthiophene-2-carbonyl)-3-hydroxy-imidazolidin-4-one

This compound was prepared from Intermediate 7 and 4-ethylthiophene-2-carbonyl chloride according to the procedure described in Example 1. Purification was performed using preparative HPLC to afford the title compound (3 mg, 5%). Data: LCMS (B) $R_t$: 11.705 min; m/z 395.0/397.0 (M+H)$^+$ (bromide pattern).

Example 95

2-(3-Bromophenyl)-3-hydroxy-1-(4-phenylbenzoyl)imidazolidin-4-one

This compound was prepared from Intermediate 7 and 4-phenylbenzoyl chloride according to the procedure described in Example 1. Purification was performed using preparative HPLC to afford the title compound (31 mg, 47%). Data: LCMS (B) $R_t$: 12.888 min; m/z 437.0/439.0 (M+H)$^+$ (bromide pattern).

Example 96

2-(3-Bromophenyl)-3-hydroxy-1-(5-isopropylisoxazole-3-carbonyl)imidazolidin-4-one This compound was prepared from Intermediate 7 and 5-isopropylisoxazole-3-carbonyl chloride according to the procedure described in Example 1. Purification was performed using preparative HPLC to afford the title compound (17 mg, 29%). Data: LCMS (B) $R_t$: 11.727 min; m/z 394.0/396.0 (M+H)$^+$ (bromide pattern).

Example 97

2-(3-Bromophenyl)-3-hydroxy-1-[4-(4-methylsulfonylphenyl)benzoyl]imidazolidin-4-one This compound was prepared from Intermediate 7 and 4-(4-methylsulfonylphenyl)benzoyl chloride according to the procedure described in Example 1. Purification was performed using preparative HPLC to afford the title compound (37 mg, 48%). Data: LCMS (B) $R_t$: 10.045 min; m/z 559.0/561.0 (M+HCOOH—H)$^-$ (bromide pattern).

Example 98

1-(2,6-Difluorobenzoyl)-2-(3-ethynylphenyl)-3-hydroxy-imidazolidin-4-one (a) 3-Benzyloxy-2-(3-bromophenyl)-1-(2,6-difluorobenzoyl)imidazolidin-4-one To a suspension of 2-amino-N-benzyloxy-acetamide 2,2,2-trifluoroacetic acid (Intermediate Ab, 10 g, 34 mmol) in acetonitril (50 mL) was added subsequently DiPEA (5.62 mL, 34 mmol) and 3-bromobenzaldehyde (4 mL, 34.3 mmol). The reaction mixture was refluxed for 2 h. The mixture was cooled to room temperature and then placed on an ice-water bath. Additional DiPEA (6.2 mL, 37.4 mmol) was added and a solution of 2,6-difluorobenzoyl chloride (4.5 mL, 35.7 mmol) in acetonitril (5 mL) was added dropwise at 4° C. The reaction mixture was stirred for 15 min allowing to come to room temperature. Ethyl acetate (100 mL) was added to the precipitate formed and the mixture was stirred until a clear solution was obtained. The mixture was washed with water (2×100 mL). The water layer was separated and extracted with ethyl acetate (100 mL). The ethyl acetate layer was washed with 0.2N HCl-solution in water (100 mL), water (100 mL), 0.2N NaOH-solution (100 mL) in water, water (50 mL) and brine (50 mL). The organic phase was dried over sodium sulfate, filtered and partially concentrated under reduced pressure until the first solids appears. Ethyl acetate (50 mL) was added, a slurry formed, and next heptane (100 mL) was added dropwise under thorough stirring. The resulting slurry was stirred at room temperature o/n. The suspension was filtered and the residue was washed with heptane/ethyl acetate=2/1 v/v % (100 mL) and further dried on the filter, collected and dried under high vacuum at 40° C. to give 13.7 g of 3-benzyloxy-2-(3-bromophenyl)-1-(2,6-difluorobenzoyl)-imidazolidin-4-one (yield: 82.7%).

(b) 3-Benzyloxy-1-(2,6-difluorobenzoyl)-2-[3-(2-trimethylsilylethynyl)phenyl]imidazolidin-4-one 3-Benzyloxy-2-(3-bromophenyl)-1-(2,6-difluorobenzoyl)imidazolidin-4-one (200 mg, 0.41 mmol) was dissolved in N,N-dimethylformamide (1.0 L). Under nitrogen atmosphere, trimethylsilylacetylene (289 µL, 2.05 mmol), triethylamine (342 µL, 6.0 mmol) and palladium(II) bis(triphenylphosphine) dichloride (14 mg, 0.05 mmol) were added. The resulting bright yellow suspension was stirred at 70° C. for 1 h. The reaction mixture was added to a stirred mixture of water/brine/ethyl acetate=1/1/1 v/v % (45 mL). The mixture was filtered over Decalite™ and the organic layer was separated, washed with water, brine, dried over sodium sulfate, filtered and concentrated under reduced pressure. The crude residue was purified by column chromatography (heptane to ethyl acetate=100/0 to 1/1 v/v %) to afford 194 mg of the title compound (yield: 94%).

(c) 1-(2,6-Difluorobenzoyl)-2-(3-ethynylphenyl)-3-hydroxy-imidazolidin-4-one (Example 98)

This compound was prepared according to the procedure described in Example 69b starting from 3-benzyloxy-1-(2,6-difluorobenzoyl)-2-[3-(2-trimethylsilylethynyl)phenyl]imidazolidin-4-one. Purification was performed using preparative HPLC to afford the title compound (8 mg, 6%). Data: LCMS (B) $R_t$: 8.964 min; m/z 343.0 (M+H)$^+$.

Example 99

2-(3-Cyclopropylphenyl)-1-(2,6-difluorobenzoyl)-3-hydroxy-imidazolidin-4-one (a) 3-Benzyloxy-2-(3-cyclopropylphenyl)-1-(2,6-difluorobenzoyl)imidazolidin-4-one To a suspension of 3-benzyloxy-2-(3-bromophenyl)-1-(2,6-difluorobenzoyl)imidazolidin-4-one (100 mg, 0.21 mmol) in toluene/water=5/1 v/v % (2.4 mL) was added cyclopropylboronic acid methyliminodiacetic acid anhydride (113 mg, 0.57 mmol) and cesium carbonate (390 mg, 1.2 mmol). The suspension was purged with nitrogen for 3 min. Next, tricyclohexylphosphine (16.8 mg, 0.06 mmol) and palladium(II) acetate (6.7 mg, 0.03 mmol) were added and the reaction mixture was stirred at 100° C. for 3 h. The reaction mixture was added to a stirred mixture of water/brine/ethyl acetate=1/1/1 v/v % (30 mL). The mixture was filtered over Decalite™ and the organic layer was separated, washed with water, brine, dried over sodium sulfate, filtered and concentrated under reduced pressure. The crude residue was purified by column chromatography (heptane to ethyl acetate=1/1 to 0/100 v/v %) to afford 62 mg of the title compound (yield: 62%).

(b) 2-(3-Cyclopropylphenyl)-1-(2,6-difluorobenzoyl)-3-hydroxy-imidazolidin-4-one (Example 99)

This compound was prepared according to the procedure described in Example 69b starting from 3-benzyloxy-2-(3-cyclopropylphenyl)-1-(2,6-difluorobenzoyl)imidazolidin-4-one. Purification was performed using preparative HPLC to afford the title compound (34 mg, 73%). Data: LCMS (B) $R_t$: 10.150 min; m/z 359.1 (M+H)$^+$.

Example 100

2-(3-Bromophenyl)-3-hydroxy-1-(1-methylsulfonylpiperidine-4-carbonyl)imidazolidin-4-one (a) (tert-Butyl 4-chlorocarbonylpiperidine-1-carboxylate 1-tert-Butoxycarbonylpiperidine-4-carboxylic acid (750 mg, 3.27 mmol) was dissolved in dichloromethane (11 mL), 5 drops of DMF were added and the mixture was stirred at 4° C. under nitrogen atmosphere. Thionyl chloride (261 μL, 3.59 mmol) was added and the reaction mixture was stirred for 45 min at 4° C. This mixture was used in the next step without work-up.

(b) tert-Butyl 4-[3-benzyloxy-2-(3-bromophenyl)-4-oxo-imidazolidine-1-carbonyl]piperidine-1-carboxylate This compound was prepared from Intermediate A and tert-butyl 4-chlorocarbonylpiperidine-1-carboxylate according to procedures described in Example 54a. The crude residue was purified by column chromatography (heptane to ethyl acetate=10/0 to 1/9 v/v %) to afford 1.11 g of the title compound (yield: 64%).

(c) 3-Benzyloxy-2-(3-bromophenyl)-1-(piperidine-4-carbonyl)imidazolidin-4-one

To a cold (4° C.) solution of tert-butyl 4-[3-benzyloxy-2-(3-bromophenyl)-4-oxo-imidazolidine-1-carbonyl]piperidine-1-carboxylate (950 mg, 1.7 mmol) in dichloromethane (4 mL) was added TFA (1 mL) and the resulting mixture was stirred for 1.5 h allowing the temperature to come to room temperature. The pH was adjusted by careful addition of aq. sat. NaHCO$_3$-solution until pH~7. Water was added to the mixture followed by DCM/methanol=9/1 v/v %. The organic phase was filtered over a PE filter and concentrated to obtain 895 mg of the title compound as a white foam.

(d) 3-Benzyloxy-2-(3-bromophenyl)-1-(1-methylsulfonylpiperidine-4-carbonyl)imidazolidin-4-one To a cold (4° C.) solution of 3-benzyloxy-2-(3-bromophenyl)-1-(piperidine-4-carbonyl)-imidazolidin-4-one (100 mg, 0.22 mmol) in dichloromethane (1 mL) were added subsequently DiPEA (73.2 μL, 0.42 mmol) and a solution of methanesulfonyl chloride (24.7 μL, 0.33 mmol) in dichloromethane (0.2 mL). The reaction mixture was stirred for 15 min at 4° C. and subsequently 1 h at room temperature. The reaction was quenched by addition of 50% aq. NH$_4$Cl-solution. The mixture was diluted with dichloromethane and the layers were separated. The organic layer was washed with aq. 0.1N HCl-solution, 5% NaHCO$_3$-solution, brine, filtered over a PE filter and concentrated in vacuo to give 89 mg of the title compound (yield: 75%).

(e) 2-(3-Bromophenyl)-3-hydroxy-1-(1-methylsulfonylpiperidine-4-carbonyl)imidazolidin-4-one Example 100

This compound was prepared according to the procedure described in Example 69b starting from 3-benzyloxy-2-(3-bromophenyl)-1-(1-methylsulfonylpiperidine-4-carbonyl) imidazolidin-4-one. Purification was performed using preparative HPLC to afford the title compound (7 mg, 9%). Data: LCMS (B) $R_t$: 7.572 min; m/z 446.0/448.0 (M+H)$^+$ (bromide pattern).

Example 101

4-[2-(3-Bromophenyl)-3-hydroxy-4-oxo-imidazolidine-1-carbonyl]piperidine-1-sulfonamide This compound was prepared from Intermediate A and tert-butyl N-chlorosulfonyl-carbamate according to procedures described in Example 54a and Example 69b. Purification was performed using preparative HPLC to afford the title compound (25 mg, 21%). Data: LCMS (B) $R_t$: 6.569 min; m/z 446.9/449.0 (M+H)$^+$ (bromide pattern).

Example 102

(Trans)-ethyl N-[[4-[2-(3-bromophenyl)-3-hydroxy-4-oxo-imidazolidine-1-carbonyl]cyclohexyl]-methyl] carbamate This compound was prepared from Intermediate A, trans-4-[(tert-butoxycarbonylamino)methyl]cyclohexanecarboxylic acid and ethyl chloroformate according to procedures described in Example 100. Purification was performed using preparative HPLC to afford the title compound (24 mg, 51%). Data: LCMS (B) $R_t$: 9.672 min; m/z 468.0/470.0 (M+H)$^+$ (bromide pattern).

Example 103

2-(3-Bromophenyl)-3-hydroxy-1-(1H-indazole-6-carbonyl)imidazolidin-4-one

This compound was prepared in an analogous manner as described for Example 65 starting from Intermediate Ab, 3-bromobenzaldehyde and 1-tetrahydropyran-2-ylindazole-6-carbonyl chloride. Subsequent benzyl- and tetrahydropyranyl-deprotection was performed using boron trifluoride methyl sulfide complex according to the procedure described in Example 69b. Purification was performed using preparative HPLC to afford the title compound (7 mg, 9%). Data: LCMS (B) $R_t$: 7.875 min; m/z 401.0/403.0 (M+H)$^+$ (bromide pattern).

Example 104

(Trans)-2-(3-bromophenyl)-3-hydroxy-1-(4-phenyl-cyclohexanecarbonyl)imidazolidin-4-one This compound was prepared from Intermediate A and trans-4-phenylcyclohexanecarbonyl chloride according to procedures described in Example 54a and Example 69b. Purification was performed using preparative HPLC to afford the title compound (24 mg, 33%). Data: LCMS (B) $R_t$: 13.604 min; m/z 443.0/445.0 (M+H)$^+$ (bromide pattern).

Example 105

2-(3-Bromophenyl)-1-(4-ethynyl-2,6-difluoro-benzoyl)-3-hydroxy-imidazolidin-4-one This compound was prepared from Intermediate A and 4-ethynyl-2,6-difluoro-benzoic acid (Intermediate 10) according to procedures described in Example 100. Purification was performed using preparative HPLC to afford the title compound (40 mg, 63%). Data: LCMS (B) $R_t$: 9.672 min; m/z 468.0/470.0 (M+H)$^+$ (bromide pattern).

Example 106

2-(3-Bromophenyl)-1-[4-(2-cyclopropylethynyl)-2,6-difluoro-benzoyl]-3-hydroxy-imidazolidin-4-one This compound was prepared from Intermediate 7 and 4-(2-cyclopropylethynyl)-2,6-difluoro-benzoic acid (Intermediate 11) according to procedures described in Example 1 and Example 100a. Purification was performed using preparative HPLC to afford the title compound (47 mg, 50%). Data: LCMS (B) $R_t$: 13.497 min; m/z 461.0/463.0 (M+H)$^+$ (bromide pattern).

Example 107

2-(3-Bromophenyl)-1-[2,6-difluoro-4-(3-methylbut-1-ynyl)benzoyl]-3-hydroxy-imidazolidin-4-one This compound was prepared from Intermediate 7 and 2,6-difluoro-4-(3-methylbut-1-ynyl)benzoic acid (Intermediate 12) according to procedures described in Example 1 and Example 100a. Purification was performed using preparative HPLC to afford the title compound (34 mg, 49%). Data: LCMS (B) $R_t$: 14.494 min; m/z 463.0/465.0 (M+H)$^+$ (bromide pattern).

Example 108

2-(3-Bromophenyl)-1-[4-(2-cyclohexylethynyl)-2,6-difluoro-benzoyl]-3-hydroxy-imidazolidin-4-one This compound was prepared from Intermediate 7 and 4-(2-cyclohexylethynyl)-2,6-difluoro-benzoic acid (Intermediate 13) according to procedures described in Example 1 and Example 100a. Purification was performed using preparative HPLC to afford the title compound (25 mg, 33%). Data: LCMS (B) $R_t$: 16.941 min; m/z 503.0/505.0 (M+H)$^+$ (bromide pattern).

Example 109

1-[4-(3-Aminoprop-1-ynyl)-2,6-difluoro-benzoyl]-2-(3-bromophenyl)-3-hydroxy-imidazolidin-4-one This compound was prepared from Intermediate 7 and 4-[3-(tert-butoxycarbonylamino)prop-1-ynyl]-2,6-difluoro-benzoic acid (Intermediate 14) according to procedures described in Example 1 and Example 100a. Purification was performed, after Boc-deprotection, using preparative HPLC to afford the title compound (7 mg, 19%). Data: LCMS (B) $R_t$: 6.265 min; m/z 449.9/451.9 (M+H)$^+$ (bromide pattern).

Example 110

N-[3-[4-[2-(3-bromophenyl)-3-hydroxy-4-oxo-imidazolidine-1-carbonyl]-3,5-difluoro-phenyl]prop-2-ynyl]methanesulfonamide This compound was prepared from Intermediate 7 and 2,6-difluoro-4-[3-(methanesulfonamido)prop-1-ynyl]benzoic acid (Intermediate 15) according to procedures described in Example 1 and Example 100a. Purification was performed using preparative HPLC to afford the title compound (47 mg, 59%). Data: LCMS (B) $R_t$: 9.554 min; m/z 527.9/529.9 (M+H)$^+$ (bromide pattern).

Example 111

2-(3-Bromophenyl)-1-[2,6-difluoro-4-[3-(sulfamoylamino)prop-1-ynyl]benzoyl]-3-hydroxy-4-oxo-imidazolidine This compound was prepared from Intermediate 7 and 4-[3-(tert-butoxycarbonylsulfamoylamino)prop-1-ynyl]-2,6-difluoro-benzoic acid (Intermediate 16) according to procedures described in Example 1 and Example 100a. Purification was performed, after Boc-deprotection, using preparative HPLC to afford the title compound (12 mg, 25%). Data: LCMS (B) $R_t$: 8.710 min; m/z 572.9/574.9 (M+HCOOH—H)$^-$ (bromide pattern).

Example 112

1-[4-(3-Amino-3-methyl-but-1-ynyl)-2,6-difluoro-benzoyl]-2-(3-bromophenyl)-3-hydroxy-imidazolidin-4-one This compound was prepared from Intermediate 7 and 4-[3-(tert-butoxycarbonylamino)-3-methyl-but-1-ynyl]-2,6-difluoro-benzoic acid (Intermediate 17) according to procedures described in Example 1 and Example 100a. Purification was performed, after Boc-deprotection, using preparative HPLC to afford the title compound (5 mg, 7%). Data: LCMS (B) $R_t$: 7.235 min; m/z 522.0/524.0 (M+HCOOH—H)$^-$ (bromide pattern).

Example 113

N-[3-[4-[2-(3-bromophenyl)-3-hydroxy-4-oxo-imidazolidine-1-carbonyl]-3,5-difluoro-phenyl]-1,1-dimethyl-prop-2-ynyl]acetamide To a cold (4° C.) solution of 1-[4-(3-amino-3-methyl-but-1-ynyl)-2,6-difluoro-benzoyl]-2-(3-bromophenyl)-3-hydroxy-imidazolidin-4-one (Example 112, 40 mg, 0.08 mmol) in DCM (2 mL) were added subsequently DiPEA (69.8 μL, 0.40 mmol) and a solution of acetyl chloride (17.1 μL, 0.24 mmol) in DCM (0.2 mL). The reaction mixture was stirred for 1 h at 4° C. 1-Methylpiperazine (88 μL, 0.4 mmol) was added and the reaction mixture was stirred for 15 min at 4° C. DCM was added to the mixture and the pH was adjusted to pH<2 by addition of a 2N HCl-solution. The layers were separated and the organic layer was washed with 2N HCl-solution and brine, then filtered over a PE filter and concentrated in vacuo. Purification was performed using preparative HPLC to afford the title compound (11 mg, 26%). Data: LCMS (B) $R_t$: 10.058 min; m/z 520.0/522.0 (M+H)+ (bromide pattern).

Example 114

2-(3-Bromophenyl)-1-(4-cyclopropyl-2,6-difluoro-benzoyl)-3-hydroxy-imidazolidin-4-one This compound was prepared from Intermediate 7 and 4-cyclopropyl-2,6-difluoro-benzoic acid (Intermediate 18) according to procedures described in Example 1 and Example 100a. Purification was performed using preparative HPLC to afford the title compound (18 mg, 27%). Data: LCMS (B) $R_t$: 12.013 min; m/z 437.0/439.0 (M+H)+ (bromide pattern).

Example 115

2-(3-Bromophenyl)-1-(2,6-difluoro-4-vinyl-benzoyl)-3-hydroxy-imidazolidin-4-one

This compound was prepared from Intermediate 7 and 2,6-difluoro-4-vinyl-benzoic acid (Intermediate 19) according to procedures described in Example 1 and Example 100a. Purification was performed using preparative HPLC to afford the title compound (22 mg, 35%). Data: LCMS (B) $R_t$: 11.466 min; m/z 422.9/424.9 (M+H)+ (bromide pattern).

Example 116

2-(3-Bromophenyl)-1-(2,6-difluoro-4-methyl-benzoyl)-3-hydroxy-imidazolidin-4-one This compound was prepared from Intermediate 7 and 2,6-difluoro-4-methyl-benzoic acid (Intermediate 20) according to procedures described in Example 1 and Example 100a. Purification was performed using preparative HPLC to afford the title compound (21 mg, 34%). Data: LCMS (B) $R_t$: 10.826 min; m/z 410.9/412.9 (M+H)+ (bromide pattern).

Example 117

2-(3-Bromophenyl)-1-(2,6-difluoro-4-phenyl-benzoyl)-3-hydroxy-imidazolidin-4-one This compound was prepared from Intermediate A and 2,6-difluoro-4-phenyl-benzoic acid (Intermediate 21) according to procedures described in Example 54 and Example 69b. Purification was performed using preparative HPLC to afford the title compound (63 mg, 67%). Data: LCMS (B) $R_t$: 13.344 min; m/z 472.9/474.9 (M+H)+ (bromide pattern).

Example 118

2-(3-Bromophenyl)-1-[2,6-difluoro-4-(4-pyridyl)benzoyl]-3-hydroxy-imidazolidin-4-one This compound was prepared from Intermediate 7 and 2,6-difluoro-4-(4-pyridyl)benzoic acid (Intermediate 22) according to procedures described in Example 1 and Example 100a. Purification was performed using preparative HPLC to afford the title compound (20 mg, 28%). Data: LCMS (B) $R_t$: 7.015 min; m/z 474.0/476.0 (M+H)+ (bromide pattern).

Example 119

2-(3-Bromophenyl)-1-[2,6-difluoro-4-(1-methyl-pyrazol-4-yl)benzoyl]-3-hydroxy-imidazolidin-4-one This compound was prepared from Intermediate 7 and 2,6-difluoro-4-(1-methylpyrazol-4-yl)benzoic acid (Intermediate 23) according to procedures described in Example 1 and Example 100a. Purification was performed using preparative HPLC to afford the title compound (1 mg, 1%). Data: LCMS (B) $R_t$: 9.358 min; m/z 477.0/478.9 (M+H)+ (bromide pattern).

Example 120

2-(3-Bromophenyl)-1-[2,6-difluoro-4-(2-thienyl)benzoyl]-3-hydroxy-imidazolidin-4-one This compound was prepared from Intermediate 7 and 2,6-difluoro-4-(2-thienyl)benzoic acid (Intermediate 24) according to procedures described in Example 1 and Example 100a. Purification was performed using preparative HPLC to afford the title compound (12 mg, 17%). Data: LCMS (B) $R_t$: 12.863 min; m/z 478.9/480.9 (M+H)+ (bromide pattern).

Example 121

2-(3-Bromophenyl)-1-[2,6-difluoro-4-(5-fluoro-2-thienyl)benzoyl]-3-hydroxy-imidazolidin-4-one This compound was prepared from Intermediate 7 and 2,6-difluoro-4-(5-fluoro-2-thienyl)benzoic acid (Intermediate 25) according to procedures described in Example 1 and Example 100a. Purification was performed using preparative HPLC to afford the title compound (10 mg, 13%). Data: LCMS (B) $R_t$: 13.726 min; m/z 496.9/498.9 (M+H)+ (bromide pattern).

Example 122

2-(3-Bromophenyl)-1-[2,6-difluoro-4-(1,3,5-trimethylpyrazol-4-yl)benzoyl]-3-hydroxy-imidazolidin-4-one This compound was prepared from Intermediate 7 and 2,6-difluoro-4-(1,3,5-trim ethylpyrazol-4-yl)benzoic acid (Intermediate 26) according to procedures described in Example 1 and Example 100a. Purification was performed using preparative HPLC to afford the title compound (4 mg, 5%). Data: LCMS (B) $R_t$: 9.900 min; m/z 505.0/507.0 (M+H)+ (bromide pattern).

Example 123

2-(3-Bromophenyl)-1-[2,6-difluoro-4-(3-pyridyl)benzoyl]-3-hydroxy-imidazolidin-4-one This compound was prepared from Intermediate 7 and 2,6-difluoro-4-(3-pyridyl)benzoic acid (Intermediate 27) according to procedures described in Example 1 and Example 100a. Purification was performed using preparative

Example 124

1-[(2-Fluorophenyl)methyl]-3-hydroxy-2-(3-iodo-phenyl)imidazolidin-4-one (a) 2-[(2-Fluorophenyl)methylamino]ethanehydroxamic Acid A solution of 2-fluorobenzaldehyde (351 µL, 3.33 mmol) in methanol (7 mL) was added to a solution of 2-aminoethanehydroxamic acid (300 mg, 3.33 mmol) in water (1.33 mL) and a 2N NaOH-solution in water (1.66 mL, 3.33 mmol). The reaction mixture was stirred for 5 min at room temperature after which precipitation occurred. $NaBH_4$ (126 mg, 3.33 mmol) was added and the reaction mixture was stirred for 30 min at room temperature. Methanol was removed by evaporation under reduced pressure and the resulting solution was diluted by addition of water. After addition of 2M HCl-solution till pH~7, dichloromethane/methanol=9/1 v/v % was added to the solution. The organic layer was then separated over a PE filter and concentrated in vacuo. The crude residue was purified by column chromatography (dichloromethane to methanol=9/1 to 8/2 v/v %) to afford 128 mg of the title compound (yield: 19%).

(b) 1-[(2-Fluorophenyl)methyl]-3-hydroxy-2-(3-iodophenyl)imidazolidin-4-one (Example 124)

To a solution 2-[(2-fluorophenyl)methylamino]ethanehydroxamic acid (25 mg, 0.126 mmol) in ethanol (2 mL) was added 3-iodobenzaldehyde (29 mg, 0.126 mmol) and the reaction mixture was stirred at reflux temperature for 1 h. The solvent was evaporated under reduced pressure. The crude residue was purified by column chromatography (heptane to ethyl acetate=10/0 to 2/8 v/v). Purification was performed using preparative HPLC to afford the title compound (25 mg, 48%). Data: LCMS (B) $R_t$: 12.953 min; m/z 413.0 (M+H)$^+$.

Example 125

2-(3-Bromophenyl)-1-[(2-fluorophenyl)methyl]-3-hydroxy-imidazolidin-4-one

This compound was prepared according to procedures described in Example 124 starting from 2-[(2-fluorophenyl)methylamino]ethanehydroxamic acid and 3-bromobenzaldehyde. Purification was performed using preparative HPLC to afford the title compound (53 mg, 54%). Data: LCMS (A) $R_t$: 4.536 min; m/z 365.0/367.0 (M+H)$^+$ (bromide pattern).

Example 126

2-(3-Bromo-4-fluoro-phenyl)-1-[(2-fluorophenyl)methyl]-3-hydroxy-imidazolidin-4-one This compound was prepared according to procedures described in Example 124 starting from 2-[(2-fluorophenyl)methylamino]ethanehydroxamic acid and 3-bromo-4-fluorobenzaldehyde. Purification was performed using preparative HPLC to afford the title compound (11.5 mg, 24%). Data: LCMS (B) $R_t$: 12.791 min; m/z 383.0/385.0 (M+H)$^+$ (bromide pattern).

HPLC to afford the title compound (18 mg, 25%). Data: LCMS (B) $R_t$: 8.169 min; m/z 474.0/476.0 (M+H)$^+$ (bromide pattern).

Example 127

2-(3-Bromophenyl)-1-[(2,6-difluorophenyl)methyl]-3-hydroxy-imidazolidin-4-one

This compound was prepared according to procedures described in Example 124 starting from 2-[(2,6-difluorophenyl)methylamino]ethanehydroxamic acid and 3-bromobenzaldehyde. Purification was performed using preparative HPLC to afford the title compound (29 mg, 45%). Data: LCMS (B) $R_t$: 12.422 min; m/z 383.0/385.0 (M+H)$^+$ (bromide pattern).

Example 128

2-(3-Bromophenyl)-1-[2,6-difluoro-4-[3-methyl-3-(sulfamoylamino)but-1-ynyl]benzoyl]-3-hydroxy-4-oxo-imidazolidine This compound was prepared from Intermediate 7 and 4-[3-(tert-butoxycarbonylsulfamoylamino)-3-methyl-but-1-ynyl]-2,6-difluoro-benzoic acid (Intermediate 28) according to procedures described in Example 1 and Example 100a. Purification was performed, after Boc-deprotection, using preparative HPLC to afford the title compound (10 mg, 15%). Data: LCMS (B) $R_t$: 9.972 min; m/z 555.0/557.0 (M+HCOOH—H)$^-$ (bromide pattern).

Example 129

1-(2,6-Difluorobenzoyl)-3-hydroxy-2-(3-vinylphenyl)imidazolidin-4-one

This compound was prepared from Intermediate 29 and 2,6-difluorobenzoyl chloride according to procedures described in Example 1. Purification was performed using preparative HPLC to afford the title compound (24 mg, 31.7%). Data: LCMS (B) $R_t$: 9.526 min; m/z 345.1 (M+H)$^+$.

Example 130

N-[[4-[2-(3-bromophenyl)-3-hydroxy-4-oxo-imidazolidine-1-carbonyl]-3,5-difluoro-phenyl]methyl]methanesulfonamide This compound was prepared from Intermediate 7 and 2,6-difluoro-4-(methanesulfonamidomethyl)benzoic acid (Intermediate 30) according to procedures described in Example 1 and Example 100a. Purification was performed using preparative HPLC to afford the title compound (27 mg, 36%). Data: LCMS (B) $R_t$: 8.247 min; m/z 503.9/505.9 (M+H)$^+$ (bromide pattern).

Example 131

2-(3-Bromophenyl)-1-[4-(2-cyclohexylethyl)-2,6-difluoro-benzoyl]-3-hydroxy-imidazolidin-4-one This compound was prepared from Intermediate 7 and 4-(2-cyclohexylethyl)-2,6-difluoro-benzoic acid (Intermediate 31) according to procedures described in Example 1 and Example 100a. Purification was performed using preparative HPLC to afford the title compound (34 mg, 45%). Data: LCMS (B) $R_t$: 17.712 min; m/z 507.0/509.0 (M+H)$^+$ (bromide pattern).

Example 132

2-(3-Bromophenyl)-1-[2,6-difluoro-4-[3-(sulfamoylamino)propyl]benzoyl]-3-hydroxy-4-oxo-imidazolidine This compound was prepared from Intermediate 7 and 4-[3-(tert-butoxycarbonylsulfamoylamino)propyl]-2,6-difluoro-benzoic acid (Intermediate 32) according to procedures described in Example 1 and Example 100a. Purification was performed, after Boc-deprotection, using preparative HPLC to afford the title compound (5 mg, 19%). Data: LCMS (B) $R_t$: 8.470 min; m/z 533.0/535.0 (M+H)$^+$ (bromide pattern).

Example 133

2-(3-Bromophenyl)-1-(2,6-difluoro-4-morpholinobenzoyl)-3-hydroxy-imidazolidin-4-one This compound was prepared from Intermediate 7 and 2,6-difluoro-4-morpholino-benzoic acid (Intermediate 33) according to procedures described in Example 1 and Example 100a. Purification was performed using preparative HPLC to afford the title compound (29 mg, 60%). Data: LCMS (B) $R_t$: 9.848 min; m/z 482.0/484.0 (M+H)$^+$ (bromide pattern).

Example 134

1-[4-(Azetidin-1-yl)-2,6-difluoro-benzoyl]-2-(3-bromophenyl)-3-hydroxy-imidazolidin-4-one This compound was prepared from Intermediate 7 and 4-(azetidin-1-yl)-2,6-difluoro-benzoic acid (Intermediate 34) according to procedures described in Example 1 and Example 100a. Purification was performed using preparative HPLC to afford the title compound (3.8 mg, 2.9%). Data: LCMS (B) $R_t$: 11.410 min; m/z 452.0/454.0 (M+H)$^+$ (bromide pattern).

Example 135

2-(3-Bromophenyl)-1-[2,6-difluoro-4-[2-hydroxyethyl(methyl)amino]benzoyl]-3-hydroxy-imidazolidin-4-one This compound was prepared from Intermediate A and 4-[2-benzyloxyethyl(methyl)amino]-2,6-difluoro-benzoic acid (Intermediate 35) according to procedures described in Example 100a, Example 54a and Example 58b. Purification was performed using preparative HPLC to afford the title compound (13 mg, 8%). Data: LCMS (B) $R_t$: 8.599 min; m/z 470.0/472.0 (M+H)$^+$ (bromide pattern).

Example 136

2-(3-Bromophenyl)-1-[2,6-difluoro-4-[(2S)-2-(hydroxymethyl)pyrrolidin-1-yl]benzoyl]-3-hydroxy-imidazolidin-4-one This compound was prepared from Intermediate A and 2,6-difluoro-4-[(2S)-2-(hydroxymethyl)pyrrolidin-1-yl]benzoic acid (Intermediate 36) according to procedures described in Example 100a and Example 54a. Purification was performed, after benzyl-deprotection with hydrogenation using platinumoxide according to the procedure described in Example 54b, using preparative HPLC to afford the title compound (5.9 mg, 40%). Data: LCMS (B) $R_t$: 9.794 min; m/z 496.0/498.0 (M+H)$^+$ (bromide pattern).

Example 137

4-[2-(3-Bromophenyl)-3-hydroxy-4-oxo-imidazolidine-1-carbonyl]-3,5-difluoro-N-(2-methoxyethyl)benzamide This compound was prepared from Intermediate 7 and 2,6-difluoro-4-(2-methoxyethylcarbamoyl)benzoic acid (Intermediate 37) according to procedures described in Example 1 and Example 100a. Purification was performed using preparative HPLC to afford the title compound (10 mg, 4.4%). Data: LCMS (B) $R_t$: 8.205 min; m/z 498.0/500.0 (M+H)$^+$ (bromide pattern).

Example 138

6-Bromo-3-[2-(3-bromophenyl)-3-hydroxy-4-oxo-imidazolidine-1-carbonyl]-2,4-difluoro-N-(2-methoxyethyl)benzamide This compound was isolated during prep HPLC purification of Example 137 (26 mg, 10%). Data: LCMS (B) $R_t$: 9.335 min; m/z 577.9 (M+H)$^+$ (dibromide pattern).

Example 139a and Example 139b 2-(3-Bromophenyl)-3-hydroxy-1-[(1S)-1-phenylethyl]imidazolidin-4-one (Isomer 1 and Isomer 2)

This compound was prepared in an analogous manner as described for Intermediate 2, starting from Intermediate 38 and 3-bromobenzaldehyde to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 139a, isomer 1, 2.7 mg, 7.5%). Data: LCMS (B) $R_t$: 12.866 min; m/z 361.0/363.0 (M+H)$^+$ (bromide pattern). Example 139b, isomer 2, 3 mg, 8.3%). Data: LCMS (B) $R_t$: 13.375 min; m/z 361.0/363.0 (M+H)$^+$ (bromide pattern).

Example 140a and Example 140b

3-Hydroxy-2-(3-iodophenyl)-1-[(1S)-1-phenylethyl]imidazolidin-4-one (Isomer 1 and Isomer 2)

This compound was prepared in an analogous manner as described for Intermediate 2, starting from Intermediate 38 and 3-iodobenzaldehyde to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 140a, isomer 1, 12.2 mg, 6%). Data: LCMS (B) $R_t$: 13.273 min; m/z 409.0 (M+H)$^+$. Example 140b, isomer 2, 48 mg, 23%). Data: LCMS (B) R$_t$: 13.782 min; m/z 409.0 (M+H)$^+$.

Example 141a and Example 141b 2-(3-Bromophenyl)-1-[1-(2,6-difluorophenyl)ethyl]-3-hydroxy-imidazolidin-4-one (Diastereomeric Pair 1 and Diastereomeric Pair 2)

This compound was prepared in an analogous manner as described for Intermediate 2, starting from Intermediate 39 and 3-bromobenzaldehyde to afford the title compound as a mixture of four diastereomers.

The mixture of the four diastereomers was separated by preparative HPLC to afford the two separate diastereomers as pairs of enantiomers (enantiomeric pair 1, first eluting from the column, less active isomer, and enantiomeric pair 2, last eluting, most active isomer). Example 141a, diastereomeric pair 1, 4.6 mg, 3%). Data: LCMS (B) R$_t$: 12.618 min; m/z 397.0/399.0 (M+H)$^+$ (bromide pattern). Example 142b, diastereomeric pair 2, 14 mg, 11%). Data: LCMS (B) R$_t$: 13.610 min; m/z 397.0/399.0 (M+H)$^+$ (bromide pattern).

Separation of Enantiomers of Example 27

Example 142a and Example 142b 2-(3-Bromophenyl)-1-(2,6-difluorobenzoyl)-3-hydroxy-imidazolidin-4-one (Isomer 1 and Isomer 2)

These diastereomers were prepared in an analogous manner as described for Example 63a and 63b starting from Example 17 and (2S)-2-methoxy-2-phenyl-acetyl chloride.

The mixture of the two diastereomers was separated by column chromatography (toluene/diethyl ether=4/1 v/v % isocratic) to afford the two separate diastereomers (diastereomer 1, first eluting from the column obtained in 87 mg and diastereomer 2, last eluting in 23 mg). $^1$H-NMR showed for diastereomer 1>90% de and for diastereomer 2>80% de.

Both diastereomers were reacted separately with morpholine according to the procedure as described in Example 63. Enantiomeric enriched compounds were obtained after purification using preparative HPLC to afford Example 142a, 2-(3-bromophenyl)-1-(2,6-difluorobenzoyl)-3-hydroxy-imidazolidin-4-one (isomer 1, less active isomer, 44 mg, 69%) and Example 142b, 2-(3-bromophenyl)-1-(2,6-difluorobenzoyl)-3-hydroxy-imidazolidin-4-one (isomer 2, most active isomer, 14 mg, 84%). Data: Example 142a LCMS (B) R$_t$: 8.899 min; m/z 397.0/399.0 (M+H)$^+$ (bromide pattern). Example 142b LCMS (B) R$_t$: 8.963 min; m/z 397.0/399.0 (M+H)$^+$ (bromide pattern).

Separation of Enantiomers of Example 45

Example 143a and Example 143b 2-(3-Bromo-4-fluoro-phenyl)-1-(2-chloro-6-fluoro-benzoyl)-3-hydroxy-imidazolidin-4-one (Isomer 1 and Isomer 2)

These diastereomers were prepared in an analogous manner as described for Example 63a and 63b starting from Example 45 and (2S)-2-phenylbutanoic acid.

The mixture of the two diastereomers was separated by column chromatography (toluene/ethyl acetate=97/3 v/v % isocratic) to afford the two separate diastereomers (diastereomer 1, first eluting from the column obtained in 12 mg (yield: 43%) and diastereomer 2, last eluting in 10 mg (yield: 36%)). $^1$H-NMR showed for diastereomer 1>80% de and for diastereomer 2>80% de.

Both diastereomers were reacted separately with 1-methylpiperazine according to the procedure as described in Example 63. Enantiomeric enriched compounds were obtained after purification using preparative HPLC to afford Example 143a, 2-(3-bromo-4-fluoro-phenyl)-1-(2-chloro-6-fluoro-benzoyl)-3-hydroxy-imidazolidin-4-one (isomer 1, less active isomer, 8.3 mg, 69%) and Example 143b, 2-(3-bromo-4-fluoro-phenyl)-1-(2-chloro-6-fluoro-benzoyl)-3-hydroxy-imidazolidin-4-one (isomer 2, most active isomer, 6 mg, 77%). Data: Example 142a LCMS (B) R$_t$: 10.451 min; m/z 474.9/476.9 (M+HCOOH—H)$^-$ (bromide/chloride pattern). Example 142b LCMS (B) R$_t$: 10.456 min; m/z 474.9/476.9 (M+HCOOH—H)$^-$ (bromide/chloride pattern).

Separation of Enantiomers of Example 106

Example 144a and Example 144b 2-(3-Bromophenyl)-1-[4-(2-cyclopropylethynyl)-2,6-difluoro-benzoyl]-3-hydroxy-imidazolidin-4-one (Isomer 1 and Isomer 2)

These diastereomers were prepared in an analogous manner as described for Example 63a and 63b starting from Example 106 and (2S)-2-phenylbutanoic acid.

The mixture of the two diastereomers was separated by column chromatography (toluene/ethyl acetate=97/3 v/v % isocratic) to afford the two separate diastereomers (diastereomer 1, first eluting from the column obtained in 12 mg (yield: 22%) and diastereomer 2, last eluting in 8 mg (yield: 15%)). $^1$H-NMR showed for diastereomer 1>80% de and for diastereomer 2>80% de.

Both diastereomers were reacted separately with 1-methylpiperazine according to the procedure as described in Example 63. Enantiomeric enriched compounds were obtained after purification using preparative HPLC to afford Example 144a, 2-(3-bromophenyl)-1-[4-(2-cyclopropylethynyl)-2,6-difluoro-benzoyl]-3-hydroxy-imidazolidin-4-one (isomer 1, less active isomer, 8.3 mg, 69%) and Example 144b, 2-(3-bromophenyl)-1-[4-(2-cyclopropylethynyl)-2,6-difluoro-benzoyl]-3-hydroxy-imidazolidin-4-one (isomer 2, most active isomer, 4.9 mg, 66%). Data: Example 144a LCMS (B) R$_t$: 13.425 min; m/z 461.0/463.0 (M+H)$^+$ (bromide pattern). Example 144b LCMS (B) R$_t$: 13.413 min; m/z 461.0/463.0 (M+H)$^+$ (bromide pattern).

Separation of Enantiomers of Example 127

Example 145a and Example 145b 2-(3-Bromophenyl)-1-[(2,6-difluorophenyl)methyl]-3-hydroxy-imidazolidin-4-one (Isomer 1 and Isomer 2)

These diastereomers were prepared in an analogous manner as described for Example 63a and 63b starting from Example 127 and (2S)-2-phenylbutanoic acid.

The mixture of the two diastereomers was separated by column chromatography (toluene/ethyl acetate=97/3 v/v % isocratic) to afford the two separate diastereomers (diastereomer 1, first eluting from the column obtained in 7 mg (yield: 22%) and diastereomer 2, last eluting in 7 mg (yield: 22%)). $^1$H-NMR showed for diastereomer 1>80% de and for diastereomer 2>80% de.

Both diastereomers were reacted separately with 1-methylpiperazine according to the procedure as described in Example 63. Enantiomeric enriched compounds were obtained after purification using preparative HPLC to afford Example 145a, 2-(3-bromophenyl)-1-[(2,6-difluorophenyl)methyl]-3-hydroxy-imidazolidin-4-one (isomer 1, less active isomer, 4.3 mg, 86%) and Example 145b, 2-(3-bromophenyl)-1-[(2,6-difluorophenyl)methyl]-3-hydroxy-imidazolidin-4-one (isomer 2, most active isomer, 3.7 mg, 74%). Data: Example 145a LCMS (B) $R_t$: 12.382 min; m/z 383.0/385.0 (M+H)$^+$ (bromide pattern). Example 145b LCMS (B) $R_t$: 12.374 min; m/z 383.0/385.0 (M+H)$^+$ (bromide pattern).

Separation of Enantiomers of Example 124

Example 146a and Example 146b

1-[(2-fluorophenyl)methyl]-3-hydroxy-2-(3-iodophenyl)imidazolidin-4-one (Isomer 1 and Isomer 2)

These diastereomers were prepared in an analogous manner as described for Example 63a and 63b starting from Example 124 and (2S)-2-phenylbutanoic acid.

The mixture of the two diastereomers was separated by column chromatography (toluene/ethyl acetate=97/3 v/v % isocratic) to afford the two separate diastereomers (diastereomer 1, first eluting from the column obtained in 26 mg (yield: 19%) and diastereomer 2, last eluting in 27 mg (yield: 20%)). $^1$H-NMR showed for diastereomer 1>80% de and for diastereomer 2>80% de.

Both diastereomers were reacted separately with 1-methylpiperazine according to the procedure as described in Example 63. Enantiomeric enriched compounds were obtained after purification using preparative HPLC to afford Example 146a, 1-[(2-fluorophenyl)methyl]-3-hydroxy-2-(3-iodophenyl)imidazolidin-4-one (isomer 1, less active isomer, 32.5 mg, 69%) and Example 146b, 1-[(2-fluorophenyl)methyl]-3-hydroxy-2-(3-iodophenyl)imidazolidin-4-one (isomer 2, most active isomer, 19 mg, 56%). Data: Example 146a LCMS (B) $R_t$: 12.921 min; m/z 413.0 (M+H)$^+$. Example 146b LCMS (B) $R_t$: 12.920 min; m/z 413.0 (M+H)$^+$ (bromide pattern).

Separation of Enantiomers of Example 111

Example 147a and Example 147b 2-(3-Bromophenyl)-1-[2,6-difluoro-4-[3-(sulfamoylamino)prop-1-ynyl]benzoyl]-3-hydroxy-4-oxo-imidazolidine (Isomer 1 and Isomer 2)

These diastereomers were prepared in an analogous manner as described for Example 63a and 63b starting from Example 111 and (2S)-2-phenylbutanoic acid.

The mixture of the two diastereomers was separated by column chromatography (toluene/ethyl acetate=85/15 v/v % isocratic) to afford the two separate diastereomers (diastereomer 1, first eluting from the column obtained in 41.4 mg (yield: 30%) and diastereomer 2, last eluting in 32 mg (yield: 23.2%)). $^1$H-NMR showed for diastereomer 1>80% de and for diastereomer 2>80% de.

Diastereomer 2 was reacted with 1-methylpiperazine according to the procedure as described in Example 63. Enantiomeric enriched compound was obtained, after Boc-deprotection and after purification using preparative HPLC to afford Example 147b, 2-(3-bromophenyl)-1-[2,6-difluoro-4-[3-(sulfamoylamino)prop-1-ynyl]benzoyl]-3-hydroxy-4-oxo-imidazolidine (isomer 2, most active isomer, 15.3 mg, 60%). Data: Example 147b LCMS (A) $R_t$: 4.691 min; m/z 572.9/574.9 (M+HCOOH—H)$^-$ (bromide pattern).

Example 148

Biochemical IDO1 Assay

To determine the inhibitory activity of compounds on IDO1, the NFK GreenScreen™ assay was used, which makes use of a chemical probe to detect NFK (Seegers, N., et al., J. Biol. Screen. 19: 1266; 2014). Compounds were serially diluted in dimethylsulfoxide (DMSO) and finally in IDO1 reaction buffer, consisting of 50 mM NaH$_2$PO$_4$, pH7.0, supplemented with 0.05% Tween-20 (cat. No. P7949; Sigma Aldrich) and 1% glycerol. Recombinant full-length IDO1 (Seegers, N., et al.) and all other assay components were diluted in IDO1 reaction buffer. 10 μl of compound solution, 20 μl of enzyme solution supplemented with 20 mM ascorbic acid, 20 μg/ml catalase, and 20 μM methylene blue were combined in the well of a black 384-well plate (cat. no. 3573; Corning, Corning, N.Y., USA) and incubated for 30 min at room temperature. Subsequently, 10 μl of 0.4 mM of the substrate L-tryptophan was added, i.e., the final concentration of L-tryptophan was 100 μM. The DMSO concentration in the assay was 0.3%. The concentration of IDO1 was 25 nM. Incubation was continued for 60 min at room temperature. Then, 10 μl of NFK Green™ (NTRC, Oss, The Netherlands) was added, the plate was sealed, and the reaction was developed for 3 hours at 37° C. To determine the production of N-formyl kynurenine (NFK), the seal was removed and fluorescence was read on an EnVision multimode reader (Perkin Elmer, Waltham, Mass., USA). IC$_{50}$ were calculated using XLfit™ software (ID Business Solutions, Ltd., Surrey, U.K.). The IC$_{50}$ of 1-MT in this assay is >100 μM. The IC$_{50}$ values of all exemplified compounds were found to be smaller than 25 μM. Compounds of examples 1, 2, 7, 8, 10, 14, 16, 17, 18, 20, 23, 24, 25, 28, 29, 30, 31, 38, 39, 40, 43, 47, 48, 50, 57, 60, 61, 63b, 64, 65, 69, 70, 74, 78, 88, 89, 90, 91, 96, 97, 99, 100, 101, 102, 103, 112, 113, 121, 123, 131, 134, 135, 140a, 142a and 143a showed an IC$_{50}$ value >1 μM and <5 μM and compounds of examples 3, 4, 9, 13, 15, 26, 27, 32, 33, 34, 35, 36, 37, 44, 45, 46, 51, 52, 53, 54, 59, 62, 63a, 66, 67, 71, 72, 73, 75, 76, 77, 82, 85, 86, 87, 98, 105, 106, 107, 108, 109, 110, 111, 114, 115, 116, 117, 118, 119, 120, 124, 125, 126, 127, 128, 129, 130, 132, 137, 138, 139b, 140b, 141b, 142b, 143b, 144a, 144b, 145a, 145b, 146a, 146b and 147b showed an IC$_{50}$ of <1 μM.

Example 149

Cell-Based Assay for IDO1

A-375 melanoma cells were purchased from LGC Standards GmbH (Wesel, Germany) and cultured in DMEM tissue culture medium (Life Technologies, Bleiswijk, The Netherlands), supplemented with 10% (v/v) bovine calf serum. Compounds were dissolved in DMSO and diluted in DMEM. Final DMSO concentration in the assay was 0.4% (v/v). Eight thousand cells per well in 35 μl were seeded in a black 384-well tissue plate (cat. No. 781086; Greiner Bio-One GmbH, Frickenhausen, Germany) and allowed to adhere by incubation at 37° C., 95% humidity, and 5% CO$_2$ overnight. Then, 5 μl of compound solution was added to the cells 1 hour prior to stimulation with 5 μl of 500 ng/ml interferon-γ (R&D Systems, Minneapolis, Minn., USA) diluted in DMEM medium. At the same time, 5 µl of L-tryptophan in 20 mM Hepes buffer pH 7.4 was added. Incubation was continued for 48 hours. To determine NFK levels, 12 µl NFK Green™ (NTRC, Oss, The Netherlands) was added to each well, and the plate was sealed and incubated for 4 hours at 37° C. Fluorescence was measured on an EnVision multimode reader (Perkin Elmer, Waltham, Mass., USA). $IC_{50}$ were calculated using XLfit™ software (ID Business Solutions, Ltd., Surrey, U.K.). Compounds of examples 2, 3, 4, 7, 9, 10, 13, 15, 17, 25, 26, 27, 32, 33, 34, 35, 39, 43, 44, 45, 46, 51, 52, 53, 54, 59, 62, 66, 67, 71, 72, 73, 76, 82, 85, 86, 87, 98, 99, 105, 106, 107, 108, 114, 115, 116, 118, 119, 120, 124, 125, 127, 129, 137, 138, 139b, 140a, 140b, 141b, 142a and 142b showed an $IC_{50}$ value of <5 µM Example 150

Biochemical Assay for TDO

The NFK GreenScreen™ assay was also used to determine the inhibitory activity of compounds on TDO (Seegers, N., et al., J. Biol. Screen. 19: 1266; 2014). Compounds were serially diluted in DMSO and finally in TDO reaction buffer, consisting of 100 mM $NaH_2PO_4$, pH 7.0, supplemented with 0.01% Tween-20 (cat. No. P7949; Sigma Aldrich). Recombinant TDO (Seegers, N., et al.) and all other assay components were diluted in TDO reaction buffer. 10 µl of compound solution and 20 µl of enzyme solution supplemented with 200 µM ascorbic acid were combined in the well of a black 384-well plate (cat. no. 3573; Corning, Corning, N.Y., USA), and incubated for 60 min at room temperature. Subsequently, 10 µl of 0.8 mM of the substrate L-tryptophan was added, i.e., the final concentration of L-tryptophan was 200 µM. The DMSO concentration in the assay was 0.3%. The concentration of IDO1 was 50 nM. Incubation was continued for 15 min at room temperature. Then, 10 µl of NFK Green™ (NTRC, Oss, The Netherlands) was added and the reaction was developed as described in Example 58 for the IDO1 assay. Fluorescence was read and $IC_{50}$ were calculated also as described above for IDO1. The $IC_{50}$ values of all exemplified compounds were found to be higher than 25 µM.

Example 151

Cytochrome P450 Assays

To determine the inhibitory potency of compounds on CYP3A4 enzyme, the P450-Glo CYP3A4 luciferin isopropylacetal (Luc-IP) assay was used (Promega, Madison, Wis., USA, Cat. No. V9920). The assay makes use of a luminogenic isopropylacetal (IPA) substrate that is a derivative from beetle luciferin, a substrate of luciferase enzymes. The IPA substrate is converted by CYP3A4 to luciferin, which in turn reacts with luciferase to produce an amount of light that is directly proportional to the activity of CYP3A4. Compounds were serially diluted in DMSO and finally in 400 mM $K_2HPO_4$, pH 7.4. 5 µl of compound solution and 5 µl of CYP3A4/substrate solution were combined in the well of a white 384-well Optiplate (Perkin Elmer). The DMSO concentration in the assay was 0.1%. After incubation for 10 minutes at room temperature in the dark, 10 µl of NADPH regeneration system was added and incubation was continued for 10 min. Then, 20 µl of Luciferin Detection Reagent was added to stop the reaction, and incubation was continued for another 20 min. Luminescence was measured on an Envision multimode reader and $IC_{50}$ values were calculated using XLfit™. Concentrations of enzyme, substrate and other reagents were set according to the instructions of the manufacturer (Promega document TB325, revision 3/15). Instead of in a 96-well plate, the assay was performed in 384-well white Perkin Elmer Optiplate (cat. no. 6007290).

A similar assay was used to determine the inhibitory potency of compounds on CYP2D6. The P450-Glo CYP2D6 Luc-IP assay (Promega; Cat. No. V9890) makes use of a luminogenic substrate (ME EGE) that is converted to luciferin by CYP2D6. This assay was performed according to the instruction of the manufacturer (Promega document TB325, revision 3/15), with the difference that it was performed in a 384-well white Perkin Elmer Optiplates (cat. no. 6007290), instead of a 96-well plate. All volumes mentioned in the manufacturer's instruction were divided by a factor 2.5. The DMSO concentration during the incubation phase of the assay was 0.1%. The $IC_{50}$ values of all exemplified compounds were found to be higher than 10 µM in both assays.

The invention claimed is:
1. A compound of Formula I:

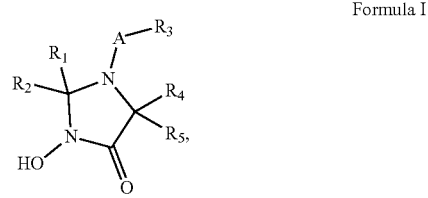

Formula I or a pharmaceutically acceptable salt thereof wherein,
$R^1$ is selected from the group consisting of:

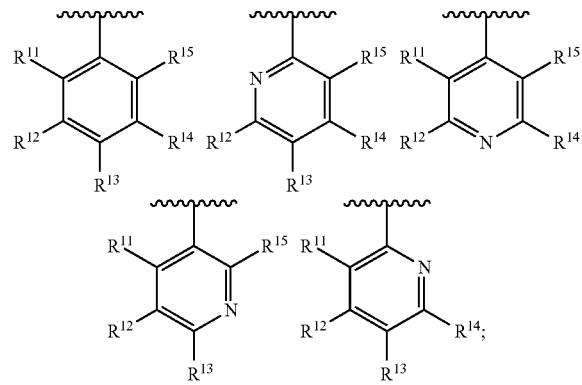

$R^{11}$ is H, halogen, (1-2C)alkyl or (1-2C)alkoxy, all alkyl and alkoxy groups optionally being substituted with one or more halogen;
$R^{12}$ is halogen, (1-2C)alkyl (2-3C)alkenyl, (2-3C)alkynyl, (1-2C)alkoxy, (3-8C)cycloalkyl, or cyano, all alkyl, alkoxy and cycloalkyl groups optionally being substituted with one or more halogen;
$R^{13}$ is H, halogen, (1-2C)alkyl or (1-2C)alkoxy, all alkyl and alkoxy groups optionally being substituted with one or more halogen;
$R^{14}$ is H, halogen, (1-2C)alkyl or (1-2C)alkoxy, all alkyl and alkoxy groups optionally being substituted with one or more halogen;

R<sup>15</sup> is H, halogen, (1-2C)alkyl or (1-2C)alkoxy, all alkyl and alkoxy groups optionally being substituted with one or more halogen;

R² is selected from the group consisting of:
a) hydrogen,
b) (1-6C)alkyl,
wherein (1-6C)alkyl optionally can be substituted, R³ is selected from the group consisting of:
a) (6-10C)aryl,
b) (1-9C)heteroaryl,
c) (3-8C)cycloalkyl,
d) (2-7C)heterocycloalkyl,
e) (1-6C)alkyl,
f) (1-6)alkylamino,
g) (3-6C)cycloalkylamino
h) (6-10C)arylamino,
i) (1-9C)heteroarylamino,
j) (2-7C)heterocycloalkylamino,
wherein all groups optionally can be substituted, R⁴ is selected from the group consisting of:
a) hydrogen,
b) (1-6C)alkyl,
wherein (1-6C)alkyl optionally can be substituted, R⁵ is selected from the group consisting of:
a) hydrogen,
b) (1-6C)alkyl,
wherein (1-6C)alkyl optionally can be substituted, A is selected from CH(R$^a$), C(O), S(O) or SO₂, R$^a$ is selected from the group consisting of:
a) hydrogen,
b) (1-6C)alkyl,
wherein (1-6C)alkyl optionally can be substituted with fluorine or hydroxyl.

2. The compound according to claim 1 wherein R² is hydrogen, and A is C(O) or CH(R$^a$).

3. The compound according to claim 1 wherein R⁴ and R⁵ are selected from the group of hydrogen, methyl, and ethyl, whereby if one of R⁴ and R⁵ is not hydrogen, the other one must be hydrogen.

4. The compound according to claim 1 wherein R¹ is

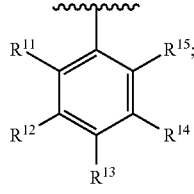

R¹¹ is H, halogen, (1-2C)alkyl or (1-2C)alkoxy, all alkyl and alkoxy groups optionally being substituted with one or more halogen;

R¹² is halogen, (1-2C)alkyl, (2-3C)alkenyl, (2-3C)alkynyl, (1-2C)alkoxy, (3-8C)cycloalkyl, or cyano, all alkyl, alkoxy and cycloalkyl groups optionally being substituted with one or more halogen;

R¹³ is H, halogen, (1-2C)alkyl or (1-2C)alkoxy, all alkyl and alkoxy groups optionally being substituted with one or more halogen;

R¹⁴ is H, halogen, (1-2C)alkyl or (1-2C)alkoxy, all alkyl and alkoxy groups optionally being substituted with one or more halogen;

R¹⁵ is H, halogen, (1-2C)alkyl or (1-2C)alkoxy, all alkyl and alkoxy groups optionally being substituted with one or more halogen.

5. The compound according to claim 1 wherein R¹ is

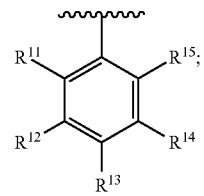

R¹¹, R¹⁵, R¹⁴ is H or fluorine,

R¹² is halogen, (1-2C)alkyl, (2-3C)alkenyl or (2-3C)alkynyl, all alkyl groups optionally being substituted with one or more halogen, R¹³ is H or halogen.

6. The compound according to claim 1 wherein R³ is selected from the group consisting of (6-10C)aryl, (1-9C)heteroaryl, (3-8C)cycloalkyl, (2-7C)heterocycloalkyl, and (1-6C)alkyl, preferably (6-10C)aryl, (1-9C)heteroaryl and (3-8C)cycloalkyl, wherein all groups optionally can be substituted.

7. The compound according to claim 1 wherein R³ is

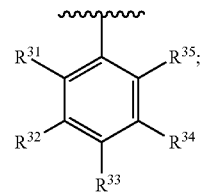

R³¹ and R³⁵ are independently selected from the group consisting of:

hydrogen, halogen, cyano, (1-2C)alkyl, (2-3C)alkenyl, (2-3C)alkynyl and (1-2C)alkoxy, all alkyl and alkoxy groups optionally being substituted with one or more halogen; R³² and R³⁴ are independently selected from the group consisting of:

hydrogen, halogen, cyano, (1-6C)alkyl, (2-3C)alkenyl, (2-3C)alkynyl, (1-2C)alkoxy, (1-3C)alkoxy(1-6C)alkylaminocarbonyl, amino, nitro, (1-6C)alkylcarbonylamino or (1-6C)alkylsulfonylamino, all alkyl and alkoxy groups optionally being substituted with one or more halogen;

R³³ is selected from the group consisting of:

hydrogen, halogen, cyano, (1-6C)alkyl, (2-3C)alkenyl, (2-6C)alkynyl, (1-3C)alkoxy, (6-10C)aryl, (1-5C)heteroaryl, (2-7C)heterocycloalkyl, (3-8C)cycloalkyl, (6-10C)aryloxy, (1-6C)alkylsulfonylamino(1-6C)alkyl, aminosulfonylamino(1-6C)alkyl, (3-8C)cycloalkyl(1-6C)alkyl, (1-6C)alkylcarbonylamino(2-6C)alkynyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, (6-10C)aryl(1-6C)alkyl, (1-3C)alkylsulfonyl(6-10C)aryl, di[(1-6C)alkyl]amino, all alkyl and alkoxy groups optionally being substituted with one or more halogen or hydroxy, all (1-5C) heteroaryl groups optionally being substituted with one or more halogen or one or more (1-6C)alkyl.

8. The compound according to claim 1 wherein $R^3$ is

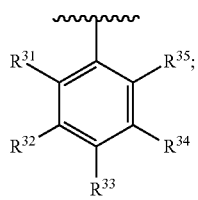

$R^{31}$ and $R^{35}$ are independently selected from the group consisting of: hydrogen, fluoro and chloro; $R^{32}$ and $R^{34}$ are hydrogen; $R^{33}$ hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen or hydroxy, all (1-5C)heteroaryl groups optionally being substituted with one or more halogen or one or more (1-6C)alkyl.

9. A method for inhibiting an indoleamine 2,3-dioxygenase (IDO1), comprising contacting the IDO1 with the compound or the pharmaceutically acceptable salt thereof according to claim 1.

10. A pharmaceutical composition comprising the compound or the pharmaceutically acceptable salt thereof according to claim 1, and one or more pharmaceutically acceptable excipients.

11. The pharmaceutical composition according to claim 10, which further comprises at least one additional therapeutically active agent.

12. A method of treating an increase in indoleamine 2,3-dioxygenase (IDO1) activity associated with diseases, disorders or conditions, comprising administering the compound or the pharmaceutically acceptable salt thereof according to claim 1 to a patient in need of the treating.

13. The method according to claim 12, wherein the diseases, disorders or conditions are selected from cancer, viral or parasitic infections, central nervous system diseases, neuropsychiatric and neurodegenerative diseases, cerebrovascular disease, and immune-related disorders.

14. The compound or the pharmaceutically acceptable salt thereof according to claim 1, wherein the compound or the pharmaceutically acceptable salt thereof has an inhibitory potency on indoleamine 2,3-dioxygenase (IDO1) with an $IC_{50}$ of 25 μM or less.

15. The method according to claim 12, wherein the diseases, disorders or conditions is selected from the group of infection with influenza virus or *Leishmania major*, depression, Huntington's disease, Parkinson's disease, AIDS dementia complex, infections of the central nervous system, malaria, ischemia, hypoxia at birth, traumatic brain injury, epilepsy, anxiety, schizophrenia, inflammatory bowel disease (IBD), colitis Crohn's disease, obesity, and diabetes.

* * * * *